US012385099B2

(12) United States Patent
Chowdhury et al.

(10) Patent No.: US 12,385,099 B2
(45) Date of Patent: *Aug. 12, 2025

(54) CIRCULATING MICRORNA SIGNATURES FOR OVARIAN CANCER

(71) Applicants: Dana-Farber Cancer Institute, Inc., Boston, MA (US); The Brigham and Women's Hospital, Inc., Boston, MA (US); Medical University of Lodz, Lodz (PL)

(72) Inventors: Dipanjan Chowdhury, Brookline, MA (US); Kevin M. Elias, Brookline, MA (US); Wojciech Fendler, Lodz (PL); Konrad Stawiski, Lodz (PL)

(73) Assignees: DANA-FARBER CANCER INSTITUTE, INC., Boston, MA (US); THE BRIGHAM AND WOMEN'S HOSPITAL, INC., Boston, MA (US); MEDICAL UNIVERSITY OF LODZ, Lods (PL)

( * ) Notice: Subject to any disclaimer, the term of this patent is extended or adjusted under 35 U.S.C. 154(b) by 176 days.

This patent is subject to a terminal disclaimer.

(21) Appl. No.: 17/810,495

(22) Filed: Jul. 1, 2022

(65) Prior Publication Data

US 2023/0193396 A1    Jun. 22, 2023

Related U.S. Application Data

(60) Continuation of application No. 17/456,478, filed on Nov. 24, 2021, now abandoned, which is a division of application No. 16/476,799, filed as application No. PCT/US2018/012982 on Jan. 9, 2018, now Pat. No. 11,214,839.

(60) Provisional application No. 62/444,085, filed on Jan. 9, 2017.

(51) Int. Cl.
 C12Q 1/6886 (2018.01)
 C12Q 1/686 (2018.01)
 G16B 30/00 (2019.01)
 G16B 40/00 (2019.01)

(52) U.S. Cl.
 CPC ........... *C12Q 1/6886* (2013.01); *C12Q 1/686* (2013.01); *G16B 30/00* (2019.02); *G16B 40/00* (2019.02); *C12Q 2600/158* (2013.01); *C12Q 2600/178* (2013.01)

(58) Field of Classification Search
 CPC .................. C12Q 1/6886; C12Q 1/686; C12Q 2600/158; C12Q 2600/178; A61P 35/00
 See application file for complete search history.

(56) References Cited

U.S. PATENT DOCUMENTS

| 2005/0261218 A1 | 11/2005 | Esau et al. |
| 2010/0249213 A1 | 9/2010 | Croce |
| 2011/0171664 A1 | 7/2011 | O'Brien |
| 2011/0275534 A1 | 11/2011 | Cohn et al. |
| 2012/0219958 A1 | 8/2012 | Weidhaas |
| 2016/0312301 A1 | 10/2016 | Lee et al. |

FOREIGN PATENT DOCUMENTS

| EP | 2 354 246 A1 | 8/2011 |
| WO | WO 2010/065156 A1 | 6/2010 |

OTHER PUBLICATIONS

Staicu, Cristina Elena, et al. "Role of microRNAs as clinical cancer biomarkers for ovarian cancer: a short overview." Cells 9.1 (2020): 169).*
Kinose, Yasuto, et al. "The role of microRNAs in ovarian cancer." BioMed research international 2014.1 (2014): 249393).*
Wang, Ze-Hua, and Cong-Jian Xu. "Research progress of microRNA in early detection of ovarian cancer." Chinese medical journal 128.24 (2015): 3363-3370.*
Extended European Search Report for EP Application No. 18735999.7, dated Nov. 24, 2020, 7 pages.
International Search Report for International Application No. PCT/US2018/012982, mailed Jun. 7, 2018, 6 pages.
Karst et al., "Ovarian Cancer Pathogenesis: A Model in Evolution", *Journal of Oncology*, vol. 2010, Article ID 932371, 13 pages, 2010, doi: 10.1155/2010/932371.
Merritt et al., "Molecular Pathogenesis of Endometrial and Ovarian Cancer", Cancer Biomarkers 9(1-6):287-305 (2010).
Nakamura et al., "Features of ovarian cancer in Lynch syndrome", *Molecular and Clinical Oncology* 2(6):909-916 (2014).
Vang et al., "Ovarian Low-Grade and High-Grade Serous Carcinoma: Pathogenesis, Clinicopathologic and Molecular Biologic Features, and Diagnostic Problems", *Advances in Anatomic Pathology* 16(5): 267-282 (2009).
Wang et al., Tumor-Associated Circulating MicroRNAs as Biomarkers of Cancer, *Molecules* 19(2):1912-1938, Feb. 10, 2014.
Choo et al., MicroRNA-5p and -3p co-expression and cross-targeting in colon cancer cells. J Biomed Sci 21, 95 (2014).
Kuehbacher et al., Role of Dicer and Drosha for endothelial microRNA expression and angiogenesis. Circ Res 101, 59-68 (2007).

* cited by examiner

*Primary Examiner* — Kimberly Chong
(74) *Attorney, Agent, or Firm* — Mueting Raasch Group

(57) ABSTRACT

Provided herein are methods and kits for determining the presence or absence of certain microRNA biomarkers in a blood sample of a female patient. The microRNA biomarkers are associated with ovarian cancer. Also provided are methods for screening a female subject for the presence or absence of certain microRNA biomarkers, as well as methods for treating a female subject having an ovarian cancer.

8 Claims, 21 Drawing Sheets

Specification includes a Sequence Listing.

SEQUENCE LISTING

```
Sequence total quantity: 192
SEQ ID NO: 1          moltype = RNA    length = 21
FEATURE               Location/Qualifiers
source                1..21
                      mol_type = genomic RNA
                      organism = Homo sapiens
SEQUENCE: 1
ctatacaatc tactgtcttt c                                                 21

SEQ ID NO: 2          moltype = RNA    length = 22
FEATURE               Location/Qualifiers
source                1..22
                      mol_type = genomic RNA
                      organism = Homo sapiens
SEQUENCE: 2
tgaggtagta ggttgtatag tt                                                22

SEQ ID NO: 3          moltype = RNA    length = 22
FEATURE               Location/Qualifiers
source                1..22
                      mol_type = genomic RNA
                      organism = Homo sapiens
SEQUENCE: 3
ctatacaacc tactgccttc cc                                                22

SEQ ID NO: 4          moltype = RNA    length = 22
FEATURE               Location/Qualifiers
source                1..22
                      mol_type = genomic RNA
                      organism = Homo sapiens
SEQUENCE: 4
tgaggtagta ggttgtgtgg tt                                                22

SEQ ID NO: 5          moltype = RNA    length = 22
FEATURE               Location/Qualifiers
source                1..22
                      mol_type = genomic RNA
                      organism = Homo sapiens
SEQUENCE: 5
tgaggtagta ggttgtatgg tt                                                22

SEQ ID NO: 6          moltype = RNA    length = 22
FEATURE               Location/Qualifiers
source                1..22
                      mol_type = genomic RNA
                      organism = Homo sapiens
SEQUENCE: 6
ctatacgacc tgctgccttt ct                                                22

SEQ ID NO: 7          moltype = RNA    length = 22
FEATURE               Location/Qualifiers
source                1..22
                      mol_type = genomic RNA
                      organism = Homo sapiens
SEQUENCE: 7
agaggtagta ggttgcatag tt                                                22

SEQ ID NO: 8          moltype = RNA    length = 22
FEATURE               Location/Qualifiers
source                1..22
                      mol_type = genomic RNA
                      organism = Homo sapiens
SEQUENCE: 8
tgaggtagga ggttgtatag tt                                                22

SEQ ID NO: 9          moltype = RNA    length = 22
FEATURE               Location/Qualifiers
source                1..22
                      mol_type = genomic RNA
                      organism = Homo sapiens
SEQUENCE: 9
tgaggtagta gattgtatag tt                                                22

SEQ ID NO: 10         moltype = RNA    length = 22
FEATURE               Location/Qualifiers
source                1..22
                      mol_type = genomic RNA
                      organism = Homo sapiens
```

```
SEQUENCE: 10
tgaggtagta gtttgtacag tt                                          22

SEQ ID NO: 11         moltype = RNA  length = 22
FEATURE               Location/Qualifiers
source                1..22
                      mol_type = genomic RNA
                      organism = Homo sapiens
SEQUENCE: 11
tgaggtagta gtttgtgctg tt                                          22

SEQ ID NO: 12         moltype = RNA  length = 22
FEATURE               Location/Qualifiers
source                1..22
                      mol_type = genomic RNA
                      organism = Homo sapiens
SEQUENCE: 12
tggaatgtaa agaagtatgt at                                          22

SEQ ID NO: 13         moltype = RNA  length = 23
FEATURE               Location/Qualifiers
source                1..23
                      mol_type = genomic RNA
                      organism = Homo sapiens
SEQUENCE: 13
tggaagacta gtgattttgt tgt                                         23

SEQ ID NO: 14         moltype = RNA  length = 23
FEATURE               Location/Qualifiers
source                1..23
                      mol_type = genomic RNA
                      organism = Homo sapiens
SEQUENCE: 14
taccctgtag atccgaattt gtg                                         23

SEQ ID NO: 15         moltype = RNA  length = 23
FEATURE               Location/Qualifiers
source                1..23
                      mol_type = genomic RNA
                      organism = Homo sapiens
SEQUENCE: 15
taccctgtag aaccgaattt gtg                                         23

SEQ ID NO: 16         moltype = RNA  length = 22
FEATURE               Location/Qualifiers
source                1..22
                      mol_type = genomic RNA
                      organism = Homo sapiens
SEQUENCE: 16
cgaatcatta tttgctgctc ta                                          22

SEQ ID NO: 17         moltype = RNA  length = 22
FEATURE               Location/Qualifiers
source                1..22
                      mol_type = genomic RNA
                      organism = Homo sapiens
SEQUENCE: 17
tagcagcaca tcatggttta ca                                          22

SEQ ID NO: 18         moltype = RNA  length = 22
FEATURE               Location/Qualifiers
source                1..22
                      mol_type = genomic RNA
                      organism = Homo sapiens
SEQUENCE: 18
ccaatattac tgtgctgctt ta                                          22

SEQ ID NO: 19         moltype = RNA  length = 22
FEATURE               Location/Qualifiers
source                1..22
                      mol_type = genomic RNA
                      organism = Homo sapiens
SEQUENCE: 19
tagcagcacg taaatattgg cg                                          22

SEQ ID NO: 20         moltype = RNA  length = 23
FEATURE               Location/Qualifiers
source                1..23
                      mol_type = genomic RNA
```

```
                         organism = Homo sapiens
SEQUENCE: 20
caaagtgctt acagtgcagg tag                                               23

SEQ ID NO: 21            moltype = RNA   length = 23
FEATURE                  Location/Qualifiers
source                   1..23
                         mol_type = genomic RNA
                         organism = Homo sapiens
SEQUENCE: 21
tgtgcaaatc tatgcaaaac tga                                               23

SEQ ID NO: 22            moltype = RNA   length = 23
FEATURE                  Location/Qualifiers
source                   1..23
                         mol_type = genomic RNA
                         organism = Homo sapiens
SEQUENCE: 22
tgtgcaaatc catgcaaaac tga                                               23

SEQ ID NO: 23            moltype = RNA   length = 23
FEATURE                  Location/Qualifiers
source                   1..23
                         mol_type = genomic RNA
                         organism = Homo sapiens
SEQUENCE: 23
taaagtgctt atagtgcagg tag                                               23

SEQ ID NO: 24            moltype = RNA   length = 23
FEATURE                  Location/Qualifiers
source                   1..23
                         mol_type = genomic RNA
                         organism = Homo sapiens
SEQUENCE: 24
caaagtgctc atagtgcagg tag                                               23

SEQ ID NO: 25            moltype = RNA   length = 22
FEATURE                  Location/Qualifiers
source                   1..22
                         mol_type = genomic RNA
                         organism = Homo sapiens
SEQUENCE: 25
tagcttatca gactgatgtt ga                                                22

SEQ ID NO: 26            moltype = RNA   length = 22
FEATURE                  Location/Qualifiers
source                   1..22
                         mol_type = genomic RNA
                         organism = Homo sapiens
SEQUENCE: 26
aagctgccag ttgaagaact gt                                                22

SEQ ID NO: 27            moltype = RNA   length = 22
FEATURE                  Location/Qualifiers
source                   1..22
                         mol_type = genomic RNA
                         organism = Homo sapiens
SEQUENCE: 27
agttcttcag tggcaagctt ta                                                22

SEQ ID NO: 28            moltype = RNA   length = 21
FEATURE                  Location/Qualifiers
source                   1..21
                         mol_type = genomic RNA
                         organism = Homo sapiens
SEQUENCE: 28
atcacattgc cagggatttc c                                                 21

SEQ ID NO: 29            moltype = RNA   length = 21
FEATURE                  Location/Qualifiers
source                   1..21
                         mol_type = genomic RNA
                         organism = Homo sapiens
SEQUENCE: 29
atcacattgc cagggattac c                                                 21

SEQ ID NO: 30            moltype = RNA   length = 22
FEATURE                  Location/Qualifiers
source                   1..22
```

```
                          mol_type = genomic RNA
                          organism = Homo sapiens
SEQUENCE: 30
tgcctactga gctgaaacac ag                                              22

SEQ ID NO: 31             moltype = RNA   length = 22
FEATURE                   Location/Qualifiers
source                    1..22
                          mol_type = genomic RNA
                          organism = Homo sapiens
SEQUENCE: 31
tggctcagtt cagcaggaac ag                                              22

SEQ ID NO: 32             moltype = RNA   length = 22
FEATURE                   Location/Qualifiers
source                    1..22
                          mol_type = genomic RNA
                          organism = Homo sapiens
SEQUENCE: 32
cattgcactt gtctcggtct ga                                              22

SEQ ID NO: 33             moltype = RNA   length = 22
FEATURE                   Location/Qualifiers
source                    1..22
                          mol_type = genomic RNA
                          organism = Homo sapiens
SEQUENCE: 33
ttcaagtaat ccaggatagg ct                                              22

SEQ ID NO: 34             moltype = RNA   length = 21
FEATURE                   Location/Qualifiers
source                    1..21
                          mol_type = genomic RNA
                          organism = Homo sapiens
SEQUENCE: 34
ttcaagtaat tcaggatagg t                                               21

SEQ ID NO: 35             moltype = RNA   length = 21
FEATURE                   Location/Qualifiers
source                    1..21
                          mol_type = genomic RNA
                          organism = Homo sapiens
SEQUENCE: 35
ttcacagtgg ctaagttccg c                                               21

SEQ ID NO: 36             moltype = RNA   length = 21
FEATURE                   Location/Qualifiers
source                    1..21
                          mol_type = genomic RNA
                          organism = Homo sapiens
SEQUENCE: 36
ttcacagtgg ctaagttctg c                                               21

SEQ ID NO: 37             moltype = RNA   length = 22
FEATURE                   Location/Qualifiers
source                    1..22
                          mol_type = genomic RNA
                          organism = Homo sapiens
SEQUENCE: 37
cactagattg tgagctcctg ga                                              22

SEQ ID NO: 38             moltype = RNA   length = 22
FEATURE                   Location/Qualifiers
source                    1..22
                          mol_type = genomic RNA
                          organism = Homo sapiens
SEQUENCE: 38
aaggagctca cagtctattg ag                                              22

SEQ ID NO: 39             moltype = RNA   length = 22
FEATURE                   Location/Qualifiers
source                    1..22
                          mol_type = genomic RNA
                          organism = Homo sapiens
SEQUENCE: 39
tagcaccatc tgaaatcggt ta                                              22

SEQ ID NO: 40             moltype = RNA   length = 22
FEATURE                   Location/Qualifiers
```

```
source                  1..22
                        mol_type = genomic RNA
                        organism = Homo sapiens
SEQUENCE: 40
ctttcagtcg gatgtttgca gc                                              22

SEQ ID NO: 41           moltype = RNA   length = 22
FEATURE                 Location/Qualifiers
source                  1..22
                        mol_type = genomic RNA
                        organism = Homo sapiens
SEQUENCE: 41
tgtaaacatc ctcgactgga ag                                              22

SEQ ID NO: 42           moltype = RNA   length = 23
FEATURE                 Location/Qualifiers
source                  1..23
                        mol_type = genomic RNA
                        organism = Homo sapiens
SEQUENCE: 42
tgtaaacatc ctacactctc agc                                             23

SEQ ID NO: 43           moltype = RNA   length = 22
FEATURE                 Location/Qualifiers
source                  1..22
                        mol_type = genomic RNA
                        organism = Homo sapiens
SEQUENCE: 43
tgtaaacatc cccgactgga ag                                              22

SEQ ID NO: 44           moltype = RNA   length = 22
FEATURE                 Location/Qualifiers
source                  1..22
                        mol_type = genomic RNA
                        organism = Homo sapiens
SEQUENCE: 44
ctttcagtcg gatgtttaca gc                                              22

SEQ ID NO: 45           moltype = RNA   length = 22
FEATURE                 Location/Qualifiers
source                  1..22
                        mol_type = genomic RNA
                        organism = Homo sapiens
SEQUENCE: 45
tgtaaacatc cttgactgga ag                                              22

SEQ ID NO: 46           moltype = RNA   length = 22
FEATURE                 Location/Qualifiers
source                  1..22
                        mol_type = genomic RNA
                        organism = Homo sapiens
SEQUENCE: 46
tattgcacat tactaagttg ca                                              22

SEQ ID NO: 47           moltype = RNA   length = 22
FEATURE                 Location/Qualifiers
source                  1..22
                        mol_type = genomic RNA
                        organism = Homo sapiens
SEQUENCE: 47
tattgcactt gtcccggcct gt                                              22

SEQ ID NO: 48           moltype = RNA   length = 22
FEATURE                 Location/Qualifiers
source                  1..22
                        mol_type = genomic RNA
                        organism = Homo sapiens
SEQUENCE: 48
tattgcactc gtcccggcct cc                                              22

SEQ ID NO: 49           moltype = RNA   length = 23
FEATURE                 Location/Qualifiers
source                  1..23
                        mol_type = genomic RNA
                        organism = Homo sapiens
SEQUENCE: 49
caaagtgctg ttcgtgcagg tag                                             23

SEQ ID NO: 50           moltype = RNA   length = 22
```

```
FEATURE              Location/Qualifiers
source               1..22
                     mol_type = genomic RNA
                     organism = Homo sapiens
SEQUENCE: 50
tgaggtagta agttgtattg tt                                              22

SEQ ID NO: 51        moltype = RNA   length = 22
FEATURE              Location/Qualifiers
source               1..22
                     mol_type = genomic RNA
                     organism = Homo sapiens
SEQUENCE: 51
aacccgtaga tccgatcttg tg                                              22

SEQ ID NO: 52        moltype = RNA   length = 22
FEATURE              Location/Qualifiers
source               1..22
                     mol_type = genomic RNA
                     organism = Homo sapiens
SEQUENCE: 52
cacccgtaga accgaccttg cg                                              22

SEQ ID NO: 53        moltype = RNA   length = 22
FEATURE              Location/Qualifiers
source               1..22
                     mol_type = genomic RNA
                     organism = Homo sapiens
SEQUENCE: 53
aacccgtaga tccgaacttg tg                                              22

SEQ ID NO: 54        moltype = RNA   length = 21
FEATURE              Location/Qualifiers
source               1..21
                     mol_type = genomic RNA
                     organism = Homo sapiens
SEQUENCE: 54
tacagtactg tgataactga a                                               21

SEQ ID NO: 55        moltype = RNA   length = 23
FEATURE              Location/Qualifiers
source               1..23
                     mol_type = genomic RNA
                     organism = Homo sapiens
SEQUENCE: 55
agcagcattg tacagggcta tga                                             23

SEQ ID NO: 56        moltype = RNA   length = 22
FEATURE              Location/Qualifiers
source               1..22
                     mol_type = genomic RNA
                     organism = Homo sapiens
SEQUENCE: 56
ccgcactgtg ggtacttgct gc                                              22

SEQ ID NO: 57        moltype = RNA   length = 21
FEATURE              Location/Qualifiers
source               1..21
                     mol_type = genomic RNA
                     organism = Homo sapiens
SEQUENCE: 57
taaagtgctg acagtgcaga t                                               21

SEQ ID NO: 58        moltype = RNA   length = 23
FEATURE              Location/Qualifiers
source               1..23
                     mol_type = genomic RNA
                     organism = Homo sapiens
SEQUENCE: 58
agcagcattg tacagggcta tca                                             23

SEQ ID NO: 59        moltype = RNA   length = 22
FEATURE              Location/Qualifiers
source               1..22
                     mol_type = genomic RNA
                     organism = Homo sapiens
SEQUENCE: 59
tggagtgtga caatggtgtt tg                                              22
```

-continued

```
SEQ ID NO: 60              moltype = RNA   length = 24
FEATURE                    Location/Qualifiers
source                     1..24
                           mol_type = genomic RNA
                           organism = Homo sapiens
SEQUENCE: 60
tccctgagac cctttaacct gtga                                           24

SEQ ID NO: 61              moltype = RNA   length = 22
FEATURE                    Location/Qualifiers
source                     1..22
                           mol_type = genomic RNA
                           organism = Homo sapiens
SEQUENCE: 61
tccctgagac cctaacttgt ga                                             22

SEQ ID NO: 62              moltype = RNA   length = 22
FEATURE                    Location/Qualifiers
source                     1..22
                           mol_type = genomic RNA
                           organism = Homo sapiens
SEQUENCE: 62
tcgtaccgtg agtaataatg cg                                             22

SEQ ID NO: 63              moltype = RNA   length = 21
FEATURE                    Location/Qualifiers
source                     1..21
                           mol_type = genomic RNA
                           organism = Homo sapiens
SEQUENCE: 63
cattattact tttggtacgc g                                              21

SEQ ID NO: 64              moltype = RNA   length = 21
FEATURE                    Location/Qualifiers
source                     1..21
                           mol_type = genomic RNA
                           organism = Homo sapiens
SEQUENCE: 64
tcacagtgaa ccggtctctt t                                              21

SEQ ID NO: 65              moltype = RNA   length = 22
FEATURE                    Location/Qualifiers
source                     1..22
                           mol_type = genomic RNA
                           organism = Homo sapiens
SEQUENCE: 65
cagtgcaatg ttaaaagggc at                                             22

SEQ ID NO: 66              moltype = RNA   length = 21
FEATURE                    Location/Qualifiers
source                     1..21
                           mol_type = genomic RNA
                           organism = Homo sapiens
SEQUENCE: 66
actctttccc tgttgcacta c                                              21

SEQ ID NO: 67              moltype = RNA   length = 22
FEATURE                    Location/Qualifiers
source                     1..22
                           mol_type = genomic RNA
                           organism = Homo sapiens
SEQUENCE: 67
tgtgactggt tgaccagagg gg                                             22

SEQ ID NO: 68              moltype = RNA   length = 23
FEATURE                    Location/Qualifiers
source                     1..23
                           mol_type = genomic RNA
                           organism = Homo sapiens
SEQUENCE: 68
tggagacgcg gccctgttgg agt                                            23

SEQ ID NO: 69              moltype = RNA   length = 23
FEATURE                    Location/Qualifiers
source                     1..23
                           mol_type = genomic RNA
                           organism = Homo sapiens
SEQUENCE: 69
tctacagtgc acgtgtctcc agt                                            23
```

```
SEQ ID NO: 70          moltype = RNA   length = 21
FEATURE                Location/Qualifiers
source                 1..21
                       mol_type = genomic RNA
                       organism = Homo sapiens
SEQUENCE: 70
taccacaggg tagaaccacg g                                                   21

SEQ ID NO: 71          moltype = RNA   length = 22
FEATURE                Location/Qualifiers
source                 1..22
                       mol_type = genomic RNA
                       organism = Homo sapiens
SEQUENCE: 71
cagtggtttt accctatggt ag                                                  22

SEQ ID NO: 72          moltype = RNA   length = 23
FEATURE                Location/Qualifiers
source                 1..23
                       mol_type = genomic RNA
                       organism = Homo sapiens
SEQUENCE: 72
tgtagtgttt cctactttat gga                                                 23

SEQ ID NO: 73          moltype = RNA   length = 21
FEATURE                Location/Qualifiers
source                 1..21
                       mol_type = genomic RNA
                       organism = Homo sapiens
SEQUENCE: 73
cataaagtag aaagcactac t                                                   21

SEQ ID NO: 74          moltype = RNA   length = 21
FEATURE                Location/Qualifiers
source                 1..21
                       mol_type = genomic RNA
                       organism = Homo sapiens
SEQUENCE: 74
tgagatgaag cactgtagct c                                                   21

SEQ ID NO: 75          moltype = RNA   length = 20
FEATURE                Location/Qualifiers
source                 1..20
                       mol_type = genomic RNA
                       organism = Homo sapiens
SEQUENCE: 75
tacagtatag atgatgtact                                                     20

SEQ ID NO: 76          moltype = RNA   length = 22
FEATURE                Location/Qualifiers
source                 1..22
                       mol_type = genomic RNA
                       organism = Homo sapiens
SEQUENCE: 76
ggatatcatc atatactgta ag                                                  22

SEQ ID NO: 77          moltype = RNA   length = 22
FEATURE                Location/Qualifiers
source                 1..22
                       mol_type = genomic RNA
                       organism = Homo sapiens
SEQUENCE: 77
ggattcctgg aaatactgtt ct                                                  22

SEQ ID NO: 78          moltype = RNA   length = 22
FEATURE                Location/Qualifiers
source                 1..22
                       mol_type = genomic RNA
                       organism = Homo sapiens
SEQUENCE: 78
tgagaactga attccatggg tt                                                  22

SEQ ID NO: 79          moltype = RNA   length = 22
FEATURE                Location/Qualifiers
source                 1..22
                       mol_type = genomic RNA
                       organism = Homo sapiens
SEQUENCE: 79
```

-continued

```
tgagaactga attccatagg ct                                              22

SEQ ID NO: 80          moltype = RNA   length = 22
FEATURE                Location/Qualifiers
source                 1..22
                       mol_type = genomic RNA
                       organism = Homo sapiens
SEQUENCE: 80
tcagtgcact acagaacttt gt                                              22

SEQ ID NO: 81          moltype = RNA   length = 22
FEATURE                Location/Qualifiers
source                 1..22
                       mol_type = genomic RNA
                       organism = Homo sapiens
SEQUENCE: 81
aaagttctga gacactccga ct                                              22

SEQ ID NO: 82          moltype = RNA   length = 22
FEATURE                Location/Qualifiers
source                 1..22
                       mol_type = genomic RNA
                       organism = Homo sapiens
SEQUENCE: 82
tcagtgcatc acagaacttt gt                                              22

SEQ ID NO: 83          moltype = RNA   length = 22
FEATURE                Location/Qualifiers
source                 1..22
                       mol_type = genomic RNA
                       organism = Homo sapiens
SEQUENCE: 83
tctcccaacc cttgtaccag tg                                              22

SEQ ID NO: 84          moltype = RNA   length = 21
FEATURE                Location/Qualifiers
source                 1..21
                       mol_type = genomic RNA
                       organism = Homo sapiens
SEQUENCE: 84
ctagactgaa gctccttgag g                                               21

SEQ ID NO: 85          moltype = RNA   length = 21
FEATURE                Location/Qualifiers
source                 1..21
                       mol_type = genomic RNA
                       organism = Homo sapiens
SEQUENCE: 85
tcagtgcatg acagaacttg g                                               21

SEQ ID NO: 86          moltype = RNA   length = 23
FEATURE                Location/Qualifiers
source                 1..23
                       mol_type = genomic RNA
                       organism = Homo sapiens
SEQUENCE: 86
ttaatgctaa tcgtgatagg ggt                                             23

SEQ ID NO: 87          moltype = RNA   length = 22
FEATURE                Location/Qualifiers
source                 1..22
                       mol_type = genomic RNA
                       organism = Homo sapiens
SEQUENCE: 87
accactgacc gttgactgta cc                                              22

SEQ ID NO: 88          moltype = RNA   length = 23
FEATURE                Location/Qualifiers
source                 1..23
                       mol_type = genomic RNA
                       organism = Homo sapiens
SEQUENCE: 88
aacattcaac gctgtcggtg agt                                             23

SEQ ID NO: 89          moltype = RNA   length = 23
FEATURE                Location/Qualifiers
source                 1..23
                       mol_type = genomic RNA
                       organism = Homo sapiens
```

```
SEQUENCE: 89
aacattcatt gctgtcggtg ggt                                              23

SEQ ID NO: 90            moltype = RNA   length = 23
FEATURE                  Location/Qualifiers
source                   1..23
                         mol_type = genomic RNA
                         organism = Homo sapiens
SEQUENCE: 90
aacattcatt gttgtcggtg ggt                                              23

SEQ ID NO: 91            moltype = RNA   length = 24
FEATURE                  Location/Qualifiers
source                   1..24
                         mol_type = genomic RNA
                         organism = Homo sapiens
SEQUENCE: 91
tttggcaatg gtagaactca cact                                             24

SEQ ID NO: 92            moltype = RNA   length = 22
FEATURE                  Location/Qualifiers
source                   1..22
                         mol_type = genomic RNA
                         organism = Homo sapiens
SEQUENCE: 92
tatggcactg gtagaattca ct                                               22

SEQ ID NO: 93            moltype = RNA   length = 22
FEATURE                  Location/Qualifiers
source                   1..22
                         mol_type = genomic RNA
                         organism = Homo sapiens
SEQUENCE: 93
agggctggc tttcctctgg tc                                                22

SEQ ID NO: 94            moltype = RNA   length = 22
FEATURE                  Location/Qualifiers
source                   1..22
                         mol_type = genomic RNA
                         organism = Homo sapiens
SEQUENCE: 94
tggagagaaa ggcagttcct ga                                               22

SEQ ID NO: 95            moltype = RNA   length = 22
FEATURE                  Location/Qualifiers
source                   1..22
                         mol_type = genomic RNA
                         organism = Homo sapiens
SEQUENCE: 95
caaagaattc tccttttggg ct                                               22

SEQ ID NO: 96            moltype = RNA   length = 23
FEATURE                  Location/Qualifiers
source                   1..23
                         mol_type = genomic RNA
                         organism = Homo sapiens
SEQUENCE: 96
caacggaatc ccaaaagcag ctg                                              23

SEQ ID NO: 97            moltype = RNA   length = 21
FEATURE                  Location/Qualifiers
source                   1..21
                         mol_type = genomic RNA
                         organism = Homo sapiens
SEQUENCE: 97
ctgacctatg aattgacagc c                                                21

SEQ ID NO: 98            moltype = RNA   length = 22
FEATURE                  Location/Qualifiers
source                   1..22
                         mol_type = genomic RNA
                         organism = Homo sapiens
SEQUENCE: 98
tgggtctttg cgggcgagat ga                                               22

SEQ ID NO: 99            moltype = RNA   length = 22
FEATURE                  Location/Qualifiers
source                   1..22
                         mol_type = genomic RNA
```

```
                         organism = Homo sapiens
SEQUENCE: 99
tgtaacagca actccatgtg ga                                              22

SEQ ID NO: 100           moltype = RNA  length = 22
FEATURE                  Location/Qualifiers
source                   1..22
                         mol_type = genomic RNA
                         organism = Homo sapiens
SEQUENCE: 100
ttcaccacct tctccaccca gc                                              22

SEQ ID NO: 101           moltype = RNA  length = 22
FEATURE                  Location/Qualifiers
source                   1..22
                         mol_type = genomic RNA
                         organism = Homo sapiens
SEQUENCE: 101
acagtagtct gcacattggt ta                                              22

SEQ ID NO: 102           moltype = RNA  length = 23
FEATURE                  Location/Qualifiers
source                   1..23
                         mol_type = genomic RNA
                         organism = Homo sapiens
SEQUENCE: 102
cccagtgttc agactacctg ttc                                             23

SEQ ID NO: 103           moltype = RNA  length = 22
FEATURE                  Location/Qualifiers
source                   1..22
                         mol_type = genomic RNA
                         organism = Homo sapiens
SEQUENCE: 103
acagtagtct gcacattggt ta                                              22

SEQ ID NO: 104           moltype = RNA  length = 22
FEATURE                  Location/Qualifiers
source                   1..22
                         mol_type = genomic RNA
                         organism = Homo sapiens
SEQUENCE: 104
taacactgtc tggtaacgat gt                                              22

SEQ ID NO: 105           moltype = RNA  length = 23
FEATURE                  Location/Qualifiers
source                   1..23
                         mol_type = genomic RNA
                         organism = Homo sapiens
SEQUENCE: 105
taatactgcc gggtaatgat gga                                             23

SEQ ID NO: 106           moltype = RNA  length = 22
FEATURE                  Location/Qualifiers
source                   1..22
                         mol_type = genomic RNA
                         organism = Homo sapiens
SEQUENCE: 106
gtgaaatgtt taggaccact ag                                              22

SEQ ID NO: 107           moltype = RNA  length = 21
FEATURE                  Location/Qualifiers
source                   1..21
                         mol_type = genomic RNA
                         organism = Homo sapiens
SEQUENCE: 107
atgacctatg aattgacaga c                                               21

SEQ ID NO: 108           moltype = RNA  length = 23
FEATURE                  Location/Qualifiers
source                   1..23
                         mol_type = genomic RNA
                         organism = Homo sapiens
SEQUENCE: 108
agctacattg tctgctgggt ttc                                             23

SEQ ID NO: 109           moltype = RNA  length = 21
FEATURE                  Location/Qualifiers
source                   1..21
```

```
                            mol_type = genomic RNA
                            organism = Homo sapiens
SEQUENCE: 109
agctacatct ggctactggg t                                              21

SEQ ID NO: 110              moltype = RNA  length = 22
FEATURE                     Location/Qualifiers
source                      1..22
                            mol_type = genomic RNA
                            organism = Homo sapiens
SEQUENCE: 110
tgtcagtttg tcaaataccc ca                                             22

SEQ ID NO: 111              moltype = RNA  length = 22
FEATURE                     Location/Qualifiers
source                      1..22
                            mol_type = genomic RNA
                            organism = Homo sapiens
SEQUENCE: 111
cgtgtatttg acaagctgag tt                                             22

SEQ ID NO: 112              moltype = RNA  length = 21
FEATURE                     Location/Qualifiers
source                      1..21
                            mol_type = genomic RNA
                            organism = Homo sapiens
SEQUENCE: 112
caagtcacta gtggttccgt t                                              21

SEQ ID NO: 113              moltype = RNA  length = 22
FEATURE                     Location/Qualifiers
source                      1..22
                            mol_type = genomic RNA
                            organism = Homo sapiens
SEQUENCE: 113
aaaagctggg ttgagagggc ga                                             22

SEQ ID NO: 114              moltype = RNA  length = 22
FEATURE                     Location/Qualifiers
source                      1..22
                            mol_type = genomic RNA
                            organism = Homo sapiens
SEQUENCE: 114
aaaagctggg ttgagagggc aa                                             22

SEQ ID NO: 115              moltype = RNA  length = 20
FEATURE                     Location/Qualifiers
source                      1..20
                            mol_type = genomic RNA
                            organism = Homo sapiens
SEQUENCE: 115
aaaagctggg ttgagagggt                                                20

SEQ ID NO: 116              moltype = RNA  length = 19
FEATURE                     Location/Qualifiers
source                      1..19
                            mol_type = genomic RNA
                            organism = Homo sapiens
SEQUENCE: 116
aaaagctggg ttgagagga                                                 19

SEQ ID NO: 117              moltype = RNA  length = 21
FEATURE                     Location/Qualifiers
source                      1..21
                            mol_type = genomic RNA
                            organism = Homo sapiens
SEQUENCE: 117
cacattacac ggtcgacctc t                                              21

SEQ ID NO: 118              moltype = RNA  length = 22
FEATURE                     Location/Qualifiers
source                      1..22
                            mol_type = genomic RNA
                            organism = Homo sapiens
SEQUENCE: 118
cccaatacac ggtcgacctc tt                                             22

SEQ ID NO: 119              moltype = RNA  length = 22
FEATURE                     Location/Qualifiers
```

```
source                  1..22
                        mol_type = genomic RNA
                        organism = Homo sapiens
SEQUENCE: 119
ctggccctct ctgcccttcc gt                                                   22

SEQ ID NO: 120          moltype = RNA   length = 23
FEATURE                 Location/Qualifiers
source                  1..23
                        mol_type = genomic RNA
                        organism = Homo sapiens
SEQUENCE: 120
gcaaagcaca cggcctgcag aga                                                  23

SEQ ID NO: 121          moltype = RNA   length = 22
FEATURE                 Location/Qualifiers
source                  1..22
                        mol_type = genomic RNA
                        organism = Homo sapiens
SEQUENCE: 121
tttttcatta ttgctcctga cc                                                   22

SEQ ID NO: 122          moltype = RNA   length = 23
FEATURE                 Location/Qualifiers
source                  1..23
                        mol_type = genomic RNA
                        organism = Homo sapiens
SEQUENCE: 122
tcaagagcaa taacgaaaaa tgt                                                  23

SEQ ID NO: 123          moltype = RNA   length = 22
FEATURE                 Location/Qualifiers
source                  1..22
                        mol_type = genomic RNA
                        organism = Homo sapiens
SEQUENCE: 123
aacaatatcc tggtgctgag tg                                                   22

SEQ ID NO: 124          moltype = RNA   length = 23
FEATURE                 Location/Qualifiers
source                  1..23
                        mol_type = genomic RNA
                        organism = Homo sapiens
SEQUENCE: 124
tgagcgcctc gacgacagag ccg                                                  23

SEQ ID NO: 125          moltype = RNA   length = 22
FEATURE                 Location/Qualifiers
source                  1..22
                        mol_type = genomic RNA
                        organism = Homo sapiens
SEQUENCE: 125
tccgtctcag ttactttata gc                                                   22

SEQ ID NO: 126          moltype = RNA   length = 22
FEATURE                 Location/Qualifiers
source                  1..22
                        mol_type = genomic RNA
                        organism = Homo sapiens
SEQUENCE: 126
ttataaagca atgagactga tt                                                   22

SEQ ID NO: 127          moltype = RNA   length = 21
FEATURE                 Location/Qualifiers
source                  1..21
                        mol_type = genomic RNA
                        organism = Homo sapiens
SEQUENCE: 127
aggggtgcta tctgtgattg a                                                    21

SEQ ID NO: 128          moltype = RNA   length = 22
FEATURE                 Location/Qualifiers
source                  1..22
                        mol_type = genomic RNA
                        organism = Homo sapiens
SEQUENCE: 128
gctgactcct agtccagggc tc                                                   22

SEQ ID NO: 129          moltype = RNA   length = 23
```

-continued

```
FEATURE                 Location/Qualifiers
source                  1..23
                        mol_type = genomic RNA
                        organism = Homo sapiens
SEQUENCE: 129
tcccccaggt gtgattctga ttt                                                 23

SEQ ID NO: 130          moltype = RNA   length = 22
FEATURE                 Location/Qualifiers
source                  1..22
                        mol_type = genomic RNA
                        organism = Homo sapiens
SEQUENCE: 130
ttatcagaat ctccaggggt ac                                                  22

SEQ ID NO: 131          moltype = RNA   length = 22
FEATURE                 Location/Qualifiers
source                  1..22
                        mol_type = genomic RNA
                        organism = Homo sapiens
SEQUENCE: 131
aattgcacgg tatccatctg ta                                                  22

SEQ ID NO: 132          moltype = RNA   length = 22
FEATURE                 Location/Qualifiers
source                  1..22
                        mol_type = genomic RNA
                        organism = Homo sapiens
SEQUENCE: 132
gcctgctggg gtggaacctg gt                                                  22

SEQ ID NO: 133          moltype = RNA   length = 22
FEATURE                 Location/Qualifiers
source                  1..22
                        mol_type = genomic RNA
                        organism = Homo sapiens
SEQUENCE: 133
ttataataca acctgataag tg                                                  22

SEQ ID NO: 134          moltype = RNA   length = 22
FEATURE                 Location/Qualifiers
source                  1..22
                        mol_type = genomic RNA
                        organism = Homo sapiens
SEQUENCE: 134
tttgttcgtt cggctcgcgt ga                                                  22

SEQ ID NO: 135          moltype = RNA   length = 22
FEATURE                 Location/Qualifiers
source                  1..22
                        mol_type = genomic RNA
                        organism = Homo sapiens
SEQUENCE: 135
actggacttg gagtcagaag gc                                                  22

SEQ ID NO: 136          moltype = RNA   length = 25
FEATURE                 Location/Qualifiers
source                  1..25
                        mol_type = genomic RNA
                        organism = Homo sapiens
SEQUENCE: 136
actggacttg gagtcagaag agtgg                                               25

SEQ ID NO: 137          moltype = RNA   length = 21
FEATURE                 Location/Qualifiers
source                  1..21
                        mol_type = genomic RNA
                        organism = Homo sapiens
SEQUENCE: 137
tggtagacta tggaacgtag g                                                   21

SEQ ID NO: 138          moltype = RNA   length = 22
FEATURE                 Location/Qualifiers
source                  1..22
                        mol_type = genomic RNA
                        organism = Homo sapiens
SEQUENCE: 138
tatacaaggg caagctctct gt                                                  22
```

```
SEQ ID NO: 139          moltype = RNA  length = 22
FEATURE                 Location/Qualifiers
source                  1..22
                        mol_type = genomic RNA
                        organism = Homo sapiens
SEQUENCE: 139
gaagttgttc gtggtggatt cg                                                22

SEQ ID NO: 140          moltype = RNA  length = 22
FEATURE                 Location/Qualifiers
source                  1..22
                        mol_type = genomic RNA
                        organism = Homo sapiens
SEQUENCE: 140
gaatgttgct cggtgaaccc ct                                                22

SEQ ID NO: 141          moltype = RNA  length = 23
FEATURE                 Location/Qualifiers
source                  1..23
                        mol_type = genomic RNA
                        organism = Homo sapiens
SEQUENCE: 141
atcaacagac attaattggg cgc                                               23

SEQ ID NO: 142          moltype = RNA  length = 23
FEATURE                 Location/Qualifiers
source                  1..23
                        mol_type = genomic RNA
                        organism = Homo sapiens
SEQUENCE: 142
agctcggtct gaggcccctc agt                                               23

SEQ ID NO: 143          moltype = RNA  length = 23
FEATURE                 Location/Qualifiers
source                  1..23
                        mol_type = genomic RNA
                        organism = Homo sapiens
SEQUENCE: 143
tgaggggcag agagcgagac ttt                                               23

SEQ ID NO: 144          moltype = RNA  length = 21
FEATURE                 Location/Qualifiers
source                  1..21
                        mol_type = genomic RNA
                        organism = Homo sapiens
SEQUENCE: 144
caaaacgtga ggcgctgcta t                                                 21

SEQ ID NO: 145          moltype = RNA  length = 22
FEATURE                 Location/Qualifiers
source                  1..22
                        mol_type = genomic RNA
                        organism = Homo sapiens
SEQUENCE: 145
atcgggaatg tcgtgtccgc cc                                                22

SEQ ID NO: 146          moltype = RNA  length = 23
FEATURE                 Location/Qualifiers
source                  1..23
                        mol_type = genomic RNA
                        organism = Homo sapiens
SEQUENCE: 146
aatgacacga tcactcccgt tga                                               23

SEQ ID NO: 147          moltype = RNA  length = 23
FEATURE                 Location/Qualifiers
source                  1..23
                        mol_type = genomic RNA
                        organism = Homo sapiens
SEQUENCE: 147
tcttggagta ggtcattggg tgg                                               23

SEQ ID NO: 148          moltype = RNA  length = 22
FEATURE                 Location/Qualifiers
source                  1..22
                        mol_type = genomic RNA
                        organism = Homo sapiens
SEQUENCE: 148
ttttgcgatg tgttcctaat at                                                22
```

```
SEQ ID NO: 149          moltype = RNA   length = 22
FEATURE                 Location/Qualifiers
source                  1..22
                        mol_type = genomic RNA
                        organism = Homo sapiens
SEQUENCE: 149
ttttgcaata tgttcctgaa ta                                                   22

SEQ ID NO: 150          moltype = RNA   length = 22
FEATURE                 Location/Qualifiers
source                  1..22
                        mol_type = genomic RNA
                        organism = Homo sapiens
SEQUENCE: 150
aaaccgttac cattactgag tt                                                   22

SEQ ID NO: 151          moltype = RNA   length = 22
FEATURE                 Location/Qualifiers
source                  1..22
                        mol_type = genomic RNA
                        organism = Homo sapiens
SEQUENCE: 151
aagacgggag gaaagaaggg ag                                                   22

SEQ ID NO: 152          moltype = RNA   length = 22
FEATURE                 Location/Qualifiers
source                  1..22
                        mol_type = genomic RNA
                        organism = Homo sapiens
SEQUENCE: 152
tcaggctcag tcccctcccg at                                                   22

SEQ ID NO: 153          moltype = RNA   length = 21
FEATURE                 Location/Qualifiers
source                  1..21
                        mol_type = genomic RNA
                        organism = Homo sapiens
SEQUENCE: 153
cggggcagct cagtacagga t                                                    21

SEQ ID NO: 154          moltype = RNA   length = 22
FEATURE                 Location/Qualifiers
source                  1..22
                        mol_type = genomic RNA
                        organism = Homo sapiens
SEQUENCE: 154
tcctgtactg agctgccccg ag                                                   22

SEQ ID NO: 155          moltype = RNA   length = 22
FEATURE                 Location/Qualifiers
source                  1..22
                        mol_type = genomic RNA
                        organism = Homo sapiens
SEQUENCE: 155
ttgtacatgg taggctttca tt                                                   22

SEQ ID NO: 156          moltype = RNA   length = 22
FEATURE                 Location/Qualifiers
source                  1..22
                        mol_type = genomic RNA
                        organism = Homo sapiens
SEQUENCE: 156
atgcacctgg gcaaggattc tg                                                   22

SEQ ID NO: 157          moltype = RNA   length = 22
FEATURE                 Location/Qualifiers
source                  1..22
                        mol_type = genomic RNA
                        organism = Homo sapiens
SEQUENCE: 157
aatgcacccg ggcaaggatt ct                                                   22

SEQ ID NO: 158          moltype = RNA   length = 22
FEATURE                 Location/Qualifiers
source                  1..22
                        mol_type = genomic RNA
                        organism = Homo sapiens
SEQUENCE: 158
```

```
aatgcacctg ggcaaggatt ca                                              22

SEQ ID NO: 159          moltype = RNA   length = 23
FEATURE                 Location/Qualifiers
source                  1..23
                        mol_type = genomic RNA
                        organism = Homo sapiens
SEQUENCE: 159
tagcagcggg aacagttctg cag                                             23

SEQ ID NO: 160          moltype = RNA   length = 22
FEATURE                 Location/Qualifiers
source                  1..22
                        mol_type = genomic RNA
                        organism = Homo sapiens
SEQUENCE: 160
catgccttga gtgtaggacc gt                                              22

SEQ ID NO: 161          moltype = RNA   length = 22
FEATURE                 Location/Qualifiers
source                  1..22
                        mol_type = genomic RNA
                        organism = Homo sapiens
SEQUENCE: 161
aaacattcgc ggtgcacttc tt                                              22

SEQ ID NO: 162          moltype = RNA   length = 23
FEATURE                 Location/Qualifiers
source                  1..23
                        mol_type = genomic RNA
                        organism = Homo sapiens
SEQUENCE: 162
agtgcctgag ggagtaagag ccc                                             23

SEQ ID NO: 163          moltype = RNA   length = 23
FEATURE                 Location/Qualifiers
source                  1..23
                        mol_type = genomic RNA
                        organism = Homo sapiens
SEQUENCE: 163
tgagtgtgtg tgtgtgagtg tgt                                             23

SEQ ID NO: 164          moltype = RNA   length = 22
FEATURE                 Location/Qualifiers
source                  1..22
                        mol_type = genomic RNA
                        organism = Homo sapiens
SEQUENCE: 164
aagatgtgga aaaattggaa tc                                              22

SEQ ID NO: 165          moltype = RNA   length = 22
FEATURE                 Location/Qualifiers
source                  1..22
                        mol_type = genomic RNA
                        organism = Homo sapiens
SEQUENCE: 165
ttatggtttg cctgggactg ag                                              22

SEQ ID NO: 166          moltype = RNA   length = 22
FEATURE                 Location/Qualifiers
source                  1..22
                        mol_type = genomic RNA
                        organism = Homo sapiens
SEQUENCE: 166
tgagaaccac gtctgctctg ag                                              22

SEQ ID NO: 167          moltype = RNA   length = 22
FEATURE                 Location/Qualifiers
source                  1..22
                        mol_type = genomic RNA
                        organism = Homo sapiens
SEQUENCE: 167
gactatagaa ctttccccct ca                                              22

SEQ ID NO: 168          moltype = RNA   length = 21
FEATURE                 Location/Qualifiers
source                  1..21
                        mol_type = genomic RNA
                        organism = Homo sapiens
```

```
SEQUENCE: 168
tgggtttacg ttgggagaac t                                              21

SEQ ID NO: 169         moltype = RNA   length = 21
FEATURE                Location/Qualifiers
source                 1..21
                       mol_type = genomic RNA
                       organism = Homo sapiens
SEQUENCE: 169
aatggcgcca ctagggttgt g                                              21

SEQ ID NO: 170         moltype = RNA   length = 22
FEATURE                Location/Qualifiers
source                 1..22
                       mol_type = genomic RNA
                       organism = Homo sapiens
SEQUENCE: 170
tatgtctgct gaccatcacc tt                                             22

SEQ ID NO: 171         moltype = RNA   length = 22
FEATURE                Location/Qualifiers
source                 1..22
                       mol_type = genomic RNA
                       organism = Homo sapiens
SEQUENCE: 171
tacccattgc atatcggagt tg                                             22

SEQ ID NO: 172         moltype = RNA   length = 24
FEATURE                Location/Qualifiers
source                 1..24
                       mol_type = genomic RNA
                       organism = Homo sapiens
SEQUENCE: 172
actggctagg gaaaatgatt ggat                                           24

SEQ ID NO: 173         moltype = RNA   length = 22
FEATURE                Location/Qualifiers
source                 1..22
                       mol_type = genomic RNA
                       organism = Homo sapiens
SEQUENCE: 173
tgcggggcta gggctaacag ca                                             22

SEQ ID NO: 174         moltype = RNA   length = 22
FEATURE                Location/Qualifiers
source                 1..22
                       mol_type = genomic RNA
                       organism = Homo sapiens
SEQUENCE: 174
tgagacctct gggttctgag ct                                             22

SEQ ID NO: 175         moltype = RNA   length = 23
FEATURE                Location/Qualifiers
source                 1..23
                       mol_type = genomic RNA
                       organism = Homo sapiens
SEQUENCE: 175
cacccggctg tgtgcacatg tgc                                            23

SEQ ID NO: 176         moltype = RNA   length = 22
FEATURE                Location/Qualifiers
source                 1..22
                       mol_type = genomic RNA
                       organism = Homo sapiens
SEQUENCE: 176
tcttctctgt tttggccatg tg                                             22

SEQ ID NO: 177         moltype = RNA   length = 22
FEATURE                Location/Qualifiers
source                 1..22
                       mol_type = genomic RNA
                       organism = Homo sapiens
SEQUENCE: 177
tttccggctc gcgtgggtgt gt                                             22

SEQ ID NO: 178         moltype = RNA   length = 19
FEATURE                Location/Qualifiers
source                 1..19
                       mol_type = genomic RNA
```

-continued

```
                          organism = Homo sapiens
SEQUENCE: 178
aatggattttt tggagcagg                                                    19

SEQ ID NO: 179          moltype = RNA   length = 22
FEATURE                 Location/Qualifiers
source                  1..22
                        mol_type = genomic RNA
                        organism = Homo sapiens
SEQUENCE: 179
tctgggcaac aaagtgagac ct                                                 22

SEQ ID NO: 180          moltype = RNA   length = 24
FEATURE                 Location/Qualifiers
source                  1..24
                        mol_type = genomic RNA
                        organism = Homo sapiens
SEQUENCE: 180
ttgcagctgc ctgggagtga cttc                                               24

SEQ ID NO: 181          moltype = RNA   length = 22
FEATURE                 Location/Qualifiers
source                  1..22
                        mol_type = genomic RNA
                        organism = Homo sapiens
SEQUENCE: 181
actcggcgtg gcgtcggtcg tg                                                 22

SEQ ID NO: 182          moltype = RNA   length = 21
FEATURE                 Location/Qualifiers
source                  1..21
                        mol_type = genomic RNA
                        organism = Homo sapiens
SEQUENCE: 182
tcgaccggac ctcgaccggc t                                                  21

SEQ ID NO: 183          moltype = RNA   length = 21
FEATURE                 Location/Qualifiers
source                  1..21
                        mol_type = genomic RNA
                        organism = Homo sapiens
SEQUENCE: 183
cggcggggac ggcgattggt c                                                  21

SEQ ID NO: 184          moltype = RNA   length = 22
FEATURE                 Location/Qualifiers
source                  1..22
                        mol_type = genomic RNA
                        organism = Homo sapiens
SEQUENCE: 184
ttggggaaac ggccgctgag tg                                                 22

SEQ ID NO: 185          moltype = RNA   length = 22
FEATURE                 Location/Qualifiers
source                  1..22
                        mol_type = genomic RNA
                        organism = Homo sapiens
SEQUENCE: 185
aagggcttcc tctctgcagg ac                                                 22

SEQ ID NO: 186          moltype = RNA   length = 22
FEATURE                 Location/Qualifiers
source                  1..22
                        mol_type = genomic RNA
                        organism = Homo sapiens
SEQUENCE: 186
tgttgtactt ttttttttgt tc                                                 22

SEQ ID NO: 187          moltype = RNA   length = 21
FEATURE                 Location/Qualifiers
source                  1..21
                        mol_type = genomic RNA
                        organism = Homo sapiens
SEQUENCE: 187
tctctcggct cctcgcggct c                                                  21

SEQ ID NO: 188          moltype = RNA   length = 21
FEATURE                 Location/Qualifiers
source                  1..21
```

```
                        mol_type = genomic RNA
                        organism = Homo sapiens
SEQUENCE: 188
caggagtggg gggtgggacg t                                          21

SEQ ID NO: 189         moltype = RNA   length = 17
FEATURE                Location/Qualifiers
source                 1..17
                       mol_type = genomic RNA
                       organism = Homo sapiens
SEQUENCE: 189
ttggaggcgt gggtttt                                               17

SEQ ID NO: 190         moltype = RNA   length = 23
FEATURE                Location/Qualifiers
source                 1..23
                       mol_type = genomic RNA
                       organism = Homo sapiens
SEQUENCE: 190
tgtagagcag ggagcaggaa gct                                        23

SEQ ID NO: 191         moltype = RNA   length = 22
FEATURE                Location/Qualifiers
source                 1..22
                       mol_type = genomic RNA
                       organism = Homo sapiens
SEQUENCE: 191
ttggctggtc tctgctccgc ag                                         22

SEQ ID NO: 192         moltype = RNA   length = 24
FEATURE                Location/Qualifiers
source                 1..24
                       mol_type = genomic RNA
                       organism = Homo sapiens
SEQUENCE: 192
tgaagcgcct gtgctctgcc gaga                                       24
```

CIRCULATING MICRORNA SIGNATURES FOR OVARIAN CANCER

STATEMENT OF RELATED INVENTIONS

This application is a continuation of U.S. patent application Ser. No. 17/456,478, filed Nov. 24, 2021, which is a division of U.S. patent application Ser. No. 16/476,799, filed Jul. 9, 2019, now U.S. Pat. No. 11,214,839, issued on Jan. 4, 2022, which is a national stage entry of PCT Application No. PCT/US2018/012982, filed Jan. 9, 2018, which claims the benefit of U.S. Provisional Patent Application No. 62/444,085, filed Jan. 9, 2017. The entirety of this application is hereby incorporated by reference for all purposes.

REFERENCE TO SEQUENCE LISTING SUBMITTED ELECTRONICALLY

An official copy of the sequence listing is submitted electronically via Patent Center as an xml formatted sequence listing with a file named 731231_DFC-014USDI-VCON_SL.xml, created on Dec. 9, 2022 and having a file size of 169,665 bytes. The Sequence Listing, electronically filed herewith, does not extend beyond the scope of the specification, and does not contain new matter.

STATEMENT REGARDING FEDERALLY SPONSORED RESEARCH OR DEVELOPMENT

This invention was made with Government support under grant number K12HD13015 awarded by the National Institutes of Health. The Government has certain rights in the invention.

BACKGROUND

Ovarian cancer kills more American women annually than any other gynecologic malignancy. The five-year relative survival rate is about 80-92% when diagnosed and treated in an earlier stage (stage I or II), and is about 17-40% when diagnosed and treated in a later stage (stage III or IV). Unfortunately, most ovarian cancers are diagnosed at a later stage due to the lack of an effective screening tool.

The difficulty in developing an effective screening tool is attributed to the low prevalence of ovarian cancer in the general population, which limits the positive predictive value of screening tests. Conventional screening algorithms based on transvaginal ultrasounds tend to diagnose slow-growing benign masses such as endometriomas or non-invasive tumors of low malignant potential (so-called "borderline tumors"), rather than the rapidly proliferating high grade neoplasms which cause nearly all ovarian cancer deaths. CA-125, a conventional biomarker of ovarian cancer, is not accurate enough for ovarian cancer screening in all women because it is affected by many noncancerous conditions. Moreover, epithelial ovarian cancer is not a single biologic entity, but instead describes a heterogeneous set of malignancies that manifest as ovarian masses. This heterogeneity further decreases the sensitivity and specificity in diagnosing ovarian cancer using a single marker.

MicroRNAs (miRNAs) are small regulatory RNA molecules that control gene expression by RNA silencing and post-transcriptional regulation. They are often tissue-specific and are dysregulated in many cancers. MicroRNAs have double-stranded hairpin structures and are more stable than messenger RNAs. Some miRNAs can be detected in the blood and the amounts remain stable in blood samples for years or even decades, providing a practical possibility for using them as biomarkers for noninvasive cancer diagnosis. However, most studies focus on miRNAs aberrantly expressed in tumor samples rather than blood samples. There is a need in the art to identify circulating miRNAs that can amount to accurate and robust diagnosis of early stage ovarian cancer.

SUMMARY

The instant disclosure provides methods for determining the presence or absence and/or the amount of microRNAs in a sample (e.g., blood sample) from a female subject (e.g., human subject), as well as kits comprising probes to micro RNAs. The instant disclosure also describes methods for treating a female subject, as well as methods for screening blood samples of female subjects for the presence or absence of certain microRNAs.

In one aspect, the instant disclosure provides a method for determining the presence or absence and/or amounts of microRNAs in a sample from a female subject (e.g., human subject). In some embodiments, the method comprises: (a) obtaining a sample collected from the subject; and (b) determining the presence or absence and/or amounts of one or more (e.g., two or more, three or more, four or more, five or more, or six or more) test microRNAs selected from the group consisting of: hsa-miR-29a-3p (SEQ ID NO: 39); hsa-miR-92a-3p (SEQ ID NO: 47); hsa-miR-200c-3p (SEQ ID NO: 105); hsa-miR-320c (SEQ ID NO: 115); hsa-miR-335-5p (SEQ ID NO: 122); hsa-miR-450b-5p (SEQ ID NO: 149); and hsa-miR-1307-5p (SEQ ID NO: 182) in the sample, thereby determining the presence or absence and/or amounts of the microRNAs in the sample. In some embodiments, step (b) comprises determining the presence or absence and/or amounts of seven test microRNAs of: hsa-miR-29a-3p (SEQ ID NO: 39); hsa-miR-92a-3p (SEQ ID NO: 47); hsa-miR-200c-3p (SEQ ID NO: 105); hsa-miR-320c (SEQ ID NO: 115); hsa-miR-335-5p (SEQ ID NO: 122); hsa-miR-450b-5p (SEQ ID NO: 149); and hsa-miR-1307-5p (SEQ ID NO: 182) in the sample. In some embodiments, the presence or absence and/or amounts of no more than 2,500 (e.g., no more than 30, 40, 50, 60, 70, 80, 90, 100, 110, 120, 130, 140, 150, 160, 170, 180, 190, 200, 250, 300, 400, 500, 600, 700, 800, 900, 1,000, 1,500, or 2,000) test microRNAs are determined. In some embodiments, step (b) consists of determining the presence or absence and/or amounts of seven test microRNAs of: hsa-miR-29a-3p (SEQ ID NO: 39); hsa-miR-92a-3p (SEQ ID NO: 47); hsa-miR-200c-3p (SEQ ID NO: 105); hsa-miR-320c (SEQ ID NO: 115); hsa-miR-335-5p (SEQ ID NO: 122); hsa-miR-450b-5p (SEQ ID NO: 149); and hsa-miR-1307-5p (SEQ ID NO: 182) in the sample.

In another aspect, the instant disclosure provides a method for diagnosing ovarian cancer in a female subject (e.g., human subject), the method comprising: (a) obtaining a sample collected from the subject; (b) determining the amounts of one or more (e.g., two or more, three or more, four or more, five or more, or six or more) test microRNAs selected from the group consisting of hsa-miR-29a-3p (SEQ ID NO: 39), hsa-miR-92a-3p (SEQ ID NO: 47), hsa-miR-200c-3p (SEQ ID NO: 105), hsa-miR-320c (SEQ ID NO: 115), hsa-miR-335-5p (SEQ ID NO: 122), hsa-miR-450b-5p (SEQ ID NO: 149), and hsa-miR-1307-5p (SEQ ID NO: 182) in the sample; and (c) comparing the amounts of the test microRNAs determined in step (b) to a statistical model, thereby diagnosing ovarian cancer in the subject. In some embodiments, step (b) comprises determining the amounts of seven test microRNAs of: hsa-miR-29a-3p (SEQ ID NO: 39), hsa-miR-92a-3p (SEQ ID NO: 47), hsa-miR-200c-3p (SEQ ID NO: 105), hsa-miR-320c (SEQ ID NO: 115), hsa-miR-335-5p (SEQ ID NO: 122), hsa-miR-450b-5p (SEQ ID NO: 149), and hsa-miR-1307-5p (SEQ ID NO: 182) in the sample. In some embodiments, the presence or absence and/or amounts of no more than 2,500 (e.g., no more than 30, 40, 50, 60, 70, 80, 90, 100, 110, 120, 130, 140, 150, 160, 170, 180, 190, 200, 250, 300, 400, 500, 600, 700, 800, 900, 1,000, 1,500, or 2,000) test microRNAs are determined. In some embodiments, step (b) consists of determining the presence or absence and/or amounts of seven test microRNAs of: hsa-miR-29a-3p (SEQ ID NO: 39); hsa-miR-92a-3p (SEQ ID NO: 47); hsa-miR-200c-3p (SEQ ID NO: 105); hsa-miR-320c (SEQ ID NO: 115); hsa-miR-335-5p (SEQ ID NO: 122); hsa-miR-450b-5p (SEQ ID NO: 149); and hsa-miR-1307-5p (SEQ ID NO: 182) in the sample.

In some embodiments, step (b) of a method disclosed herein further comprises determining the presence or absence and/or amounts of one or more (e.g., two or more, three or more, four or more, five or more, or six or more) additional test microRNAs selected from the group consisting of: hsa-miR-23b-3p (SEQ ID NO: 29); hsa-miR-32-5p (SEQ ID NO: 46); hsa-miR-150-5p (SEQ ID NO: 83); hsa-miR-200a-3p (SEQ ID NO: 104); hsa-miR-203a (SEQ ID NO: 106); hsa-miR-320d (SEQ ID NO: 116); and hsa-miR-1246 (SEQ ID NO: 178) in the sample. In some embodiments, step (b) of a method disclosed herein further comprises determining the presence or absence and/or amounts of seven additional test microRNAs of: hsa-miR-23b-3p (SEQ ID NO: 29); hsa-miR-32-5p (SEQ ID NO: 46); hsa-miR-150-5p (SEQ ID NO: 83); hsa-miR-200a-3p (SEQ ID NO: 104); hsa-miR-203a (SEQ ID NO: 106); hsa-miR-320d (SEQ ID NO: 116); and hsa-miR-1246 (SEQ ID NO: 178) in the sample. In some embodiments, the presence or absence and/or amounts of no more than 2,500 (e.g., no more than 30, 40, 50, 60, 70, 80, 90, 100, 110, 120, 130, 140, 150, 160, 170, 180, 190, 200, 250, 300, 400, 500, 600, 700, 800, 900, 1,000, 1,500, or 2,000) test microRNAs are determined.

In some embodiments, step (b) comprises determining the presence or absence and/or amounts of fourteen test microRNAs of hsa-miR-29a-3p (SEQ ID NO: 39), hsa-miR-92a-3p (SEQ ID NO: 47), hsa-miR-200c-3p (SEQ ID NO: 105), hsa-miR-320c (SEQ ID NO: 115), hsa-miR-335-5p (SEQ ID NO: 122), hsa-miR-450b-5p (SEQ ID NO: 149), hsa-miR-1307-5p (SEQ ID NO: 182), hsa-miR-23b-3p (SEQ ID NO: 29), hsa-miR-32-5p (SEQ ID NO: 46), hsa-miR-150-5p (SEQ ID NO: 83), hsa-miR-200a-3p (SEQ ID NO: 104), hsa-miR-203a (SEQ ID NO: 106), hsa-miR-320d (SEQ ID NO: 116), and hsa-miR-1246 (SEQ ID NO: 178) in the sample. In some embodiments, the presence or absence and/or amounts of no more than 2,500 (e.g., no more than 30, 40, 50, 60, 70, 80, 90, 100, 110, 120, 130, 140, 150, 160, 170, 180, 190, 200, 250, 300, 400, 500, 600, 700, 800, 900, 1,000, 1,500, or 2,000) test microRNAs are determined. In some embodiments, step (b) consists of determining the presence or absence and/or amounts of fourteen test microRNAs of hsa-miR-29a-3p (SEQ ID NO: 39), hsa-miR-92a-3p (SEQ ID NO: 47), hsa-miR-200c-3p (SEQ ID NO: 105), hsa-miR-320c (SEQ ID NO: 115), hsa-miR-335-5p (SEQ ID NO: 122), hsa-miR-450b-5p (SEQ ID NO: 149), hsa-miR-1307-5p (SEQ ID NO: 182), hsa-miR-23b-3p (SEQ ID NO: 29), hsa-miR-32-5p (SEQ ID NO: 46), hsa-miR-150-5p (SEQ ID NO: 83), hsa-miR-200a-3p (SEQ ID NO: 104), hsa-miR-203a (SEQ ID NO: 106), hsa-miR-320d (SEQ ID NO: 116), and hsa-miR-1246 (SEQ ID NO: 178) in the sample.

In some embodiments, step (b) of a method disclosed herein comprises determining the presence or absence and/or amounts of the fourteen test microRNAs of: hsa-miR-29a-3p (SEQ ID NO: 39); hsa-miR-92a-3p (SEQ ID NO: 47); hsa-miR-200c-3p (SEQ ID NO: 105); hsa-miR-320c (SEQ ID NO: 115); hsa-miR-335-5p (SEQ ID NO: 122); hsa-miR-450b-5p (SEQ ID NO: 149); hsa-miR-1307-5p (SEQ ID NO: 182); hsa-miR-23b-3p (SEQ ID NO: 29); hsa-miR-32-5p (SEQ ID NO: 46); hsa-miR-150-5p (SEQ ID NO: 83); hsa-miR-200a-3p (SEQ ID NO: 104); hsa-miR-203a (SEQ ID NO: 106); hsa-miR-320d (SEQ ID NO: 116); and hsa-miR-1246 (SEQ ID NO: 178) in the sample. In some embodiments, the presence or absence and/or amounts of only these fourteen test microRNAs are determined.

In some embodiments, the method disclosed herein further comprises the step of: (d) determining the presence or absence and/or amounts of one or more (e.g., two, three, four, two or more, three or more, four or more) normalizing microRNAs in the sample. In some embodiments, the method disclosed herein further comprises the step of (e) normalizing the determined presence or absence and/or amounts of the test microRNAs using the presence or absence and/or amounts of the normalizing microRNAs determined in step (d). In some embodiments, the normalizing microRNAs are selected from the group consisting of hsa-miR-103a-3p (SEQ ID NO: 55), hsa-miR-221-3p (SEQ ID NO: 108), hsa-miR-423-3p (SEQ ID NO: 142), and hsa-miR-191-5p (SEQ ID NO: 196). In some embodiments, step (d) comprises determining the presence or absence and/or amounts of four normalizing microRNAs of hsa-miR-103a-3p (SEQ ID NO: 55), hsa-miR-221-3p (SEQ ID NO: 108), hsa-miR-423-3p (SEQ ID NO: 142), and hsa-miR-191-5p (SEQ ID NO: 196) in the sample. In some embodiments, step (d) consists of determining the presence or absence and/or amounts of four normalizing microRNAs of hsa-miR-103a-3p (SEQ ID NO: 55), hsa-miR-221-3p (SEQ ID NO: 108), hsa-miR-423-3p (SEQ ID NO: 142), and hsa-miR-191-5p (SEQ ID NO: 196) in the sample. In some embodiments, step (d) comprises determining the presence or absence and/or amounts of two normalizing microRNAs of hsa-miR-103a-3p (SEQ ID NO: 55) and hsa-miR-423-3p (SEQ ID NO: 142) in the sample. In some embodiments, step (d) consists of determining the presence or absence and/or amounts of two normalizing microRNAs of hsa-miR-103a-3p (SEQ ID NO: 55) and hsa-miR-423-3p (SEQ ID NO: 142) in the sample. In some embodiments, the presence or absence and/or amounts of no more than 2,500 (e.g., no more than 30, 40, 50, 60, 70, 80, 90, 100, 110, 120, 130, 140, 150, 160, 170, 180, 190, 200, 250, 300, 400, 500, 600, 700, 800, 900, 1,000, 1,500, or 2,000) normalizing microRNAs are determined. In some embodiments, the presence or absence and/or amounts of no normalizing microRNAs are determined in step (d).

The determined presence or absence and/or amounts of the normalizing microRNAs can be used to normalize the determined presence or absence and/or amounts of any test microRNAs. In some embodiments, the determined presence or absence and/or amounts of the normalizing microRNAs are used to normalize the determined presence or absence and/or amounts of the seven microRNAs of hsa-miR-29a-3p (SEQ ID NO: 39); hsa-miR-92a-3p (SEQ ID NO: 47); hsa-miR-200c-3p (SEQ ID NO: 105); hsa-miR-320c (SEQ ID NO: 115); hsa-miR-335-5p (SEQ ID NO: 122); hsa-miR-450b-5p (SEQ ID NO: 149); and hsa-miR- 1307-5p (SEQ ID NO: 182). In some embodiments, steps (b) and (d) in a method disclosed herein comprises determining the presence or absence and/or amounts of these seven test microRNAs and the four normalizing microRNAs of hsa-miR-103a-3p (SEQ ID NO: 55), hsa-miR-221-3p (SEQ ID NO: 108), hsa-miR-423-3p (SEQ ID NO: 142), and hsa-miR-191-5p (SEQ ID NO: 196). In some embodiments, steps (b) and (d) in a method disclosed herein consists of determining the presence or absence and/or amounts of these seven test microRNAs and the four normalizing microRNAs of hsa-miR-103a-3p (SEQ ID NO: 55), hsa-miR-221-3p (SEQ ID NO: 108), hsa-miR-423-3p (SEQ ID NO: 142), and hsa-miR-191-5p (SEQ ID NO: 196). In some embodiments, steps (b) and (d) in a method disclosed herein comprises determining the presence or absence and/or amounts of these seven test microRNAs and the two normalizing microRNAs of hsa-miR-423-3p (SEQ ID NO: 142) and hsa-miR-103a-3p (SEQ ID NO: 55). In some embodiments, steps (b) and (d) in a method disclosed herein consists of determining the presence or absence and/or amounts of these seven test microRNAs and the two normalizing microRNAs of hsa-miR-423-3p (SEQ ID NO: 142) and hsa-miR-103a-3p (SEQ ID NO: 55).

In some embodiments, the determined presence or absence and/or amounts of the normalizing microRNAs are used to normalize the determined presence or absence and/or amounts of the fourteen test microRNAs of: hsa-miR-29a-3p (SEQ ID NO: 39); hsa-miR-92a-3p (SEQ ID NO: 47); hsa-miR-200c-3p (SEQ ID NO: 105); hsa-miR-320c (SEQ ID NO: 115); hsa-miR-335-5p (SEQ ID NO: 122); hsa-miR-450b-5p (SEQ ID NO: 149); hsa-miR-1307-5p (SEQ ID NO: 182); hsa-miR-23b-3p (SEQ ID NO: 29); hsa-miR-32-5p (SEQ ID NO: 46); hsa-miR-150-5p (SEQ ID NO: 83); hsa-miR-200a-3p (SEQ ID NO: 104); hsa-miR-203a (SEQ ID NO: 106); hsa-miR-320d (SEQ ID NO: 116); and hsa-miR-1246 (SEQ ID NO: 178). In some embodiments, steps (b) and (d) in a method disclosed herein comprises determining the presence or absence and/or amounts of these fourteen test microRNAs and the two normalizing microRNAs of hsa-miR-423-3p (SEQ ID NO: 142) and hsa-miR-103a-3p (SEQ ID NO: 55). In some embodiments, steps (b) and (d) in a method disclosed herein consists of determining the presence or absence and/or amounts of these fourteen test microRNAs and the two normalizing microRNAs of hsa-miR-423-3p (SEQ ID NO: 142) and hsa-miR-103a-3p (SEQ ID NO: 55). In some embodiments, steps (b) and (d) in a method disclosed herein comprises determining the presence or absence and/or amounts of these fourteen test microRNAs and the four normalizing microRNAs of: hsa-miR-103a-3p (SEQ ID NO: 55), hsa-miR-221-3p (SEQ ID NO: 108), hsa-miR-423-3p (SEQ ID NO: 142), and hsa-miR-191-5p (SEQ ID NO: 196). In some embodiments, steps (b) and (d) in a method disclosed herein consists of determining the presence or absence and/or amounts of these fourteen test microRNAs and the four normalizing microRNAs of: hsa-miR-103a-3p (SEQ ID NO: 55), hsa-miR-221-3p (SEQ ID NO: 108), hsa-miR-423-3p (SEQ ID NO: 142), and hsa-miR-191-5p (SEQ ID NO: 196). With the amounts of these fourteen microRNAs, the amounts of normalizing microRNAs are dispensable. Accordingly, in some embodiments, steps (b) and (d) in a method disclosed herein consists of determining the presence or absence and/or amounts of these fourteen test microRNAs and no normalizing microRNAs.

In another aspect, the instant disclosure provides a method for determining the presence or absence and/or amounts of microRNAs in a blood sample from a subject (e.g., human subject), the method comprising: (a) obtaining a blood sample collected from the subject; and (b) determining the presence or absence and/or amounts of one or more of the microRNAs listed in Table 2 in the sample, thereby determining the presence or absence and/or amounts of the microRNAs in the sample. In some embodiments, step (b) comprises determining the presence or absence and/or amounts of at least 1 (e.g., at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, or 190) of the microRNAs listed in Table 2 in the sample. In some embodiments, step (b) comprises determining the presence or absence and/or amounts of no more than 190 (e.g., no more than 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, or 180) of the microRNAs listed in Table 2 in the sample. In some embodiments, step (b) consists of determining the presence or absence and/or amounts of the 192 microRNAs listed in Table 2 in the sample.

Any one of the foregoing methods (e.g., methods for diagnosing ovarian cancer, or methods for determining the presence or absence and/or amounts of microRNAs) can be used to diagnose ovarian cancer at any stage, and is particularly advantageous in the ability to diagnose early-stage ovarian cancer. Accordingly, in some embodiments, the ovarian cancer diagnosed is a stage I (e.g., stage IA, stage IB, stage IC, stage IC1, stage IC2, or stage IC3) ovarian cancer. In some embodiments, the ovarian cancer diagnosed is a stage II (e.g., stage IIA or stage IIB) ovarian cancer. In some embodiments, the ovarian cancer diagnosed is a stage III (e.g., stage IIIA, IIIA1(i), IIIA1(ii), IIIA2, IIIB, or IIIC) ovarian cancer. In some embodiments, the ovarian cancer diagnosed is a stage IV (e.g., stage IVA or stage IVB) ovarian cancer. In some embodiments, the ovarian cancer diagnosed of the female subject is an invasive serous adenocarcinoma, an invasive clear cell adenocarcinoma, or an invasive endometrioid adenocarcinoma.

In another aspect, the instant disclosure provides a method for treating a female subject suspected of having ovarian cancer, the method comprising the steps of any one of the foregoing methods (e.g., methods for diagnosing ovarian cancer, or methods for determining the presence or absence and/or amounts of microRNAs); and treating the subject for ovarian cancer or monitoring the subject for ovarian cancer, based on the presence or absence and/or amounts of microRNAs determined in steps (b) and/or (d), and/or the comparison of step (c). In some embodiments, treating the subject is performed using one or more treatments selected from the group consisting of: surgery, chemotherapy, targeted antibody therapy, radiation therapy, and hormone therapy, and stem cell transplant.

In yet another aspect, the disclosure provides methods for screening a female subject for the presence or absence and/or amounts of microRNAs, the method comprising the steps of any one of the foregoing methods (e.g., methods for diagnosing ovarian cancer, or methods for determining the presence or absence and/or amounts of microRNAs). In some embodiments, the screening method further comprises the step of determining the presence or absence and/or amounts of the same microRNAs in a second sample. In some embodiments, the second sample is a second sample from the same subject, a sample of the same tissue or organ from a different subject known to have ovarian cancer, or a sample of the same tissue or organ from a different subject known not to have ovarian cancer.

In some embodiments of any one of the preceding aspects, step (b) and/or step (d) are performed by detecting binding of the sample to at least one probe capable of specifically hybridizing to each of the microRNAs or a complementary DNA (cDNA) thereof. In some embodiments, step (b) and/or step (d) are performed by detecting binding of the sample to at least two probes capable of specifically hybridizing to each of the microRNAs or a cDNA thereof. In some embodiments, step (b) and/or step (d) are performed using a nucleic acid detection assay, e.g., microarray, reverse-transcription (RT)-PCR, and reverse-transcription quantitative PCR (RT-qPCR). In some embodiments, at least one of the probes comprises a detectable label. The detectable label can be a non-natural label that permits detection of a microRNA in a sample, such as fluorescent label, a fluorescence donor, a fluorescence quencher, or any other non-natural molecule that may be used to detect the nucleic acid polymer or detect the hybridization of the nucleic acid polymer with the microRNA. In some embodiments, each one of the probes comprises a detectable label. In some embodiments, step (b) and/or step (d) are performed by reverse-transcribing the microRNA molecules in the sample, thereby obtain a cDNA sample; and sequencing the cDNA sample. In some embodiments, step (b) and/or step (d) further comprises amplifying the DNA molecules in the cDNA sample before sequencing the cDNA sample. In some embodiments, the sequencing is performed by next-generation sequencing.

In some embodiments of any one of the preceding aspects, the sample is selected from a sample of blood, lymph node, or ovary. In some embodiments, the sample is a blood sample, e.g., plasma, serum, or whole blood. In some embodiments, the sample is a sample of lymph node, e.g., a draining lymph node for an ovary. In some embodiments, the sample is an ovary sample, e.g., an ovary suspected to contain a tumor.

In some embodiments of any one of the preceding aspects, the female subject is at the risk of developing ovarian cancer. Certain factors may increase a subject's risk of ovarian cancer. For example, ovarian cancer rates are highest in women aged 55-64 years. Half of all ovarian cancers are found in women 63 years of age or older (the median age of diagnosis). Family history of ovarian cancer, colorectal cancer (such as mutations in the gene MUTYH), and/or breast cancer also increases the risk of ovarian cancer in a subject. Mutations in the genes BRCA1 and BRCA2 are associated with increased risk of ovarian cancer. Increased ovarian cancer risk is also seen in Lynch syndrome, characterized by germline mutations in DNA mismatch repair (MMR) genes, including mutL homolog 1 (MLH1), mutS homolog 2 (MSH2), MSH3, MSH6, postmeiotic segregation increased 1 (PMS1), and PMS2 (see Nakamura et al., Mol Clin Oncol. 2014 November; 2(6): 909-916). Accumulated mutations in PTEN also increase the risk of ovarian cancer (see Merritt and Cramer, Cancer Biomark. 2010; 9(1-6):287-305.). Female subjects with Peutz-Jeghers syndrome, an inherited genetic variant of the gene STK11, also have an increases risk of ovarian cancer. Accordingly, in some embodiments, the subject has any one of the foregoing risk factors for ovarian cancer. In some embodiments, the subject has one or more ovaries. In some embodiments, the subject has at least one mutation in the BRCA1 or BRCA2 gene. In some embodiments, the subject has at least one mutation in the MMR genes. In some embodiments, the subject is at least 55 years (e.g., at least 56, 57, 58, 59, 60, 61, 62, 63, 64, or 65 years) of age. In some embodiments, the subject is no more than 65 years (e.g., no more than 55, 56, 57, 58, 59, 60, 61, 62, 63, or 64 years) of age.

In some embodiments, the subject has been suspected of having ovarian cancer. In some embodiments, the subject has been diagnosed of having ovarian cancer, and the method disclosed herein is used to at least confirm the diagnosis. Methods of diagnosing ovarian cancer include without limitation physical examination, ultrasound imaging, computed tomography scan, magnetic resonance imaging (MRI) scan, positron emission tomography (PET) scan, and blood tests. In some embodiments, the blood test is determines the level of CA-125, wherein the subject has a higher level of CA-125 antigen in the blood than a diagnostic threshold level (e.g., 35 U/mL).

The statistical model used in the methods disclosed herein can be any statistical models known in the art. In some embodiments, the statistical model comprises one or more models selected from the group consisting of linear discriminant analysis, logistic regression, multivariate adaptive regression splines, naive Bayes, neural network, support vector machine, functional tree, LAD tree, Bayesian network, elastic net regression, and random forest. In some embodiments, the statistical model comprises a neural network, optionally further comprising one or more other statistical models. In some embodiments, the statistical model consists of a neural network.

In another aspect, the disclosure provides a kit comprising at least one test probe capable of specifically hybridizing to a microRNAs selected from the group consisting of: hsa-miR-92a-3p (SEQ ID NO: 47), hsa-miR-450b-5p (SEQ ID NO: 149), hsa-miR-335-5p (SEQ ID NO: 122), hsa-miR-29a-3p (SEQ ID NO: 39), hsa-miR-1307-5p (SEQ ID NO: 182), hsa-miR-320c (SEQ ID NO: 115), and hsa-miR-200c-3p (SEQ ID NO: 105), or a cDNA thereof. In some embodiments, the kit comprises at least one test probe (e.g., at least two test probes) capable of specifically hybridizing to each of the microRNAs selected from the group consisting of hsa-miR-92a-3p (SEQ ID NO: 47), hsa-miR-450b-5p (SEQ ID NO: 149), hsa-miR-335-5p (SEQ ID NO: 122), hsa-miR-29a-3p (SEQ ID NO: 39), hsa-miR-1307-5p (SEQ ID NO: 182), hsa-miR-320c (SEQ ID NO: 115), and hsa-miR-200c-3p (SEQ ID NO: 105), or a cDNA thereof. In some embodiments, the test probes consist of seven probes to test microRNAs with one test probe capable of specifically hybridizing to each of the microRNAs selected from the group consisting of hsa-miR-92a-3p (SEQ ID NO: 47), hsa-miR-450b-5p (SEQ ID NO: 149), hsa-miR-335-5p (SEQ ID NO: 122), hsa-miR-29a-3p (SEQ ID NO: 39), hsa-miR-1307-5p (SEQ ID NO: 182), hsa-miR-320c (SEQ ID NO: 115), and hsa-miR-200c-3p (SEQ ID NO: 105), or a cDNA thereof. In some embodiments, the test probes consist of fourteen probes to test microRNAs with two test probes capable of specifically hybridizing to each of the microRNAs selected from the group consisting of hsa-miR-92a-3p (SEQ ID NO: 47), hsa-miR-450b-5p (SEQ ID NO: 149), hsa-miR-335-5p (SEQ ID NO: 122), hsa-miR-29a-3p (SEQ ID NO: 39), hsa-miR-1307-5p (SEQ ID NO: 182), hsa-miR-320c (SEQ ID NO: 115), and hsa-miR-200c-3p (SEQ ID NO: 105), or a cDNA thereof.

In some embodiments of the kits disclosed herein, the kit further comprises at least one additional test probe capable of hybridizing to a microRNA selected from the group consisting of: hsa-miR-23b-3p (SEQ ID NO: 29); hsa-miR-32-5p (SEQ ID NO: 46); hsa-miR-150-5p (SEQ ID NO: 83); hsa-miR-200a-3p (SEQ ID NO: 104); hsa-miR-203a (SEQ ID NO: 106); hsa-miR-320d (SEQ ID NO: 116); and hsa-miR-1246 (SEQ ID NO: 178), or a cDNA thereof. In some embodiments, the kit further comprises at least one test probe (e.g., at least two test probes) capable of hybridizing to each of the microRNAs selected from the group consisting of hsa-miR-23b-3p (SEQ ID NO: 29), hsa-miR-32-5p (SEQ ID NO: 46), hsa-miR-150-5p (SEQ ID NO: 83), hsa-miR-200a-3p (SEQ ID NO: 104), hsa-miR203a (SEQ ID NO: 106), hsa-miR-320d (SEQ ID NO: 116), and hsa-miR1246 (SEQ ID NO: 178), or a cDNA thereof.

In some embodiments, the kit comprises at least one test probe (e.g., at least two test probes) capable of specifically hybridizing to each of the microRNAs selected from the group consisting of hsa-miR-92a-3p (SEQ ID NO: 47), hsa-miR-450b-5p (SEQ ID NO: 149), hsa-miR-335-5p (SEQ ID NO: 122), hsa-miR-29a-3p (SEQ ID NO: 39), hsa-miR-1307-5p (SEQ ID NO: 182), hsa-miR-320c (SEQ ID NO: 115), hsa-miR-200c-3p (SEQ ID NO: 105), hsa-miR-23b-3p (SEQ ID NO: 29), hsa-miR-32-5p (SEQ ID NO: 46), hsa-miR-150-5p (SEQ ID NO: 83), hsa-miR-200a-3p (SEQ ID NO: 104), hsa-miR203a (SEQ ID NO: 106), hsa-miR-320d (SEQ ID NO: 116), and hsa-miR1246 (SEQ ID NO: 178), or a cDNA thereof. In some embodiments, the test probes consist of fourteen probes to test microRNAs with one test probe capable of specifically hybridizing to each of the microRNAs selected from the group consisting of hsa-miR-92a-3p (SEQ ID NO: 47), hsa-miR-450b-5p (SEQ ID NO: 149), hsa-miR-335-5p (SEQ ID NO: 122), hsa-miR-29a-3p (SEQ ID NO: 39), hsa-miR-1307-5p (SEQ ID NO: 182), hsa-miR-320c (SEQ ID NO: 115), hsa-miR-200c-3p (SEQ ID NO: 105), hsa-miR-23b-3p (SEQ ID NO: 29), hsa-miR-32-5p (SEQ ID NO: 46), hsa-miR-150-5p (SEQ ID NO: 83), hsa-miR-200a-3p (SEQ ID NO: 104), hsa-miR203a (SEQ ID NO: 106), hsa-miR-320d (SEQ ID NO: 116), and hsa-miR1246 (SEQ ID NO: 178), or a cDNA thereof. In some embodiments, the test probes consist of 28 probes to test microRNAs with two test probes capable of specifically hybridizing to each of the microRNAs selected from the group consisting of hsa-miR-92a-3p (SEQ ID NO: 47), hsa-miR-450b-5p (SEQ ID NO: 149), hsa-miR-335-5p (SEQ ID NO: 122), hsa-miR-29a-3p (SEQ ID NO: 39), hsa-miR-1307-5p (SEQ ID NO: 182), hsa-miR-320c (SEQ ID NO: 115), hsa-miR-200c-3p (SEQ ID NO: 105), hsa-miR-23b-3p (SEQ ID NO: 29), hsa-miR-32-5p (SEQ ID NO: 46), hsa-miR-150-5p (SEQ ID NO: 83), hsa-miR-200a-3p (SEQ ID NO: 104), hsa-miR203a (SEQ ID NO: 106), hsa-miR-320d (SEQ ID NO: 116), and hsa-miR1246 (SEQ ID NO: 178), or a cDNA thereof. In some embodiments, the kit comprises no normalizing probes.

In some embodiments, the kit further comprises at least one normalizing probe capable of hybridizing to a microRNA selected from the group consisting of hsa-miR-103a-3p (SEQ ID NO: 55), hsa-miR-221-3p (SEQ ID NO: 108), hsa-miR-423-3p (SEQ ID NO: 142), and hsa-miR-191-5p (SEQ ID NO: 196), or a cDNA thereof. In some embodiments, the kit further comprises at least one normalizing probe (e.g., at least two normalizing probes) capable of hybridizing to each of the microRNAs selected from the group consisting of hsa-miR-103a-3p (SEQ ID NO: 55), hsa-miR-221-3p (SEQ ID NO: 108), hsa-miR-423-3p (SEQ ID NO: 142), and hsa-miR-191-5p (SEQ ID NO: 196), or a cDNA thereof. In some embodiments, the kit further comprises at least one normalizing probe (e.g., at least two normalizing probes) capable of hybridizing to each of the microRNAs selected from the group consisting of hsa-miR-423-3p (SEQ ID NO: 142) and hsa-miR-103a-3p (SEQ ID NO: 55). In some embodiments, the normalizing probes consist of four probes to normalizing microRNAs with one normalizing probe capable of specifically hybridizing to each of the microRNAs selected from the group consisting of hsa-miR-103a-3p (SEQ ID NO: 55), hsa-miR-221-3p (SEQ ID NO: 108), hsa-miR-423-3p (SEQ ID NO: 142), and hsa-miR-191-5p (SEQ ID NO: 196), or a cDNA thereof. In some embodiments, the normalizing probes consist of eight probes to normalizing microRNAs with two test probes capable of specifically hybridizing to each of the microRNAs selected from the group consisting of hsa-miR-103a-3p (SEQ ID NO: 55), hsa-miR-221-3p (SEQ ID NO: 108), hsa-miR-423-3p (SEQ ID NO: 142), and hsa-miR-191-5p (SEQ ID NO: 196), or a cDNA thereof. In some embodiments, the kit comprises no normalizing probes.

In some embodiments, the kit comprises at least one test probe (e.g., at least two test probes) capable of specifically hybridizing to each of the microRNAs selected from the group consisting of hsa-miR-92a-3p (SEQ ID NO: 47), hsa-miR-450b-5p (SEQ ID NO: 149), hsa-miR-335-5p (SEQ ID NO: 122), hsa-miR-29a-3p (SEQ ID NO: 39), hsa-miR-1307-5p (SEQ ID NO: 182), hsa-miR-320c (SEQ ID NO: 115), and hsa-miR-200c-3p (SEQ ID NO: 105), or a cDNA thereof, and at least one normalizing probe (e.g., at least two normalizing probes) capable of hybridizing to each of the microRNAs selected from the group consisting of hsa-miR-103a-3p (SEQ ID NO: 55), hsa-miR-221-3p (SEQ ID NO: 108), hsa-miR-423-3p (SEQ ID NO: 142), and hsa-miR-191-5p (SEQ ID NO: 196), or a cDNA thereof. In some embodiments, the probes consist of eleven probes to microRNAs with one probe capable of specifically hybridizing to each of the microRNAs or a cDNA thereof. In some embodiments, the test probes consist of 22 probes to microRNAs with two probes capable of specifically hybridizing to each of the microRNAs or a cDNA thereof.

In some embodiments of any of the kits disclosed herein, at least one of the probes comprises a detectable label. The detectable label can be a non-natural label that permits detection of a microRNA in a sample, such as fluorescent label, a fluorescence donor, a fluorescence quencher, or any other non-natural molecule that may be used to detect the nucleic acid polymer or detect the hybridization of the nucleic acid polymer with the microRNA. In some embodiments, each one of the probes comprises a detectable label.

In certain embodiment, the kit further comprises one or more reagents suitable for the determination of the presence or absence and/or amounts of microRNAs (e.g., buffers) and instructions for use. The kit may also include reagents for amplification of a nucleic acid sequence, such as a DNA sequence or an RNA sequence. In some embodiments, reagents may include: a heat-stable DNA polymerase; deoxynucleotide triphosphates (dNTPs); a buffer solution to provide a suitable chemical environment for optimum activity, binding kinetics, and stability of the DNA polymerase; bivalent cations such as magnesium or manganese ions; and/or monovalent cations, such as potassium ions. In some embodiments, such reagents may include: a reverse transcriptase; an RNase inhibitor; a primer that hybridizes to a nucleic acid sequence (such as RNA or DNA); a primer that hybridizes to an adenosine oligonucleotide; and a buffer solution that provides a suitable chemical environment for optimum activity, binding kinetics, and stability of the reverse transcriptase. In some embodiments, the kit further comprises standard samples of one or more of the microRNAs capable of hybridizing to the probes. The reagents for amplification of the nucleic acid sequence may be provided in the form of a solution, a concentrated solution, or a powder. In some embodiments, the kit further comprises one or more reagents suitable of extracting and/or purifying microRNA molecules from a samples (e.g., blood sample).

In certain embodiments, kits of the instant disclosure may also include instructions describing the use of the kit for determining the presence or absence and/or amounts of the test microRNAs in a sample (e.g., blood sample). In some embodiments, the kit further comprises access to a computer program to make diagnosis based on the presence or absence and/or amounts of the test microRNAs and/or normalizing microRNAs in a sample. In certain embodiments, the instructions are provided as an insert sheet. In certain embodiments, the instructions are provided as a computer-readable form carried on a device or transmitted or obtainable from a location on the Internet.

DETAILED DESCRIPTION

Figure 1A:
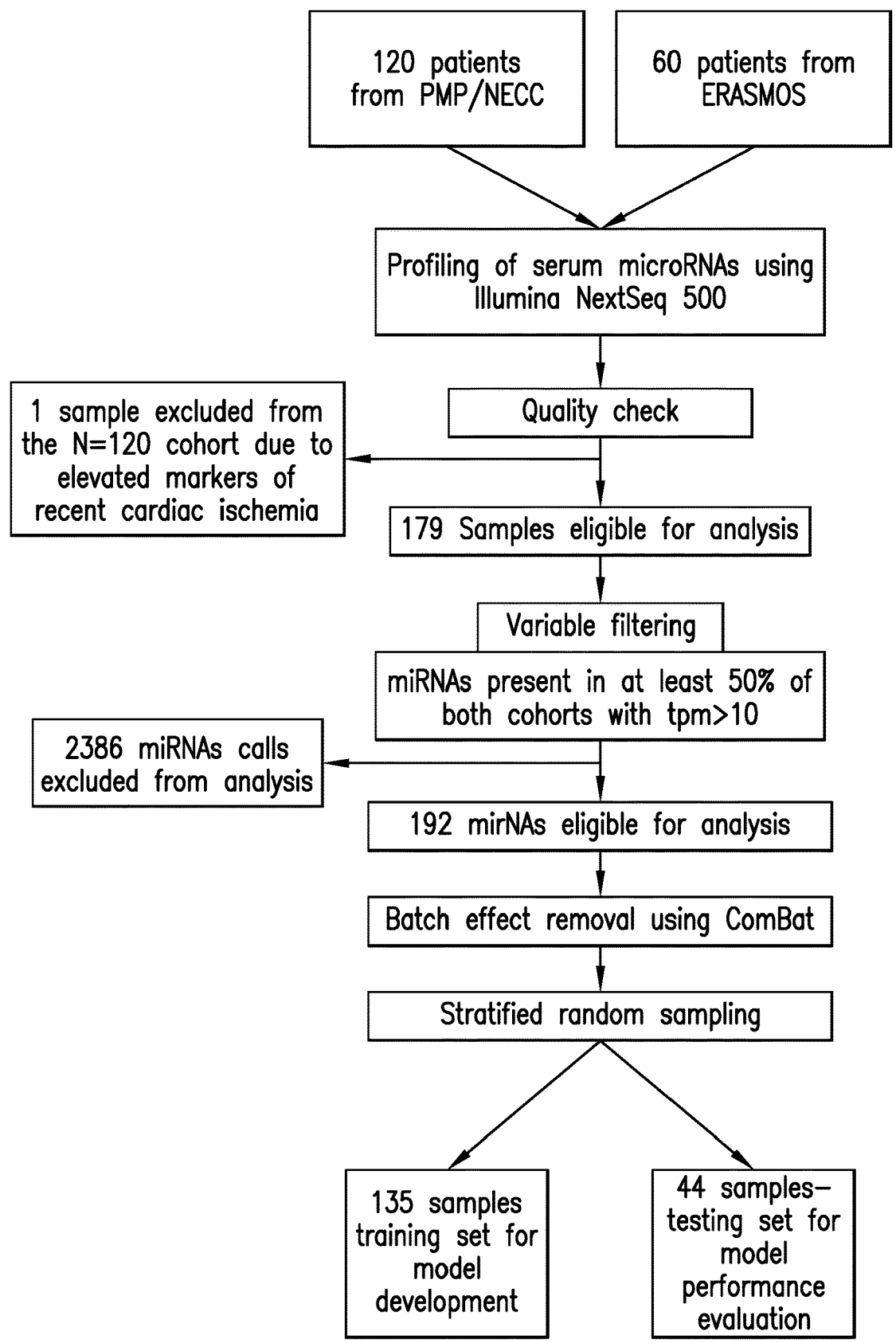
FIG. 1A shows a flow chart of the protocol for miRNA sequencing, filtering, batch adjustment and separation into the training and testing sets.

It is to be understood that the methods described in this disclosure are not limited to particular methods and experimental conditions disclosed herein; as such methods and conditions may vary. It is also to be understood that the terminology used herein is for the purpose of describing particular embodiments only, and is not intended to be limiting.

Furthermore, the experiments described herein, unless otherwise indicated, use conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2$^{nd}$ edition).

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

Generally, nomenclatures used in connection with cell and tissue culture, molecular biology, immunology, micro- biology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

As used herein, the term "nucleic acid" refers to a polymer of two or more nucleotides or nucleotide analogues (such as ribonucleic acid having methylene bridge between the 2'-O and 4'-C atoms of the ribose ring) capable of hybridizing to a complementary nucleic acid. As used herein, this term includes, without limitation, DNA, RNA, LNA, and PNA.

The term "microRNAs" or "miRNAs" as used herein, refers to small noncoding ribonucleic acid (RNA) gene products between 19 and 26 nucleotides long that form a hairpin secondary structure. MicroRNAs described herein are named using the nomenclature set forth in Ambros et al., RNA. 2003 March; 9(3):277-9, incorporated herein by reference, and sequences may be found at mirbase.org.

The term "subject", as used herein, refers to a mammal, e.g. a human, a domestic animal or a livestock including a cat, a dog, a cattle and a horse.

As used herein, the phrase "determining the presence or absence" refers to assessing whether an analyte, such as a microRNA is detectable or undetectable in a biological sample (e.g. a blood sample) using one or more detection techniques for detecting the analyte (such as qPCR, microarray detection, etc.). An analyte that is detected in a biological sample using a detection technique is considered "present". An analyte that is not detected in a biological sample using a detection technique is considered "absent".

As used herein, the term "bind" or "binding refers to non-covalent or covalent interaction between two molecules, such as between two complementary nucleic acids.

As used herein, the term "specifically hybridizing" refers to non-covalent interaction between a first nucleic acid molecule (e.g. a nucleic acid probe having a certain nucleotide sequence) and a second nucleic acid molecule (e.g. a microRNA having a nucleotide sequence complementary to that of the nucleic acid probe). Hybridization conditions have been described in the art and are known to one of skill in the art. In some embodiments, the condition for detecting the hybridization is a suitable condition of a nucleic acid detection assay (e.g., microarray, RT-PCR, or RT-qPCR). The likelihood of hybridization between two nucleic acids correlates with the nucleotide sequence complementary between the two nucleic acids.

The term "hybridize" as used herein, refers to annealing of a first single-stranded nucleic acid to a second complementary single-stranded nucleic, in which complementary nucleotides of the first and second nucleic acids pair by hydrogen bonding.

The phrase "detecting binding of a probe", as used herein, refers to use of a detection method allowing determination that a probe (e.g. a nucleic acid probe) has non-covalently or covalently interacted with a target molecule (e.g. a target nucleic acid in a sample). For example, detecting binding of probe in qPCR may include optical detection of fluorescence of a self-quenching probe following binding to the complementary sequence of a target nucleic acid in the sample. In some embodiments, detecting binding of a probe may include detection of a nucleic acid intercalating agent to detect amplified double-stranded nucleic acid, such as a fluorescent intercalating agent used in qPCR.

As used herein, the term "probe" refers to a molecule or complex that is used to determine the presence or absence and/or amount of a microRNA in a sample (e.g. a blood sample). In certain embodiments, the probe comprises a nucleic acid moiety (e.g., DNA, modified DNA, or modified RNA) that is capable of specifically hybridizing to the microRNA or a complementary DNA (cDNA) thereof. In certain embodiments, the probe comprises a sequence of at least 15, 16, 17, 18, 19, 20, 21, 22, 23, 24, or 25 contiguous nucleotides identical or complementary to the microRNA. In certain embodiments, a probe further comprises a detectable label that is conjugated, covalently or non-covalently, to the nucleic acid moiety. Exemplary detectable labels include without limitation a fluorophore, a small molecule (e.g., a small molecule of the avidin family), an enzyme, an antibody or antibody fragment, or a nucleic acid sequence not present in the subject in a form that is linked to the microRNA (e.g., a barcode sequence). Accordingly, the probe may be a fluorophore-labeled nucleic acid having a nucleotide sequence that is complementary to a nucleotide sequence of a microRNA.

The term "PCR", as used herein, refers to polymerase chain reaction for amplifying an amount of target DNA. PCR relies on thermal cycling, which consists of cycles of repeated heating and cooling of a reaction for DNA denaturation, annealing and enzymatic elongation of the amplified DNA. First, the strands of the DNA are separated at a high temperature in a process called DNA melting or denaturing. Next, the temperature is lowered, allowing the primers and the strands of target DNA to selectively bind or anneal, creating templates for DNA polymerase to amplify the target DNA. Next, at a working temperature of the DNA polymerase, template-dependent DNA synthesis occurs. These steps are repeated to create many copies of the target DNA.

A "primer", as used herein, refers to a short, single-stranded DNA sequence that selectively binds to a target DNA sequence and enables addition of new deoxyribonucleotides by DNA polymerase at the 3' end. According to certain embodiments, the forward primer is 18-35, 19-32 or 21-31 nucleotides in length. The nucleotide sequence of the forward primer is not limited, so long as it specifically hybridizes with part of or an entire target site, and its Tm value may be within a range of 50° C. to 72° C., in particular may be within a range of 58° C. to 61° C., and may be within a range of 59° C. to 60° C. The nucleotide sequence of the primer may be manually designed to confirm the Tm value using a primer Tm prediction tool. Primer nucleotides may include nucleotide analogues and/or modified nucleotides, such as LNA or PNA.

As used herein, the term "RT-PCR" refers to reverse transcription polymerase chain reaction, a process for amplifying RNA. RNA molecules are reverse transcribed to complementary DNA (cDNA) using reverse transcriptase and then using PCR to amplify the resulting cDNA.

As used herein, the term "RT-qPCR" refers to reverse transcription quantitative polymerase chain reaction, a variant of RT-PCR in which amplification of cDNA during the RT-PCR process is quantitatively detected in real time using a probe that detects amplified target DNA. For example, in some embodiments, self-quenching nucleic acid probes are added to the reaction mixture. The self-quenching nucleic acid probes only fluoresce when they bind a target sequence. As each cycle of PCR is completed, the self-quenching probes bind to the amplified DNA, unquench and fluoresce with exposure to a light excitation source. As DNA is amplified, increased probe and target binding results in increased fluorescence of the self-quenching nucleic acid probe. Detection of the fluorescing probes after each amplification cycle allows real-time measurement of the amplification process, as increasing amounts of the nucleic acid probe bind with amplified target DNA and fluoresce. In some embodiments, an intercalating dye probe is added to the reaction mixture that fluoresces upon interaction with double-stranded nucleic acids. The increase in dye fluorescence during the amplification process allows the measurement of DNA amplification in real-time, as increasing amounts of the dye probe intercalate with the increasing amounts of target DNA being amplified.

As used herein, the term "normalize" or "normalizing" refers to adjusting a first measured value (e.g., level of a gene of interest) relative to a second measured value (e.g., level of a housekeeping gene), wherein the first and second measured values are measured from the same sample (e.g., different portions of the same homogenous sample), and wherein the second measured value is correlated to the quantity and/or quality of the sample. Normalization allows obtaining a relative amount of the first value that is not affected by the quantity and/or quality of the sample that may vary from individual sample preparation.

As used herein, the term "normalizing microRNA" refers to a microRNA that is known to have a stable amount in a sample (e.g. a blood sample) and is used to normalize the measured value of a test microRNA in the sample. A single normalizing microRNA may be used to normalize the measured amount of a target microRNA in a sample, or an averaged value of multiple microRNAs may be used for normalization. In certain embodiments, normalization may be calculated by: Number of amplification cycles (average of the normalizer microRNA)–number of amplification cycles (miR of interest).

As used herein, the term "test microRNA" refers to a microRNA the presence or absence and/or amount of which is determined, for example, for diagnosis purpose (e.g., using an algorithm). In some embodiments, the presence or absence and/or amount of one or more test microRNAs can be used additionally for normalization purpose.

As used herein, the term "normalizing probe" refers to a probe that is used to determine the presence or absence and/or amount of a normalizing microRNA in a sample (e.g. a blood sample). In certain embodiments, the normalizing probe comprises a nucleic acid moiety (e.g., DNA, modified DNA, or modified RNA) that is capable of specifically hybridizing to a normalizing microRNA or a complementary DNA (cDNA) thereof.

As used herein, the term "test probe" refers to a probe that is used to determine the presence or absence and/or amount of a test microRNA in a sample (e.g. a blood sample). In certain embodiments, the test probe comprises a nucleic acid moiety (e.g., DNA, modified DNA, or modified RNA) that is capable of specifically hybridizing to a test microRNA or a complementary DNA (cDNA) thereof.

The phrase "a reagent for amplification of a DNA sequence" includes, but is not limited to: (1) a heat-stable DNA polymerase; (2) deoxynucleotide triphosphates (dNTPs); (3) a buffer solution, providing a suitable chemical environment for optimum activity, binding kinetics, and stability of the DNA polymerase; (4) bivalent cations such as magnesium or manganese ions; and (5) monovalent cations, such as potassium ions. The reagents may be provided in the form of a solution, a concentrated solution, or powder.

The phrase "a reagent for reverse transcription of an RNA molecule" encompasses, but is not limited to: a reverse transcriptase; an RNase inhibitor; a primer that hybridizes to a nucleic acid sequence (such as RNA or DNA); a primer that hybridizes to an adenosine oligonucleotide; and a buffer solution that provides a suitable chemical environment for optimum activity, binding kinetics, and stability of the reverse transcriptase. The reagents may be provided in the form of a solution, a concentrated solution, or powder.

As used herein, the term "blood sample" refers to an amount of blood taken from a subject, such as whole blood, or a component portion of blood taken from a subject, such as plasma, which lacks cells normally contained in whole blood (e.g. erythrocytes, leukocytes, and platelets), or serum which is plasma that lacks fibrinogen and some clotting factors.

As used herein, the term "nucleic acid detection method" encompasses any method that may be used to detect the presence of a nucleic acid, including methods of sequencing (e.g. Gilbert sequencing, Sanger sequencing, SMRT sequencing or next-generation sequencing), microarray detection, PCR, RT-PCR, real-time qPCR, real-time RT-qPCR.

As used herein, the term "next-generation sequencing" refers to high-throughput parallel sequencing of short fragments of single-stranded nucleic acids attached to slides or beads, such as techniques by ILLUMINA, ROCHE (454 sequencing), or ION TORRENT, THERMOFISHER. The incorporation of individual nucleotides onto single-stranded nucleic acids may be detected optically (via fluorescence of incorporated nucleotides) or by detection of hydrogen ions released during nucleotide incorporation (e.g. ion semiconductor sequencing).

As used herein, the term "microarray detection" refers to methods of detecting target nucleic acids using single-stranded nucleic acid probes attached to discrete areas of a solid surface (e.g. spots on a slide or beads in microwells). Hybridization of the probes to specific nucleic acids may be detected by a variety of methods, such as using optical detection (e.g. fluorophores, chemiluminescent molecules) or radiographic detection.

As used herein, the term "non-natural label" encompasses, without limitation, one or more labeling molecules that may be bound, attached to, or associated with a biological molecule (such as a nucleic acid, nucleotide, protein, peptide, amino acid, carbohydrate, lipid, primary/secondary metabolites, or chemical product produced by a living organism) to allow detection of the molecule when associated with the biological molecule; non-natural labels are not normally associated with the biological molecule. Exemplary non-natural labels include, without limitation: antigenic tags (e.g. digoxigenin); radioisotopes (e.g. $^{32}P$); enzymes catalyzing chemiluminescent or colorimetric chemical reactions (e.g. horseradish peroxidase or alkaline phosphatase); nucleic acid dyes (e.g. Hoechst 33342, DAPI, ethidium bromide); organic fluorophores (e.g. 6-carboxyfluorescein, tetrachlorofluorescein, fluroscein, rhodamine, or cyanine); fluorophore quenchers (e.g. tetramethylrhodamine, dimethylaminoazobenzenesulfonic acid, BLACK HOLE QUENCHERS, or IOWA BLACK dyes); protein fluorophores (e.g. green fluorescent protein); donor and acceptor fluorophores for fluorescence resonance energy transfer (e.g. fluorescein and tetramethylrhodamine, or NowGFP and mOrange); quantum dot fluorophores (e.g. metal chalcogenides, core shell semiconducting nanocrystals, or alloyed semiconductor quantum dots); and immune system-based molecules bound, attached to, or associated with non-natural labels described herein (e.g. antibodies or antibody fragments labeled with a fluorophore or catalytic enzyme).

As used herein, the term "artificial neural network" refers to a forecasting model based on a linked collection of neural units in silico that loosely model a simple mathematical model of the brain. Artificial neural networks allow identification of complex nonlinear relationships between its response variable and its predictor variables. An artificial neural network may have one or more hidden layers that each include one or more neurons that interact to produce a prediction given two or more variables.

The term "ovarian cancer", as used herein, refers to a group of malignancies affecting the ovary, that have developed from epithelial cells, sex cord-stromal cells (e.g. granulosa, theca, and hilus cells), or germ cells (e.g. oocytes). About 60% of ovarian tumors are of epithelial origin and account for 90% of ovarian cancers (see Karst et al., "Ovarian Cancer Pathogenesis: A Model in Evolution," Journal of Oncology, vol. 2010, Article ID 932371, 13 pages, 2010. doi:10.1155/2010/932371, incorporated herein by reference). Such epithelium-derived ovarian carcinomas are heterogeneous in character, with differences in tumor morphology, clinical symptoms, and genetic alterations. The World Health Organization (WHO) lists eight different tumor histologies, including serous, endometrioid, mucinous, clear cell, transitional cell, squamous cell, mixed epithelial, and undifferentiatied. Tumors of each of these subtypes may be classified as benign (having low malignant potential and/or indolence), malignant, or borderline, as well as low-grade (Type I) or high-grade (Type II).

Type I cancers (such as endometrioid and mucinous carcinomas) are of low histological grade, and exhibit low-grade nuclei with infrequent mitotic figures (see Vang et al., Adv Anat Pathol. 2009 September; 16(5): 267-282, incorporated herein by reference). Type I ovarian serous cancers often have mutations of the KRAS, BRAF or ERBB2 genes, and lack TP53 mutations. Type I tumors are usually indolent and have better patient outcomes, although they can develop into Type II malignancies. In contrast, Type II ovarian serous cancers (such as serous carcinoma) are considered a higher histological grade, having high-grade nuclei and numerous mitotic figures, and are characterized by rapid tumor development. Genetically, Type II ovarian serous tumors usually include TP53 mutation and lack mutations of KRAS, BRAF, or ERBB2.

Ovarian tumors may also be surgically staged to indicate malignancy. Stage I indicates confinement to the ovary. Stage IA indicates that the cancer is completely inside one ovary, and stage IB indicates that the cancer is completely inside both ovaries. Stage IC indicates that the cancer is in both ovaries and one of the following: some cancer is on the surface of an ovary; cancer cells are present in fluid inside the abdomen (fluid may be taken during surgery); or that an ovary ruptures before or during surgery. Stage IC1 indicates that the tumor capsule broke during surgery to cause a surgical spill of cancer cells into the abdomen and/or pelvis. Stage IC2 indicates that at least one ovary or fallopian tube, or the tumor capsule ruptured before surgery. Stage IC3 indicates detection of cancer cells in fluid or washings from the abdomen.

Stage II indicates tumor extension beyond the ovary to other pelvic structures (e.g. fallopian tube or uterus). Stage IIA indicates that the cancer has grown into the fallopian tubes or into the uterus. Stage IIB indicates that the cancer has grown into other pelvic tissues, such as the bladder or rectum. Stage IIC indicates that the cancer has grown into pelvic tissues and that cancer cells are present in fluid taken from inside the abdomen.

Stage III indicates metastasis to the peritoneum and/or regional lymph nodes. Stage IIIA indicates that cancer growths are visible microscopically in tissue from the abdominal lining. Stage IIIA1 indicates that the cancer is in one or both ovaries or fallopian tubes, and may have spread or grown into the pelvis or nearby organs. Stage IIIA1(i) indicates that the areas of cancer spread in the lymph nodes are 10 mm across or smaller. Stage IIIA1(ii) indicates that the areas of cancer spread in the lymph nodes is great than 10 mm across. Stage IIIA2 indicates that the cancer is in one or both ovaries or fallopian tubes, and may have spread or grown into the pelvis or nearby organs, and that microscopic examination of biopsies from the upper lining of the abdomen show small cancer deposits. Stage IIIB indicates that tumor growths 2 cm or smaller are visible on the abdominal lining or the capsule of the liver or spleen. Stage IIIC indicates that tumor growths 2 cm or larger are visible on the abdominal lining, and/or that cancer is detected in the lymph nodes of the upper abdomen, groin, or behind the uterus.

Stage IV indicates metastasis of the ovarian cancer past the peritoneum. Stage IVA indicates that the cancer has caused pleural effusion (build up fluid in the lining of the lungs. Stage IVB indicates that the cancer has spread inside the liver or spleen, to lymph nodes in the groin, or outside the abdomen and/or to other organs (e.g. the lungs).

As used herein, the term "treating" or "treatment" refers to relieving, reducing, or alleviating at least one symptom in a subject or effecting a delay of progression of a disease. For example, treatment can be the diminishment of one or several symptoms of a disorder or complete eradication of a disorder, such as cancer. Within the meaning of the present disclosure, the term "treat" also denotes to arrest and/or reduce the risk of worsening a disease, or prevention of at least one symptom associated with or caused by the state, disease or disorder being prevented. For example, treatments may relieve, reduce or alleviate at least one symptom of ovarian cancer.

The course of treatment of ovarian cancer is often similar for many patients in order to account for the heterogeneity of response by the different cancer types. Such treatments include cytoreductive surgery (e.g. debulking to remove the tumor, salpingo-oophorectomy, hysterectomy, lymphadenectomy, omentectomy), followed by platinum-based chemotherapy (e.g. cisplatin or carboplatin and a taxane). In some instances, other chemotherapeutic agents may be used if the ovarian cancer is resistant to platinum-based drugs either alone or in combination, such as liposomal doxorubicin, paclitaxel, docetaxel, nab-paclitaxel, gemcitabine, etoposide, pemetrexed, cyclophosphamide, topotecan, vinorelbine, or irinotecan.

Other treatments of ovarian cancer used in place of or in addition to surgery and chemotherapy may include administration of a targeted antibody, such as bevacizumab or olaparib. In some instances, radiation therapy may be used to treat ovarian cancer, such as external beam radiation therapy or brachytherapy (implantation of a radioactive material near the affected) in order to target the affected area. In some instances, hormone therapy may be used to treat ovarian cancer, such as administration of luteinizing-hormone-releasing hormone (LHRH) agonists (e.g. goserelin and/or leuprolide), tamoxifen, or aromatase inhibitors (e.g. letrozole, anastrozole, and exemestane).

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following examples, which are included for purposes of illustration only and are not intended to be limiting.

The following examples which should not be construed as further limiting.

Figure 1B:
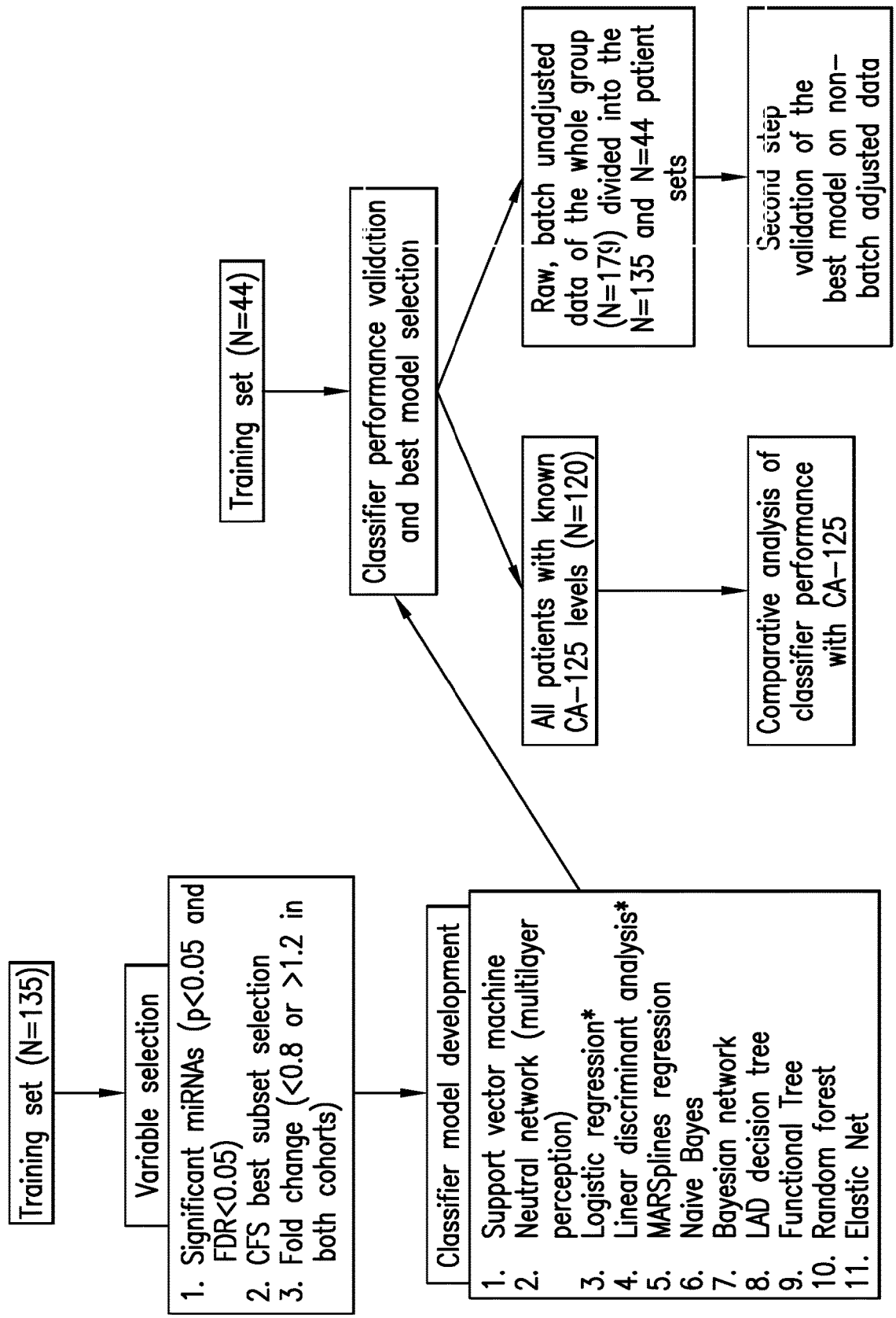
FIG. 1B shows a flow chart of the model development and testing.

Example 1: Neural Networks for Identifying Ovarian Cancer Patients Using miRNA Sequencing Data The goal of this study was to produce a circulating miRNA signature from human sera for the diagnosis of ovarian cancer. FIG. 1A shows a flow chart of the protocol for miRNA sequencing, filtering, batch adjustment and separation into the training and testing sets. FIG. 1B shows a flow chart of the model development and testing. A single heterogeneous patient cohort of pre-treatment (prior to either surgery or chemotherapy) blood samples was constructed from 180 women enrolled in two independent prospective cohort studies, the Pelvic Mass Protocol (PMP; see Materials and methods) consisting of 120 patients and the ERASMOS study (see Materials and Methods) comprising 60 patients. Both of the cohorts consisted of patients presenting for surgical management of a pelvic mass. The smaller cohort consisted of sequential cases, reflecting the natural frequency of different ovarian tumor subtypes in the clinical population, including the fact that most women with invasive ovarian cancer presented with advanced stage diseases. The larger cohort was derived from a case-control study and allowed enrichment of the study population for less common clinical cases that would be expected to confound a conventional screening algorithm, including benign complex ovarian masses, borderline tumors, early stage cancers, and non-serous histologic subtypes. To this latter cohort, healthy race and age-matched controls were added from the NECC study (see Materials and Methods). Table 1 below lists the demographics of the patients in the study populations.

TABLE 1

Demographics of patients in model study populations

| | ERASMOS (n = 60) | PMP/NECC (n = 119*) | p-value |
|---|---|---|---|
| Age, years, median (SD) † | 57 (9.8) | 56 (7.1) | 0.44 |
| CA-125, units/ml, median (SD) † | 155 (689.8) | 88.1 (1335.5) | 0.72 |
| Histology, n (%)‡ | | | |
| Control | 0 (0) | 15 (12.6) | <0.0001 |
| Serous cystadenoma/cystadenofibroma | 7 (11.7) | 14 (11.8) | |
| Endometrioma | 0 (0) | 15 (12.6) | |

TABLE 1-continued

Demographics of patients in model study populations

| | ERASMOS (n = 60) | PMP/NECC (n = 119*) | p-value |
|---|---|---|---|
| Other benign lesion | 9 (15.0) | 0 (0) | |
| Borderline mucinous tumor | 2 (3.3) | 0 (0) | |
| Borderline serous tumor | 5 (8.3) | 15 (12.6) | |
| Stage I/II serous adenocarcinoma | 5 (8.3) | 20 (16.8) | |
| Stage III/IV serous adenocarcinoma | 19 (31.2) | 10 (8.4) | |
| Stage I/II clear cell/endometrioid adenocarcinoma | 6 (10.0) | 20 (16.8) | |
| Stage III/IV clear cell/endometrioid adenocarcinoma | 0 (0) | 10 (8.4) | |
| Mucinous adenocarcinoma | 1 (1.7) | 0 (0) | |
| Other ovarian cancer | 10 (10.0) | 0 (0) | |
| Stage, n (%)‡ | | | |
| Not applicable | 16 (26.7) | 59 (49.6) | <0.0001 |
| I | 9 (15.0) | 22 (18.5) | |
| II | 8 (13.3) | 18 (15.1) | |
| III | 19 (31.2) | 18 (15.1) | |
| IV | 8 (13.3) | 2 (1.7) | |
| Grade, n (%)‡ | | | |
| Not applicable | 16 (26.7) | 44 (37.0) | 0.07 |
| Borderline | 7 (11.7) | 15 (12.6) | |
| 1 (well-differentiated) | 6 (10.0) | 12 (10.1) | |
| 2 (moderately differentiated) | 3 (5.0) | 12 (10.1) | |
| 3 (poorly differentiated) | 28 (46.7) | 36 (30.3) | |

ERASMOS—Effects of Regional Analgesia on Serum miRNA after Oncology Surgery Study
PMP—Pelvic Mass Protocol
NECC—New England Case Control study
*15 samples from NECC, 114 samples from PMP
† Student's t-test
‡chi-square test Total RNAs from the sera were extracted, converted into small RNA cDNA libraries, and sequenced, resulting in 2578 known or putative miRNA sequences. Filtering for miRNAs present in at least 50% of both cohorts at a detection threshold of 10 transcripts per million reads (tpm) left 192 miRNAs (see Table 2 below) to test in the models. One patient was excluded due to an unusual miRNA profile that was connected to recent cardiac ischemia.

TABLE 2

192 miRNAs that can be reproducibly detected in human serum by miRNA sequencing

| SEQ ID NO. | MicroRNA miRBase ID | Sequence |
|---|---|---|
| 1 | hsa-let-7a-3p | CUAUACAAUCUACUGUCUUUC |
| 2 | hsa-let-7a-5p | UGAGGUAGUAGGUUGUAUAGUU |
| 3 | hsa-let-7b-3p | CUAUACAACCUACUGCCUUCCC |
| 4 | hsa-let-7b-5p | UGAGGUAGUAGGUUGUGUGGUU |
| 5 | hsa-let-7c-5p | UGAGGUAGUAGGUUGUAUGGUU |
| 6 | hsa-let-7d-3p | CUAUACGACCUGCUGCCUUUCU |
| 7 | hsa-let-7d-5p | AGAGGUAGUAGGUUGCAUAGUU |
| 8 | hsa-let-7e-5p | UGAGGUAGGAGGUUGUAUAGUU |
| 9 | hsa-let-7f-5p | UGAGGUAGUAGAUUGUAUAGUU |
| 10 | hsa-let-7g-5p | UGAGGUAGUAGUUUGUACAGUU |
| 11 | hsa-let-7i-5p | UGAGGUAGUAGUUUGUGCUGUU |
| 12 | hsa-miR-1-5p | UGGAAUGUAAAGAAGUAUGUAU |
| 13 | hsa-miR-7-5p | UGGAAGACUAGUGAUUUUGUUGU |
| 14 | hsa-miR-10a-5p | UACCCUGUAGAUCCGAAUUUGUG |
| 15 | hsa-miR-10b-5p | UACCCUGUAGAACCGAAUUUGUG |
| 16 | hsa-miR-15b-3p | CGAAUCAUUAUUUGCUGCUCUA |
| 17 | hsa-miR-15b-5p | UAGCAGCACAUCAUGGUUUACA |
| 18 | hsa-miR-16-2-3p | CCAAUAUUACUGUGCUGCUUUA |
| 19 | hsa-miR-16-5p | UAGCAGCACGUAAAUAUUGGCG |
| 20 | hsa-miR-17-5p | CAAAGUGCUUACAGUGCAGGUAG |
| 21 | hsa-miR-19a-3p | UGUGCAAAUCUAUGCAAAACUGA |
| 22 | hsa-miR-19b-3p | UGUGCAAAUCCAUGCAAAACUGA |
| 23 | hsa-miR-20a-5p | UAAAGUGCUUAUAGUGCAGGUAG |
| 24 | hsa-miR-20b-5p | CAAAGUGCUCAUAGUGCAGGUAG |
| 25 | hsa-miR-21-5p | UAGCUUAUCAGACUGAUGUUGA |
| 26 | hsa-miR-22-3p | AAGCUGCCAGUUGAAGAACUGU |

TABLE 2-continued 192 miRNAs that can be reproducibly detected in human serum by miRNA sequencing

| SEQ ID NO. | MicroRNA miRBase ID | Sequence |
|---|---|---|
| 27 | hsa-miR-22-5p | AGUUCUUCAGUGGCAAGCUUUA |
| 28 | hsa-miR-23a-3p | AUCACAUUGCCAGGGAUUUCC |
| 29 | hsa-miR-23b-3p | AUCACAUUGCCAGGGAUUACC |
| 30 | hsa-miR-24-2-5p | UGCCUACUGAGCUGAAACACAG |
| 31 | hsa-miR-24-3p | UGGCUCAGUUCAGCAGGAACAG |
| 32 | hsa-miR-25-3p | CAUUGCACUUGUCUCGGUCUGA |
| 33 | hsa-miR-26a-5p | UUCAAGUAAUCCAGGAUAGGCU |
| 34 | hsa-miR-26b-5p | UUCAAGUAAUUCAGGAUAGGU |
| 35 | hsa-miR-27a-3p | UUCACAGUGGCUAAGUUCCGC |
| 36 | hsa-miR-27b-3p | UUCACAGUGGCUAAGUUCUGC |
| 37 | hsa-miR-28-3p | CACUAGAUUGUGAGCUCCUGGA |
| 38 | hsa-miR-28-5p | AAGGAGCUCACAGUCUAUUGAG |
| 39 | hsa-miR-29a-3p | UAGCACCAUCUGAAAUCGGUUA |
| 40 | hsa-miR-30a-3p | CUUUCAGUCGGAUGUUUGCAGC |
| 41 | hsa-miR-30a-5p | UGUAAACAUCCUCGACUGGAAG |
| 42 | hsa-miR-30c-5p | UGUAAACAUCCUACACUCUCAGC |
| 43 | hsa-miR-30d-5p | UGUAAACAUCCCCGACUGGAAG |
| 44 | hsa-miR-30e-3p | CUUUCAGUCGGAUGUUUACAGC |
| 45 | hsa-miR-30e-5p | UGUAAACAUCCUUGACUGGAAG |
| 46 | hsa-miR-32-5p | UAUUGCACAUUACUAAGUUGCA |
| 47 | hsa-miR-92a-3p | UAUUGCACUUGUCCCGGCCUGU |
| 48 | hsa-miR-92b-3p | UAUUGCACUCGUCCCGGCCUCC |
| 49 | hsa-miR-93-5p | CAAAGUGCUGUUCGUGCAGGUAG |
| 50 | hsa-miR-98-5p | UGAGGUAGUAAGUUGUAUUGUU |
| 51 | hsa-miR-99a-5p | AACCCGUAGAUCCGAUCUUGUG |
| 52 | hsa-miR-99b-5p | CACCCGUAGAACCGACCUUGCG |
| 53 | hsa-miR-100-5p | AACCCGUAGAUCCGAACUUGUG |
| 54 | hsa-miR-101-3p | UACAGUACUGUGAUAACUGAA |
| 55 | hsa-miR-103a-3p | AGCAGCAUUGUACAGGGCUAUGA |
| 56 | hsa-miR-106b-3p | CCGCACUGUGGGUACUUGCUGC |
| 57 | hsa-miR-106b-5p | UAAAGUGCUGACAGUGCAGAU |
| 58 | hsa-miR-107 | AGCAGCAUUGUACAGGGCUAUGA |
| 59 | hsa-miR-122-5p | UGGAGUGUGACAAUGGUGUUUG |
| 60 | hsa-miR-125a-5p | UCCCUGAGACCCUUUAACCUGUGA |
| 61 | hsa-miR-125b-5p | UCCCUGAGACCCUAACUUGUGA |
| 62 | hsa-miR-126-3p | UCGUACCGUGAGUAAUAAUGCG |
| 63 | hsa-miR-126-5p | CAUUAUUACUUUUGGUACGCG |
| 64 | hsa-miR-128-3p | UCACAGUGAACCGGUCUCUUU |
| 65 | hsa-miR-130a-3p | CAGUGCAAUGUUAAAAGGGCAU |
| 66 | hsa-miR-130b-5p | ACUCUUUCCCUGUUGCACUAC |
| 67 | hsa-miR-134-5p | UGUGACUGGUUGACCAGAGGGG |
| 68 | hsa-miR-139-3p | UGGAGACGCGGCCCUGUUGGAGU |
| 69 | hsa-miR-139-5p | UCUACAGUGCACGUGUCUCCAGU |
| 70 | hsa-miR-140-3p | UACCACAGGGUAGAACCACGG |
| 71 | hsa-miR-140-5p | CAGUGGUUUUACCCUAUGGUAG |
| 72 | hsa-miR-142-3p | UGUAGUGUUUCCUACUUUAUGGA |
| 73 | hsa-miR-142-5p | CAUAAAGUAGAAAGCACUACU |
| 74 | hsa-miR-143-3p | UGAGAUGAAGCACUGUAGCUC |
| 75 | hsa-miR-144-3p | UACAGUAUAGAUGAUGUACU |
| 76 | hsa-miR-144-5p | GGAUAUCAUCAUAUACUGUAAG |
| 77 | hsa-miR-145-3p | GGAUUCCUGGAAAUACUGUUCU |
| 78 | hsa-miR-146a-5p | UGAGAACUGAAUUCCAUGGGUU |
| 79 | hsa-miR-146b-5p | UGAGAACUGAAUUCCAUAGGCU |
| 80 | hsa-miR-148a-3p | UCAGUGCACUACAGAACUUUGU |
| 81 | hsa-miR-148a-5p | AAAGUUCUGAGACACUCCGACU |
| 82 | hsa-miR-148b-3p | UCAGUGCAUCACAGAACUUUGU |
| 83 | hsa-miR-150-5p | UCUCCCAACCCUUGUACCAGUG |
| 84 | hsa-miR-151a-3p | CUAGACUGAAGCUCCUUGAGG |
| 85 | hsa-miR-152-3p | UCAGUGCAUGACAGAACUUGG |
| 86 | hsa-miR-155-5p | UUAAUGCUAAUCGUGAUAGGGGU |
| 87 | hsa-miR-181 a-2-3p | ACCACUGACCGUUGACUGUACC |
| 88 | hsa-miR-181a-5p | AACAUUCAACGCUGUCGGUGAGU |
| 89 | hsa-miR-181b-5p | AACAUUCAUUGCUGUCGGUGGGU |
| 90 | hsa-miR-181d-5p | AACAUUCAUUGUUGUCGGUGGGU |
| 91 | hsa-miR-182-5p | UUUGGCAAUGGUAGAACUCACACU |
| 92 | hsa-miR-183-5p | UAUGGCACUGGUAGAAUUCACU |
| 93 | hsa-miR-185-3p | AGGGGCUGGCUUUCCUCUGGUC |
| 94 | hsa-miR-185-5p | UGGAGAGAAAGGCAGUUCCUGA |
| 95 | hsa-miR-186-5p | CAAAGAAUUCUCCUUUUGGGCU |
| 96 | hsa-miR-191-5p | CAACGGAAUCCCAAAAGCAGCUG |
| 97 | hsa-miR-192-5p | CUGACCUAUGAAUUGACAGCC |
| 98 | hsa-miR-193a-5p | UGGGUCUUUGCGGGCGAGAUGA |
| 99 | hsa-miR-194-5p | UGUAACAGCAACUCCAUGUGGA |

TABLE 2-continued 192 miRNAs that can be reproducibly detected in human serum by miRNA sequencing

| SEQ ID NO. | MicroRNA miRBase ID | Sequence |
|---|---|---|
| 100 | hsa-miR-197-3p | UUCACCACCUUCUCCACCCAGC |
| 101 | hsa-miR-199a-3p | ACAGUAGUCUGCACAUUGGUUA |
| 102 | hsa-miR-199a-5p | CCCAGUGUUCAGACUACCUGUUC |
| 103 | hsa-miR-199b-3p | ACAGUAGUCUGCACAUUGGUUA |
| 104 | hsa-miR-200a-3p | UAACACUGUCUGGUAACGAUGU |
| 105 | hsa-miR-200c-3p | UAAUACUGCCGGGUAAUGAUGGA |
| 106 | hsa-miR-203a-5p | GUGAAAUGUUUAGGACCACUAG |
| 107 | hsa-miR-215-5p | AUGACCUAUGAAUUGACAGAC |
| 108 | hsa-miR-221-3p | AGCUACAUUGUCUGCUGGGUUUC |
| 109 | hsa-miR-222-3p | AGCUACAUCUGGCUACUGGGU |
| 110 | hsa-miR-223-3p | UGUCAGUUUGUCAAAUACCCCA |
| 111 | hsa-miR-223-5p | CGUGUAUUUGACAAGCUGAGUU |
| 112 | hsa-miR-224-5p | CAAGUCACUAGUGGUUCCGUU |
| 113 | hsa-miR-320a | AAAAGCUGGGUUGAGAGGGCGA |
| 114 | hsa-miR-320b | AAAAGCUGGGUUGAGAGGGCAA |
| 115 | hsa-miR-320c | AAAAGCUGGGUUGAGAGGGU |
| 116 | hsa-miR-320d | AAAAGCUGGGUUGAGAGGA |
| 117 | hsa-miR-323a-3p | CACAUUACACGGUCGACCUCU |
| 118 | hsa-miR-323b-3p | CCCAAUACACGGUCGACCUCUU |
| 119 | hsa-miR-328-3p | CUGGCCCUCUCUGCCCUUCCGU |
| 120 | hsa-miR-330-3p | GCAAAGCACACGGCCUGCAGAGA |
| 121 | hsa-miR-335-3p | UUUUUCAUUAUUGCUCCUGACC |
| 122 | hsa-miR-335-5p | UCAAGAGCAAUAACGAAAAAUGU |
| 123 | hsa-miR-338-5p | AACAAUAUCCUGGUGCUGAGUG |
| 124 | hsa-miR-339-3p | UGAGCGCCUCGACGACAGAGCCG |
| 125 | hsa-miR-340-3p | UCCGUCUCAGUUACUUUAUAGC |
| 126 | hsa-miR-340-5p | UUAUAAAGCAAUGAGACUGAUU |
| 127 | hsa-miR-342-5p | AGGGGUGCUAUCUGUGAUUGA |
| 128 | hsa-miR-345-5p | GCUGACUCCUAGUCCAGGGCUC |
| 129 | hsa-miR-361-3p | UCCCCCAGGUGUGAUUCUGAUUU |
| 130 | hsa-miR-361-5p | UUAUCAGAAUCUCCAGGGGUAC |
| 131 | hsa-miR-363-3p | AAUUGCACGGUAUCCAUCUGUA |
| 132 | hsa-miR-370-3p | GCCUGCUGGGGUGGAACCUGGU |
| 133 | hsa-miR-374a-5p | UUAUAAUACAACCUGAUAAGUG |
| 134 | hsa-miR-375 | UUUGUUCGUUCGGCUCGCGUGA |
| 135 | hsa-miR-378a-3p | ACUGGACUUGGAGUCAGAAGGC |
| 136 | hsa-miR-378c | ACUGGACUUGGAGUCAGAAGAGUGG |
| 137 | hsa-miR-379-5p | UGGUAGACUAUGGAACGUAGG |
| 138 | hsa-miR-381-3p | UAUACAAGGGCAAGCUCUCUGU |
| 139 | hsa-miR-382-5p | GAAGUUGUUCGUGGUGGAUUCG |
| 140 | hsa-miR-409-3p | GAAUGUUGCUCGGUGAACCCCU |
| 141 | hsa-miR-421 | AUCAACAGACAUUAAUUGGGCGC |
| 142 | hsa-miR-423-3p | AGCUCGGUCUGAGGCCCCUCAGU |
| 143 | hsa-miR-423-5p | UGAGGGGCAGAGAGCGAGACUUU |
| 144 | hsa-miR-424-3p | CAAAACGUGAGGCGCUGCUAU |
| 145 | hsa-miR-425-3p | AUCGGGAAUGUCGUGUCCGCCC |
| 146 | hsa-miR-425-5p | AAUGACACGAUCACUCCCGUUGA |
| 147 | hsa-miR-432-5p | UCUUGGAGUAGGUCAUUGGGUGG |
| 148 | hsa-miR-450a-5p | UUUUGCGAUGUGUUCCUAAUAU |
| 149 | hsa-miR-450b-5p | UUUUGCAAUAUGUUCCUGAAUA |
| 150 | hsa-miR-451a | AAACCGUUACCAUUACUGAGUU |
| 151 | hsa-miR-483-5p | AAGACGGGAGGAAAGAAGGGAG |
| 152 | hsa-miR-484 | UCAGGCUCAGUCCCCUCCCGAU |
| 153 | hsa-miR-486-3p | CGGGGCAGCUCAGUACAGGAU |
| 154 | hsa-miR-486-5p | UCCUGUACUGAGCUGCCCCGAG |
| 155 | hsa-miR-493-5p | UUGUACAUGGUAGGCUUUCAUU |
| 156 | hsa-miR-500a-3p | AUGCACCUGGGCAAGGAUUCUG |
| 157 | hsa-miR-501-3p | AAUGCACCCGGGCAAGGAUUCU |
| 158 | hsa-miR-502-3p | AAUGCACCUGGGCAAGGAUUCA |
| 159 | hsa-miR-503-5p | UAGCAGCGGGAACAGUUCUGCAG |
| 160 | hsa-miR-532-5p | CAUGCCUUGAGUGUAGGACCGU |
| 161 | hsa-miR-543 | AAACAUUCGCGGUGCACUUCUU |
| 162 | hsa-miR-550a-5p | AGUGCCUGAGGGAGUAAGAGCCC |
| 163 | hsa-miR-574-5p | UGAGUGUGUGUGUGUGAGUGUGU |
| 164 | hsa-miR-576-3p | AAGAUGUGGAAAAAUUGGAAUC |
| 165 | hsa-miR-584-5p | UUAUGGUUUGCCUGGGACUGAG |
| 166 | hsa-miR-589-5p | UGAGAACCACGUCUGCUCUGAG |
| 167 | hsa-miR-625-3p | GACUAUAGAACUUUCCCCCUCA |
| 168 | hsa-miR-629-5p | UGGGUUUACGUUGGGAGAACU |
| 169 | hsa-miR-652-3p | AAUGGCGCCACUAGGGUUGUG |
| 170 | hsa-miR-654-3p | UAUGUCUGCUGACCAUCACCUU |
| 171 | hsa-miR-660-5p | UACCCAUUGCAUAUCGGAGUUG |

TABLE 2-continued 192 miRNAs that can be reproducibly detected in human serum by miRNA sequencing

| SEQ ID NO. | MicroRNA miRBase ID | Sequence |
|---|---|---|
| 172 | hsa-miR-664a-5p | ACUGGCUAGGGAAAAUGAUUGGAU |
| 173 | hsa-miR-744-5p | UGCGGGGCUAGGGCUAACAGCA |
| 174 | hsa-miR-769-5p | UGAGACCUCUGGGUUCUGAGCU |
| 175 | hsa-miR-941 | CACCCGGCUGUGUGCACAUGUGC |
| 176 | hsa-miR-942-5p | UCUUCUCUGUUUUGGCCAUGUG |
| 177 | hsa-miR-1180-3p | UUUCCGGCUCGCGUGGGUGUGU |
| 178 | hsa-miR-1246 | AAUGGAUUUUUGGAGCAGG |
| 179 | hsa-miR-1285-3p | UCUGGGCAACAAAGUGAGACCU |
| 180 | hsa-miR-1301-3p | UUGCAGCUGCCUGGGAGUGACUUC |
| 181 | hsa-miR-1307-3p | ACUCGGCGUGGCGUCGGUCGUG |
| 182 | hsa-miR-1307-5p | UCGACCGGACCUCGACCGGCU |
| 183 | hsa-miR-1908-5p | CGGCGGGGACGGCGAUUGGUC |
| 184 | hsa-miR-2110 | UUGGGGAAACGGCCGCUGAGUG |
| 185 | hsa-miR-3158-3p | AAGGGCUUCCUCUCUGCAGGAC |
| 186 | hsa-miR-3613-5p | UGUUGUACUUUUUUUUUUGUUC |
| 187 | hsa-miR-3615 | UCUCUCGGCUCCUCGCGGCUC |
| 188 | hsa-miR-4433b-3p | CAGGAGUGGGGGGUGGGACGU |
| 189 | hsa-miR-4443 | UUGGAGGCGUGGGUUUU |
| 190 | hsa-miR-4732-5p | UGUAGAGCAGGGAGCAGGAAGCU |
| 191 | hsa-miR-6842-3p | UUGGCUGGUCUCUGCUCCGCAG |
| 192 | hsa-miR-7706 | UGAAGCGCCUGUGCUCUGCCGAGA |

The data for the remaining 179 patients were then batch-adjusted using ComBat to account for the two different study cohorts. Subject samples were randomized into "training" and "testing" sets in an approximate 3:1 ratio (see Table 3 below). There were no differences in the distribution of histopathological diagnoses between the training and testing sets (p=1.0).

TABLE 3

Demographics of patients after stratified random sampling into training and testing sets.

| | Training (n = 135) | Testing (n = 44) | p-value |
|---|---|---|---|
| Age, years, median (SD) † | 56 (8.1) | 56 (8.3) | 1.0 |
| CA-125, units/ml, median (SD) † | 126.5 (1193.5) | 105.6 (577.8) | 0.91 |
| Pathology, n (%)‡ | | | 1.0 |
| Control | 11 (8.1) | 4 (9.1) | |
| Benign lesions | 34 (25.2) | 11 (25.0) | |
| Borderline tumors | 16 (11.9) | 5 (11.4) | |
| Stage I/II invasive cancers | 41 (30.4) | 12 (27.3) | |
| Stage III/IV invasive cancers | 33 (24.4) | 12 (27.3) | |

† student's t-test
‡ chi-square test

As the dataset included more variables than cases, direct model development on the full dataset would have resulted in overfitted results. Therefore the variables for disease classification model development were preselected using three different methods: a significance filter, a group-stratified fold change filter, and a correlation-based feature selection (CFS) (see results in Table 4 below). Eleven different types of machine learning algorithms were then deployed (linear discriminant analysis, logistic regression, multivariate adaptive regression splines, naive Bayes, neural network, support vector machine, functional tree, Least Absolute Deviation regression trees (LAD tree), Bayesian network, elastic net regression, and random forest) on the three sets of variables to separate the cases of invasive cancer from the healthy controls or benign/borderline masses. Although borderline tumors are not strictly benign, they are clinically indolent and seldom fatal, and were therefore grouped with benign lesions, as the goal of the analysis was to diagnose the tumors most contributing to mortality.

TABLE 4

Variables (biomarkers) selected using a significance filter, a correlation-based feature selection (CFS), and a group-stratified fold change filter

| Significance-based selection | CFS variable selection | Expression fold selection |
|---|---|---|
| hsa-miR-29a-3p (SEQ ID NO: 39) | hsa-miR-16-2-3p (SEQ ID NO: 18) | hsa-miR-23b-3p (SEQ ID NO: 29) |
| hsa-miR-30d-5p (SEQ ID NO: 43) | hsa-miR-200a-3p (SEQ ID NO: 104) | hsa-miR-29a-3p (SEQ ID NO: 39) |
| hsa-miR-200a-3p (SEQ ID NO: 104) | hsa-miR-200c-3p (SEQ ID NO: 105) | hsa-miR-32-5p (SEQ ID NO: 46) |
| hsa-miR-200c-3p (SEQ ID NO: 105) | hsa-miR-320b (SEQ ID NO: 114) | hsa-miR-92a-3p (SEQ ID NO: 47) |
| hsa-miR-320d (SEQ ID NO: 116) | hsa-miR-320d (SEQ ID NO: 116) | hsa-miR-150-5p (SEQ ID NO: 83) |
| hsa-miR-320c (SEQ ID NO: 115) | | hsa-miR-200a-3p (SEQ ID NO: 104) |
| hsa-miR-450b-5p (SEQ ID NO: 149) | | hsa-miR-200c-3p (SEQ ID NO: 105) |
| hsa-miR-203a-5p (SEQ ID NO: 106) | | hsa-miR-203a-5p (SEQ ID NO: 106) |
| hsa-miR-486-3p (SEQ ID NO: 153) | | hsa-miR-320c (SEQ ID NO: 115) |
| hsa-miR-1246 (SEQ ID NO: 178) | | hsa-miR-320d (SEQ ID NO: 116) |
| hsa-miR-1307-5p (SEQ ID NO: 182) | | hsa-miR-335-5p (SEQ ID NO: 122) |
| | | hsa-miR-450b-5p (SEQ ID NO: 149) |

TABLE 4-continued

Variables (biomarkers) selected using a significance filter, a correlation-based feature selection (CFS), and a group-stratified fold change filter

| Significance-based selection | CFS variable selection | Expression fold selection |
|---|---|---|
| | | hsa-miR-1246 (SEQ ID NO: 178) |
| | | hsa-miR-1307-5p (SEQ ID NO: 182) |

The machine learning algorithms were graded in terms of receiver operating characteristic area under the curve (ROC AUC) (see Table 5 below). Without using a true population with a defined prevalence of ovarian cancer, it was impossible to assign a positive or negative predictive value for each test set (e.g. linear discriminant analysis using the biomarkers selected using the significance filter). However, it was possible to estimate the clinical utility of the algorithms by defining the sensitivity and specificity for each selected test set (see FIGS. 2A-2C). Descriptions of the variable selection methods and algorithms appear below in the Materials and Methods section.

TABLE 5

Performance of the eleven classifier models on the testing set

| Model/Method | Significance-based | Correlation-based feature selection subset | Fold change-based |
|---|---|---|---|
| Linear discriminant analysis | 0.80 (0.66-0.93) | 0.76 (0.62-0.90) | 0.78 (0.64-0.92) |
| Logistic regression | 0.81 (0.68-0.94) | 0.75 (0.61-0.90) | 0.82 (0.70-0.94) |
| Neural network | 0.84 (0.72-0.96) | 0.75 (0.60-0.89) | 0.90 (0.81-0.99) |
| Support vector machine | 0.77 (0.63-0.91) | 0.73 (0.58-0.87) | 0.77 (0.63-0.91) |
| Multivariate adaptive regression splines | 0.57 (0.40-0.74) | 0.66 (0.49-0.82) | 0.73 (0.58-0.88) |
| Naive Bayes classifier | 0.75 (0.60-0.89) | 0.68 (0.52-0.84) | 0.75 (0.60-0.89) |
| Least Absolute Deviation regression tree | 0.77 (0.63-0.91) | 0.61 (0.44-0.78) | 0.69 (0.53-0.84) |
| Functional tree | 0.78 (0.64-0.91) | 0.77 (0.63-0.91) | 0.68 (0.52-0.84) |
| Bayesian network | 0.72 (0.56-0.87) | 0.67 (0.52-0.83) | 0.72 (0.56-0.87) |
| Random forest | 0.78 (0.64-0.91) | 0.71 (0.56-0.86) | 0.76 (0.62-0.90) |
| Elastic net | 0.80 (0.67-0.93) | 0.76 (0.62-0.90) | 0.79 (0.66-0.92) |

Figure 2A:
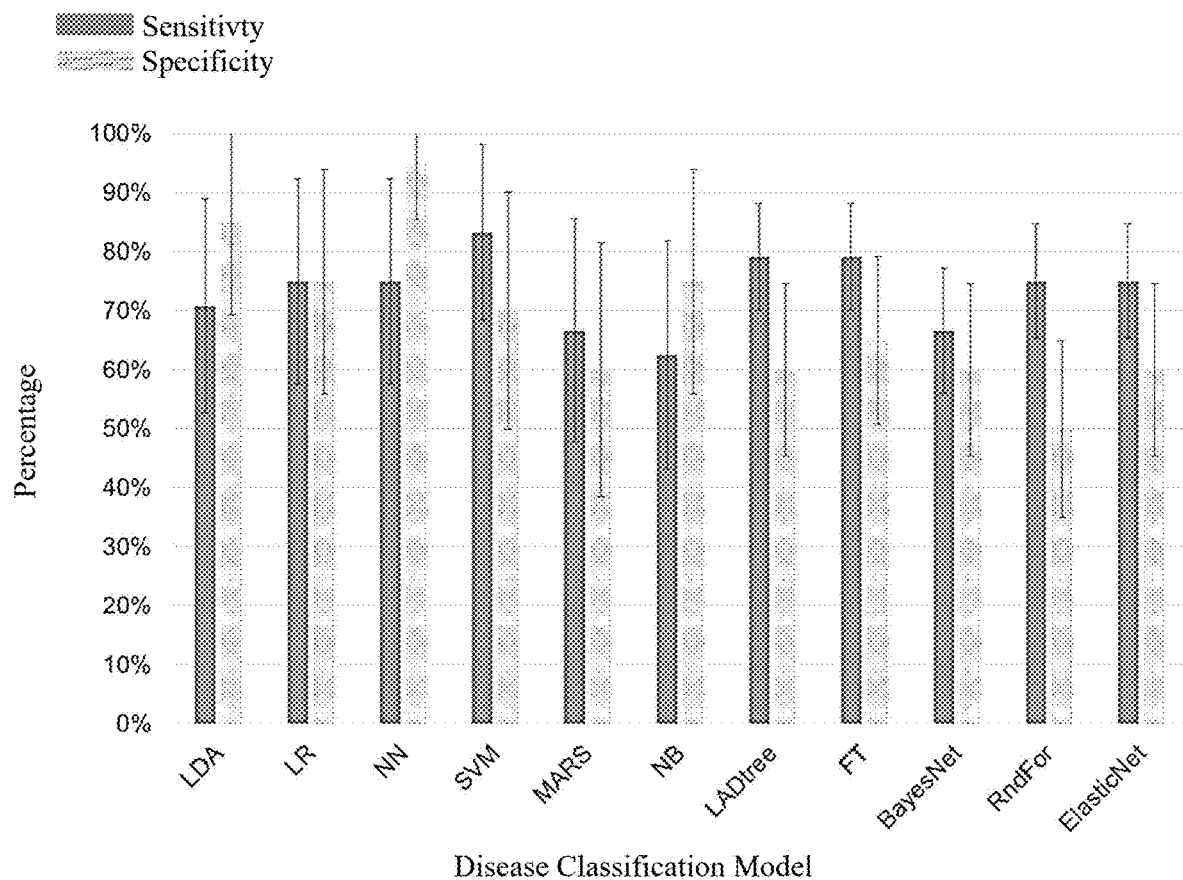
FIG. 2A is a graph depicting the performance of various disease classification models created on the subset of miRNA biomarkers selected using a significance-based filter. The solid dark gray bars denote the sensitivity of the models, the dotted light gray bars denote the specificity of the classification models; the error bars denote 95% confidence intervals.
Figure 2B:
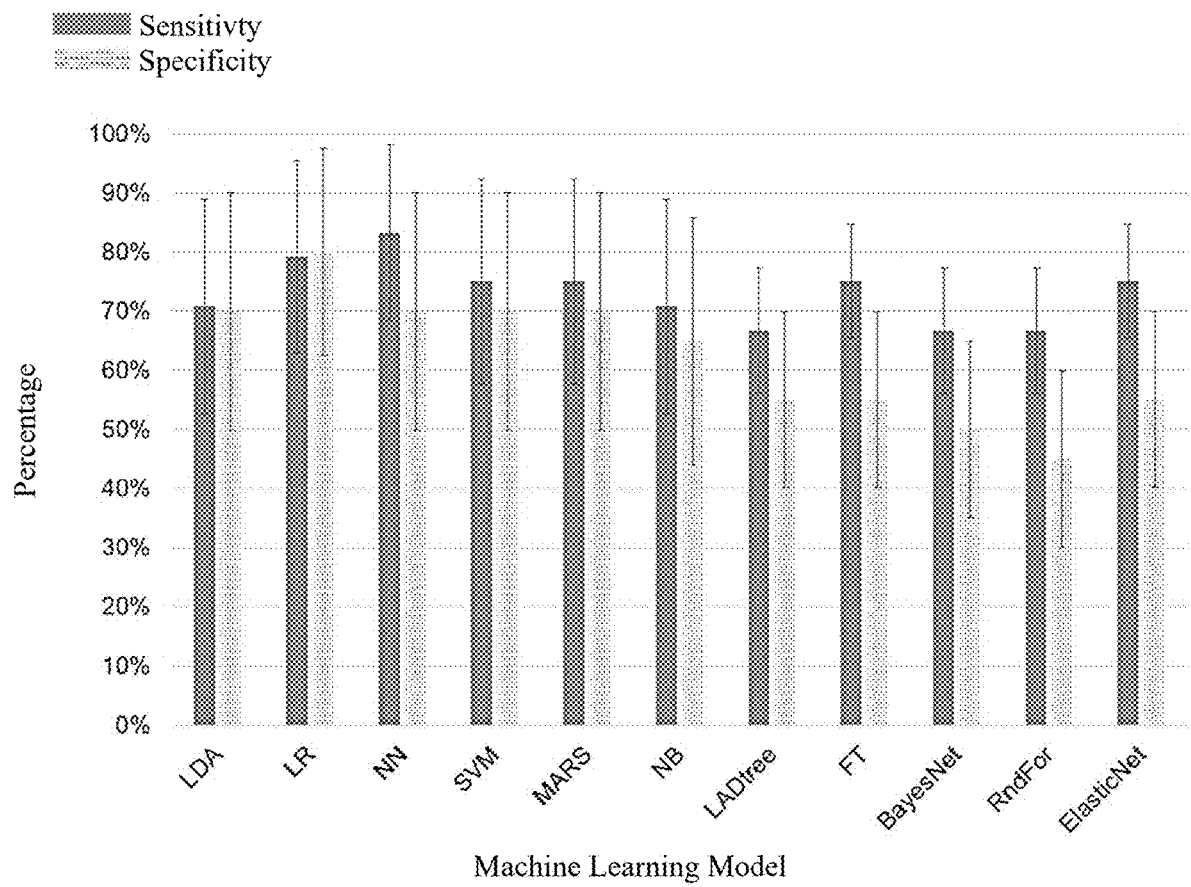
FIG. 2B is a graph depicting the performance of various machine learning models created on the subset of miRNA biomarkers selected using a correlation based feature selection (CFS). The solid dark gray bars denote the sensitivity of the models, the dotted light gray bars denote the specificity of the classification models; the error bars denote 95% confidence intervals.
Figure 2C:
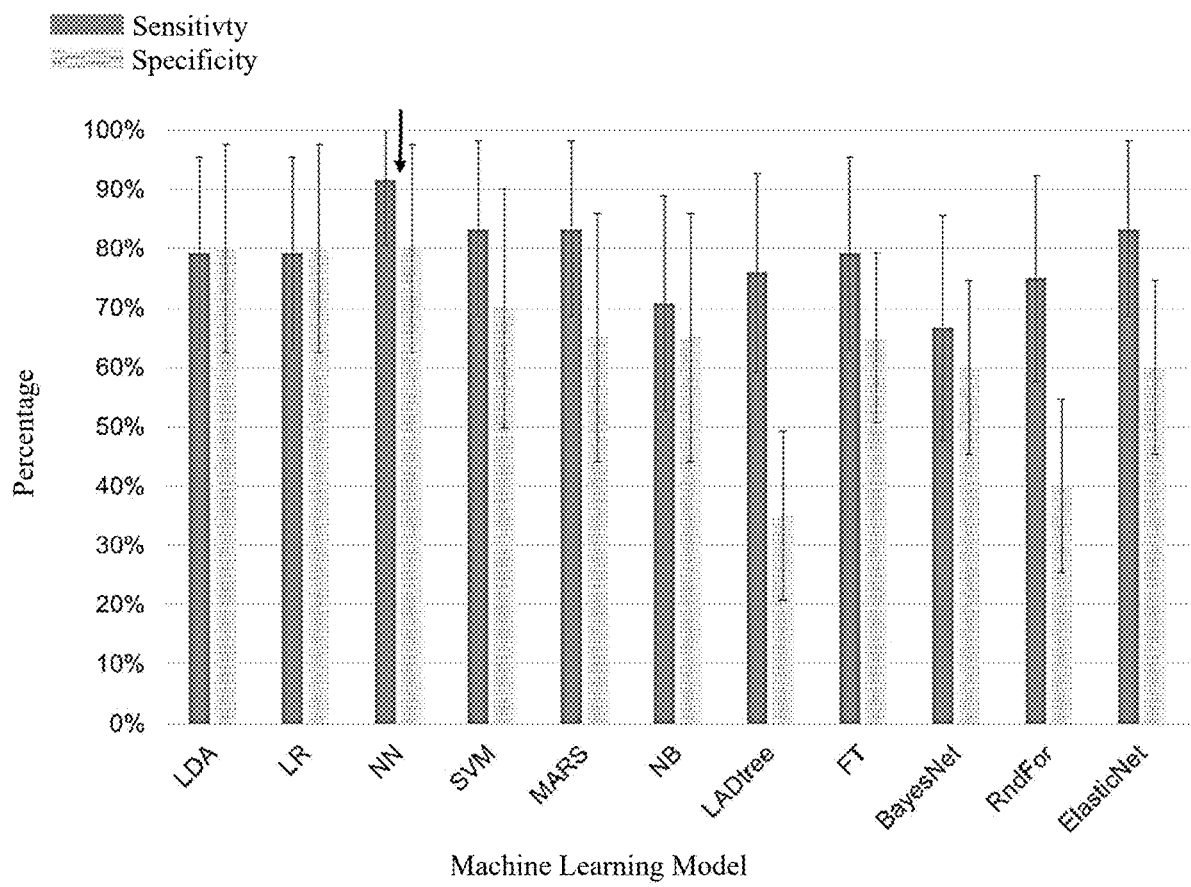
FIG. 2C shows a graph depicting the performance of various machine learning models created on a subset of miRNA biomarkers by a fold change-based filter. The solid dark gray bars denote the sensitivity of the models, the dotted light gray bars denote the specificity of the classification models; the error bars denote 95% confidence intervals. The arrow indicates the neural network analysis using fold change-based filter variables (fourteen miRNA biomarkers).

Values represent receiver operating characteristic (ROC) areas under curves (AUC) 95% confidence intervals shown in parentheses FIGS. 2A-2C each show a graph depicting the performance of the eleven disease classification models; the left-hand bars denote the sensitivity of the classification models, the right-hand bars denote the specificity of the classification models. The whiskers on the bars denote 95% confidence intervals. The graph of FIG. 2A shows the performance of the eleven disease classification models using the miRNA biomarkers selected using the significance-based filter. The graph of FIG. 2B shows the performance of the eleven disease classification models using a CFS subset algorithm. The graph of FIG. 2C shows the performance of the eleven disease classification models using the fold change-based filter. The arrow in FIG. 2C indicates the model with the largest sensitivity and specificity performance characteristics, which is the neural network analysis using the fourteen miRNA biomarkers (see biomarker listing in Table 4 above and Table 6 below).

The optimal machine learning algorithm proved to be a neural network analysis employing miRNA fold changes with a ROC AUC of 0.90 (95% CI: 0.81-0.99) (see arrow in FIG. 2C). This network was selected as the best among 5000 different neural networks constructed for each variable selection method (for a total of 15,000 different neural networks) through empirical optimization of the number of hidden layer neurons used and their activation functions. The network consisted of the fourteen individual miRNAs listed in Table 6 below.

TABLE 6

Fourteen miRNA biomarkers using fold changes in neural network algorithm

| SEQ ID NO. | MicroRNA miRBase ID | Sequence |
|---|---|---|
| 29 | hsa-miR-23b-3p | AUCACAUUGCCAGGGAUUACC |
| 39 | hsa-miR-29a-3p | UAGCACCAUCUGAAAUCGGUUA |
| 46 | hsa-miR-32-5p | UAUUGCACAUUACUAAGUUGCA |
| 47 | hsa-miR-92a-3p | UAUUGCACUUGUCCCGGCCUGU |
| 83 | hsa-miR-150-5p | UCUCCCAACCCUUGUACCAGUG |

TABLE 6-continued

Fourteen miRNA biomarkers using fold changes in neural network algorithm

| SEQ ID NO. | MicroRNA miRBase ID | Sequence |
|---|---|---|
| 104 | hsa-miR-200a-3p | UAACACUGUCUGGUAACGAUGU |
| 105 | hsa-miR-200c-3p | UAAUACUGCCGGGUAAUGAUGGA |
| 106 | hsa-miR-203a-5p | GUGAAAUGUUUAGGACCACUAG |
| 115 | hsa-miR-320c | AAAAGCUGGGUUGAGAGGGU |
| 116 | hsa-miR-320d | AAAAGCUGGGUUGAGAGGA |
| 122 | hsa-miR-335-5p | UCAAGAGCAAUAACGAAAAAUGU |
| 149 | hsa-miR-450b-5p | UUUUGCAAUAUGUUCCUGAAUA |

TABLE 6-continued

Fourteen miRNA biomarkers using fold
changes in neural network algorithm

| SEQ ID NO. | MicroRNA miRBase ID | Sequence |
|---|---|---|
| 178 | hsa-miR-1246 | AAUGGAUUUUUGGAGCAGG |
| 182 | hsa-miR-1307-5p | UCGACCGGACCUCGACCGGCU |

Seven neurons were used in the hidden layer of the neural network to calculate the prediction. The relationships between individual miRNA species were non-linear, so these relationships would likely have been obscured if a simple hierarchical clustering of the statistically significant miRNAs had been employed from the univariate analysis classifier model.

Figure 3A:
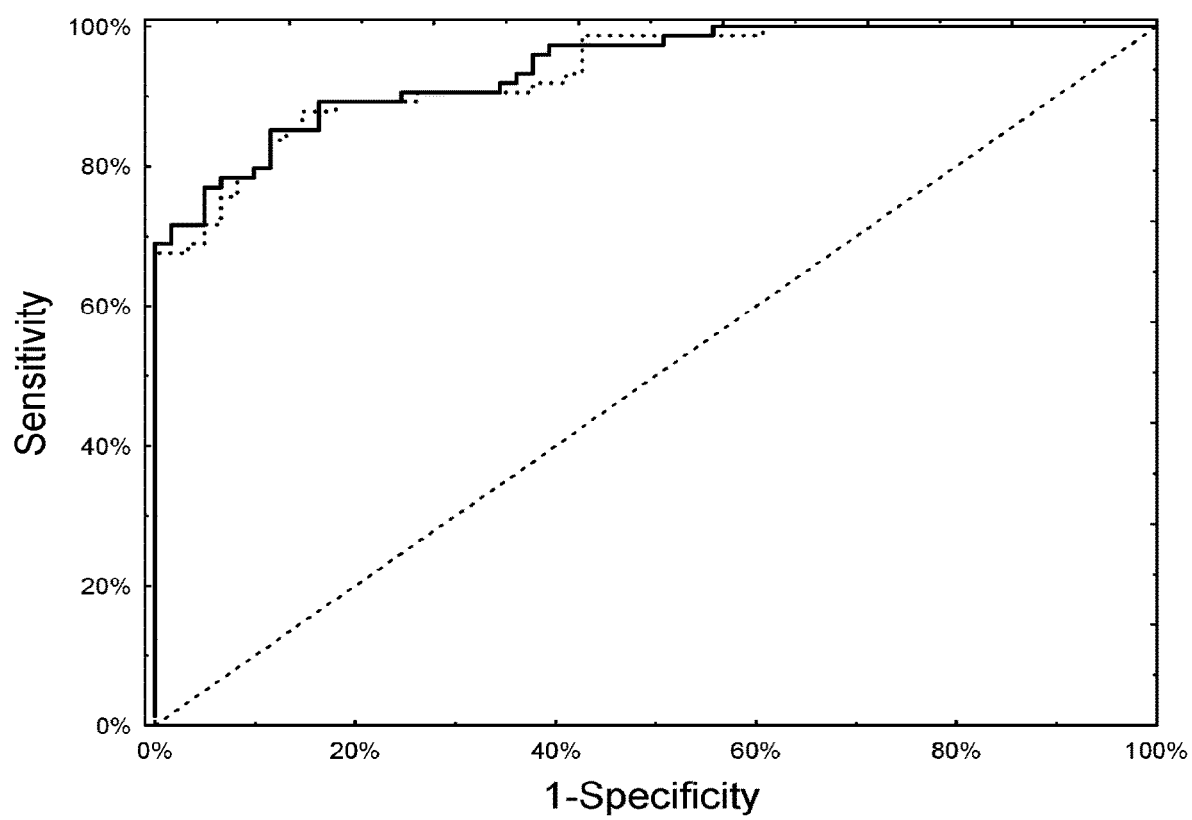
FIG. 3A is a graph of receiver operating characteristic (ROC) curves for a neural network analysis using miRNA biomarkers selected using a fold change-based filter. The ROC curves of FIG. 3A compares the performance of the neural network using fourteen miRNA biomarkers on a training set of raw, non-batch-adjusted data (dotted line) with the performance of the neural network using fourteen miRNA biomarkers on a training set of batch-adjusted data (solid line). The diagonal dashed line represents a classifier without diagnostic utility.
Figure 3B:
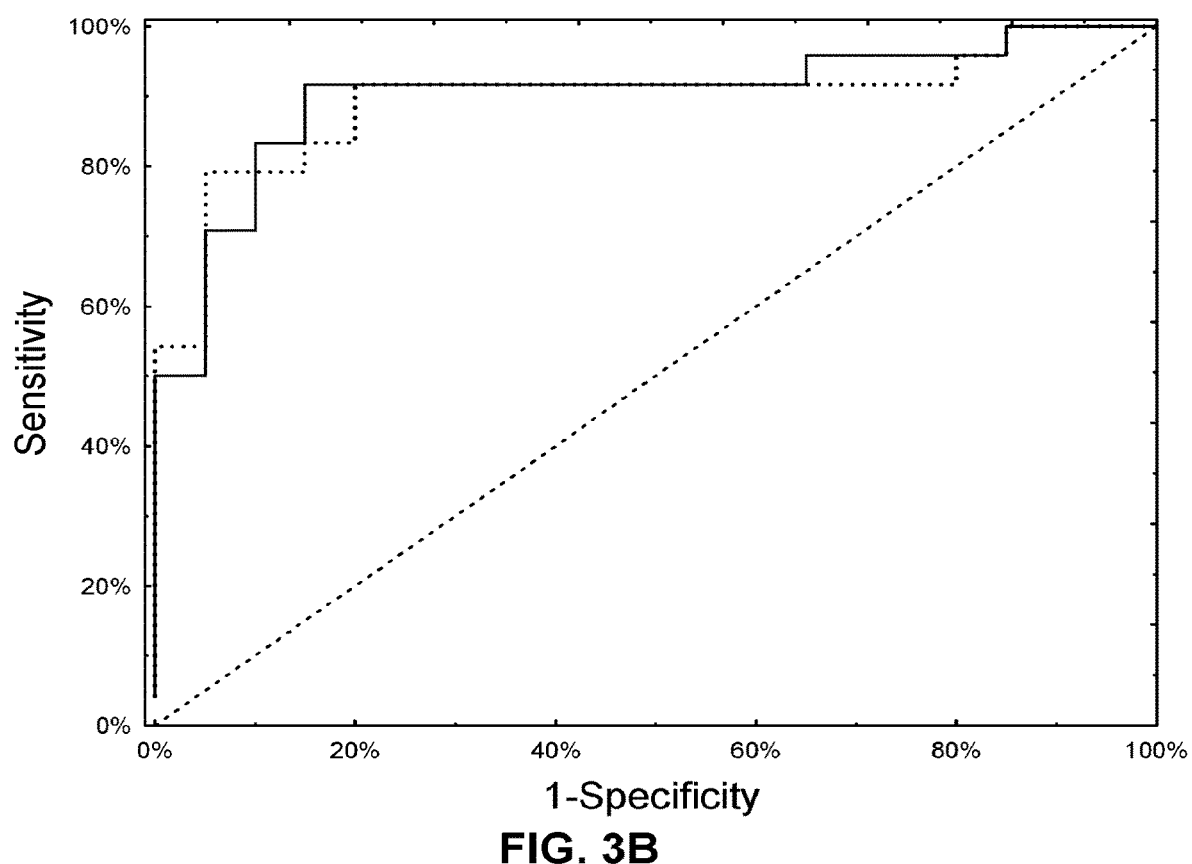
FIG. 3B is a graph of ROC curves for a neural network analysis using fourteen miRNA biomarkers. The ROC curves of FIG. 3B compare the performance of the neural network and fourteen miRNA biomarkers on a testing set of raw non-batch adjusted data (dotted line) with the performance of the neural network and fourteen miRNA biomarkers on a testing set of batch-adjusted data (solid line). The diagonal dashed line represents a classifier without diagnostic utility.

To examine whether the neural network suffered from overfitting or if its performance was due to the batch effect adjustment, the original raw sequencing data was analyzed using the neural network. Based on the fourteen selected miRNAs, the neural network worked equally well on the unadjusted raw datasets, with an AUC of 0.93 (95% CI: 0.89-0.98) in the training set and 0.90 (95% CI 0.80-0.99) in the testing set. FIG. 3A shows a graph of ROC curves, comparing the performance of the neural network on a training set of raw, non-batch-adjusted data (dotted line) with the performance of the neural network on a training set of batch-adjusted data (solid line). FIG. 3B shows a graph of ROC curves comparing the performance of the neural network on a testing set of raw non-batch adjusted data (dotted line) with the performance of the neural network on a testing set of batch-adjusted data (solid line). Again, this approach outperformed all the other classification methods examined.

Example 2: Comparison Between Neural Networks with the CA-125 Biomarker

Figure 4A:
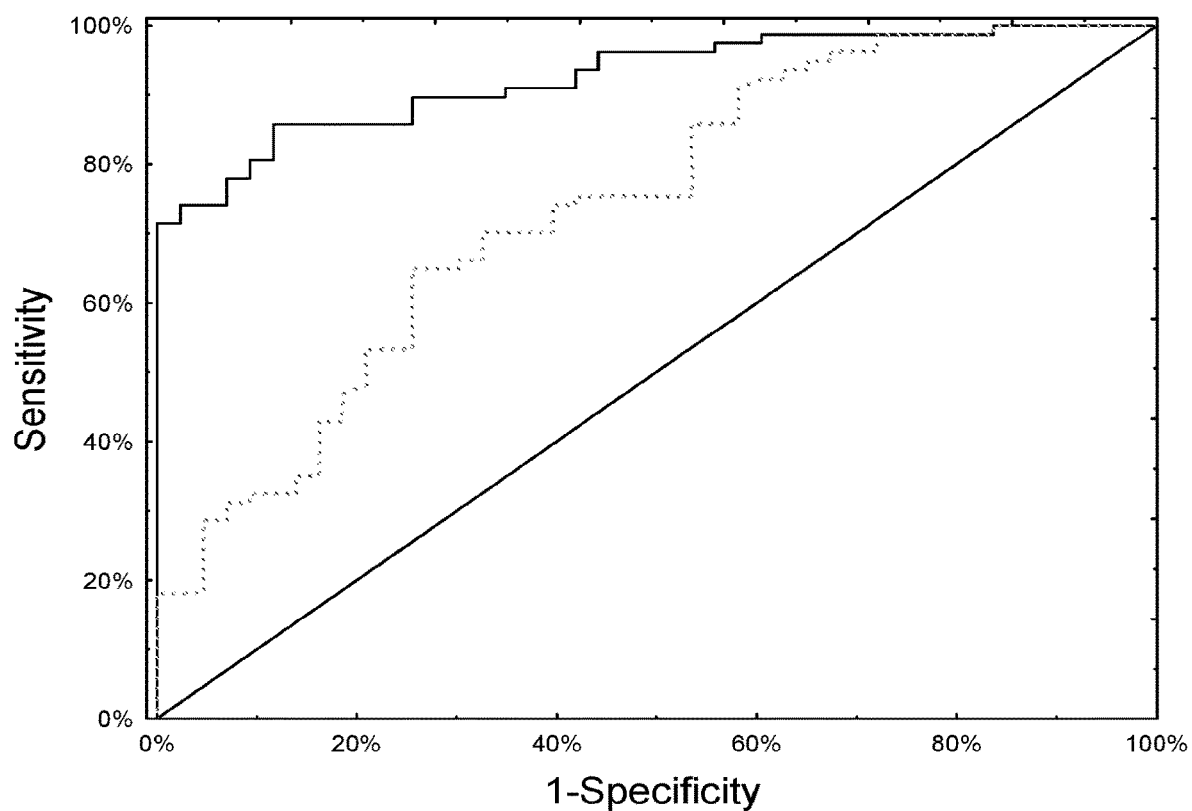
FIG. 4A is a graph of ROC curves comparing the performance of the neural network using a set of fourteen biomarkers (solid line) with the performance of the CA-125 biomarker (dotted line), based on 120 patients. The diagonal line represents a classifier without diagnostic utility.

Next, the fourteen miRNA biomarkers were compared to the classification performance of CA-125. CA-125 is the most common circulating biomarker currently used in the diagnosis of ovarian cancer. While an elevated CA-125 level is a sensitive serum biomarker for advanced serous invasive epithelial ovarian cancer, it misses about 50% of cases of early stage ovarian cancer and non-serous histological type of ovarian cancer. Moreover, CA-125 has limited specificity, particularly for premenopausal women, where it can be elevated in a range of benign conditions, such as pregnancy, endometriosis, and menses. Among the 179 study subjects, preoperative serum CA-125 data was available for 120 patients. CA-125 levels were similarly distributed in the two patient cohorts. The neural network using the selected fourteen miRNA biomarkers (AUC 0.93; 95% CI; 0.88-0.97) outperformed using the single biomarker CA-125 (AUC 0.74; 95% CI 0.65-0.83) in overall operating characteristics for the whole group (p=0.001). FIG. 4A is a graph of ROC curves comparing the performance of the neural network using a set of the selected fourteen biomarkers (solid line) with the performance of the CA-125 biomarker (dotted line), based on 120 patients.

Figure 4B:
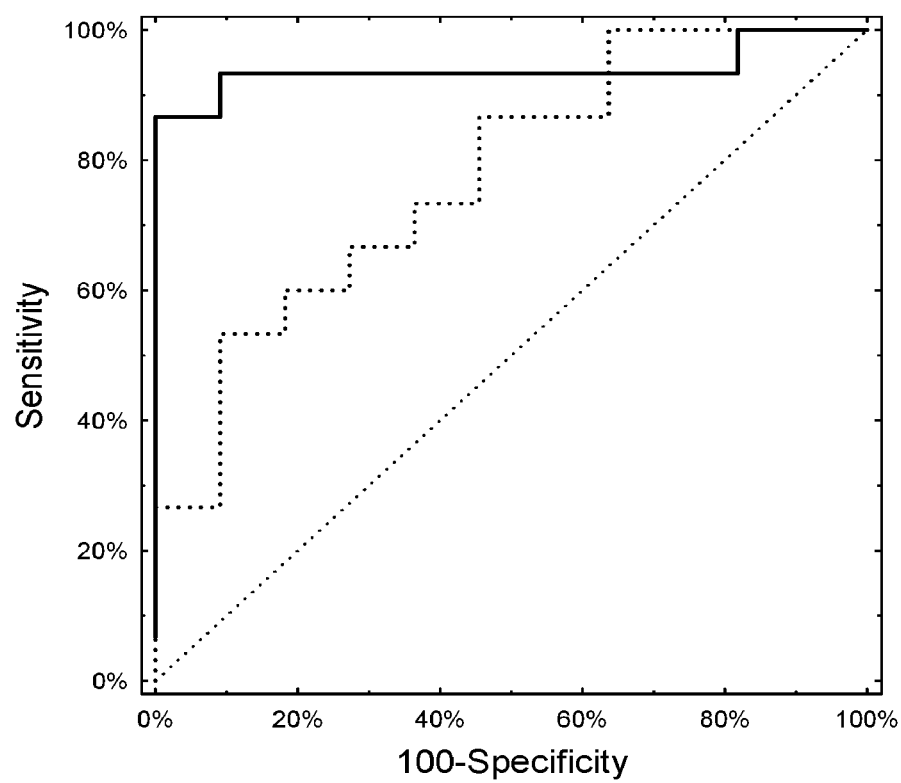
FIG. 4B is a graph of ROC curves comparing the performance of the neural network in classifying ovarian cancer (solid line) with the performance of the CA-125 biomarker (dotted line). The neural network used a set of fourteen biomarkers and a training set (N=94). The diagonal line represents a classifier without diagnostic utility. The neural network using the fourteen miRNA biomarkers has an area under the curve (AUC) of 0.92 (95% CI; 0.87-0.98), while the CA-125 biomarker has an AUC of 0.78 (95% CI; 0.62-0.84).
Figure 4C:
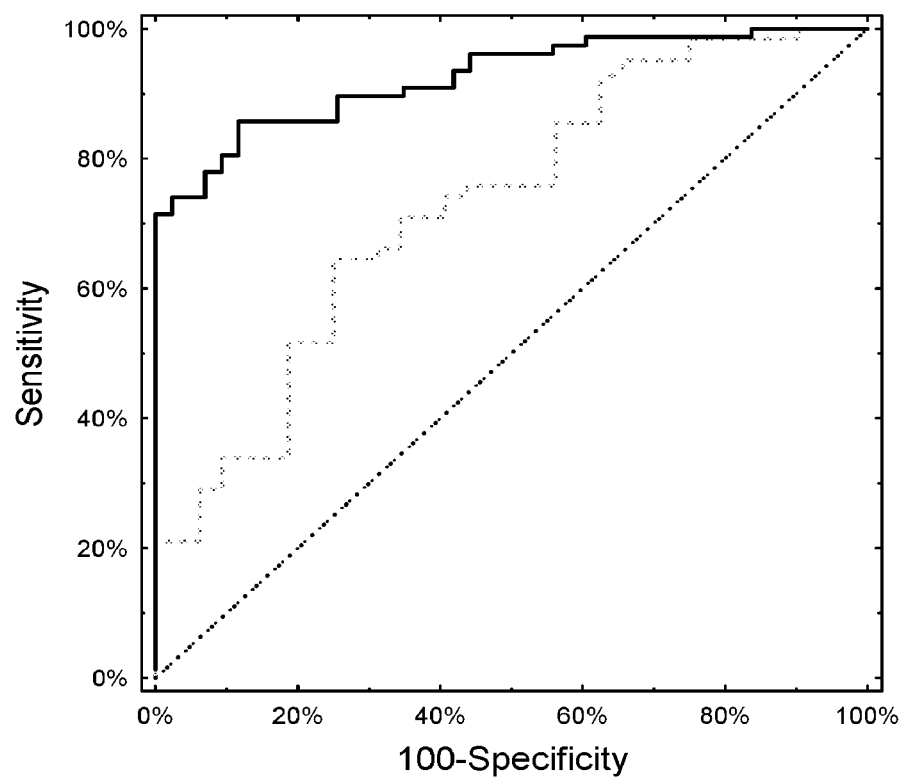
FIG. 4C shows a graph of ROC curves comparing the performance of the neural network in classifying ovarian cancer using a set of fourteen biomarkers (solid line) with the performance of the CA-125 biomarker (dotted line). The neural network used a testing set (N=26). The diagonal line represents a classifier without diagnostic utility. The neural network using the fourteen miRNA biomarkers has an AUC of 0.94 (95% CI; 0.89-0.99), while the CA-125 biomarker has an AUC of 0.78 (95% CI; 0.62-0.84), with p=0.12.

Using the neural network to diagnose patients, the fourteen miRNA biomarkers also outperformed the CA-125 biomarker when the patients were separately analyzed as training and test sets, although dividing the patients into smaller sets reduced the power of the analysis (see FIGS. 4B-4C). FIG. 4B is a graph of ROC curves for the training data set, comparing the performance of the neural network classifying ovarian cancer in patients using the selected fourteen biomarkers (solid line) with the performance of the CA-125 biomarker (dotted line) (N=94). FIG. 4C shows a graph of ROC curves for the testing data set, comparing the performance of the neural network in classifying ovarian cancer using the selected fourteen biomarkers (solid line) with the performance of the CA-125 biomarker (dotted line) (N=26). In the training set (N=94), the fourteen biomarkers had an AUC of 0.92 (95% CI; 0.87-0.98) versus an AUC of 0.73 (95% CI; 0.59-0.96) for CA-125 alone (p=0.0018). In the test set (N=26), the fourteen miRNA biomarkers had an AUC of 0.94 (95% CI 0.89-0.99) versus an AUC of 0.78 (95% CI 0.62-0.84) for CA-125 alone (p=0.12).

The primary advantage of the neural network reliant on the fourteen miRNA biomarkers, over the single biomarker CA-125 is the improved ability to avoid false positives (65% fewer; p=0.002) and to identify more non-serous ovarian cancers (22% more; p=0.002). Table 7 below shows misclassification data for CA-125 and for the neural network prediction using the selected fourteen biomarkers. Notably, the neural network miRNA biomarkers and CA125 levels were independent of one another, as illustrated by the general lack of linear correlations between expression of the fourteen miRNAs used in the network and CA125 levels in cancer and non-cancer cases.

TABLE 7

Misclassification matrices for the neural network and CA-125 predictions with detailed histopathological data

| | CA-125 Prediction | | | Neural Network Prediction | | | p-value |
|---|---|---|---|---|---|---|---|
| Diagnosis | Correct | False Positive | False Negative | Correct | False Positive | False Negative | |
| Other benign mass | 8 | 7 | — | 11 | 4 | — | |
| Endometrioma | 4 | 4 | — | 8 | 0 | — | |
| Cystadenoma | 2 | 1 | — | 2 | 1 | — | |
| Borderline tumors | 6 | 11 | — | 14 | 3 | — | |
| Total false positive rate | 23/43 (53%) | | | 8/43 (19%) | | | 0.002 |
| Stage I/II Invasive Serous Adenocarcinoma | 18 | — | 4 | 19 | — | 3 | |
| Stage III/IV | 21 | — | 1 | 20 | — | 2 | |

TABLE 7-continued

Misclassification matrices for the neural network and
CA-125 predictions with detailed histopathological data

| | CA-125 Prediction | | | Neural Network Prediction | | | |
|---|---|---|---|---|---|---|---|
| Diagnosis | Correct | False Positive | False Negative | Correct | False Positive | False Negative | p-value |
| Invasive Serous Adenocarcinoma | | | | | | | |
| Total false negative rate | | 5/44 (11%) | | | 5/44 (11%) | | 1.0 |
| Stage I/II Invasive Clear Cell/Endometrioid Adenocarcinoma | 11 | — | 7 | 14 | — | 4 | |
| Stage III/IV Invasive Clear Cell/Endometrioid Adenocarcinoma | 7 | — | 1 | 8 | — | 0 | |
| Total false negative rate | | 8/26 (31%) | | | 4/26 (15%) | | 0.002 |
| Invasive cancer (other histologies) | 4 | — | 3 | 5 | — | 2 | |
| Total false negative rate | | 3/7 (43%) | | | 2/7 (29%) | | 1.0 |

Correct—accurate classification as benign, borderline or control versus invasive cancer
False positive—incorrectly assigned benign, borderline or control to invasive cancer
False negative—incorrectly assigned invasive cancer to benign, borderline or control

Figure 5A:
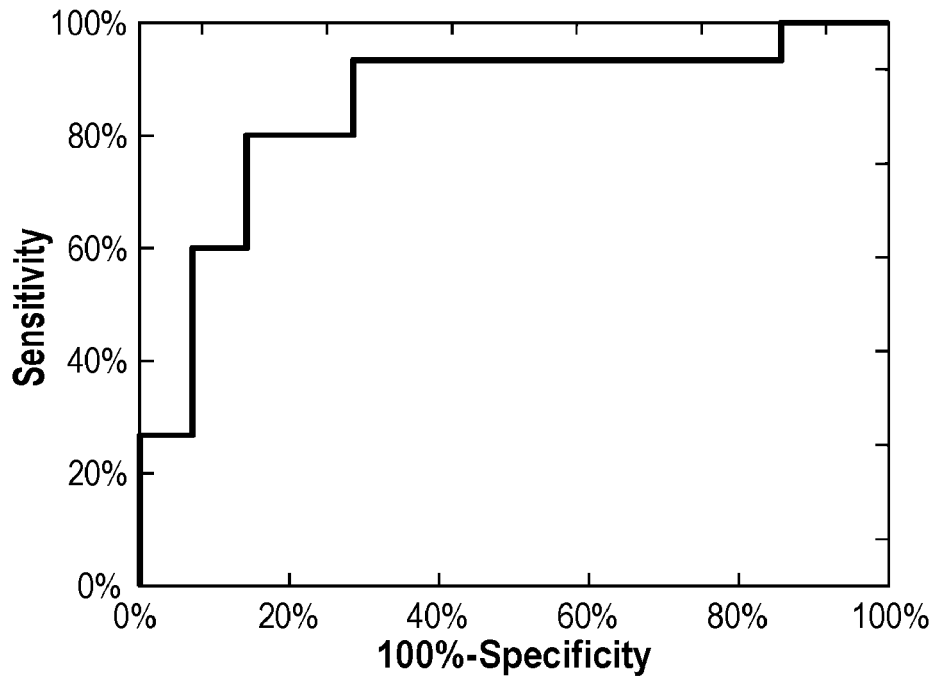
FIG. 5A is a graph of ROC curves for neural network analysis of qPCR data using a fourteen miRNA signature with minimal values imputed for undetectable miRNAs.

Example 3: Neural Networks for Identifying Ovarian Cancer Patients Using miRNA qPCR Data It was important to know whether the miRNAs selected would only identify invasive ovarian cancer cases using sequencing data, or if the miRNA biomarker signature would be as robust if a different type of input for miRNA quantification was used. To validate the algorithm on a second platform, the expression levels of the fourteen miRNAs were measured (as well as an additional nine reference miRNAs derived from the sequencing data) by quantitative PCR (qPCR), and then repeated using the neural network construction. This produced a ROC curve (see FIG. 5A) with an AUC of 1.00 (95% CI; 1.00-1.00) on the training set and an AUC of 0.85 (95% CI; 0.71-0.99) on the testing set, respectively. FIG. 5A depicts a graph of ROC curves for the neural network analysis of qPCR data using the fourteen miRNA signature with minimal values imputed for undetectable miRNAs. As qPCR has a lower sensitivity than sequencing, miRNA values were undetectable for some miRNAs in some samples using this technique. This might account for a lower AUC for the testing set using qPCR than had been observed when using sequencing data.

To minimize the impact of missing data points on classifier performance, a global sensitivity analysis was performed on the best neural network for qPCR data, and the variables which contributed the least to the classifier's performance were iteratively removed. Following this analysis, the number of miRNAs used by the neural network was reduced to seven, listed below in Table 8.

TABLE 8

Seven miRNA biomarkers used in the final neural network model reliant on qPCR data

| SEQ ID NO. | MicroRNA miRBase ID | Sequence |
|---|---|---|
| 39 | hsa-miR-29a-3p | UAGCACCAUCUGAAAUCGGUUA |
| 47 | hsa-miR-92a-3p | UAUUGCACUUGUCCCGGCCUGU |
| 105 | hsa-miR-200c-3p | UAAUACUGCCGGGUAAUGAUGGA |
| 115 | hsa-miR-320c | AAAAGCUGGGUUGAGAGGGU |
| 122 | hsa-miR-335-5p | UCAAGAGCAAUAACGAAAAAUGU |
| 149 | hsa-miR-450b-5p | UUUUGCAAUAUGUUCCUGAAUA |
| 182 | hsa-miR-1307-5p | UCGACCGGACCUCGACCGGCU |

Figure 5B:
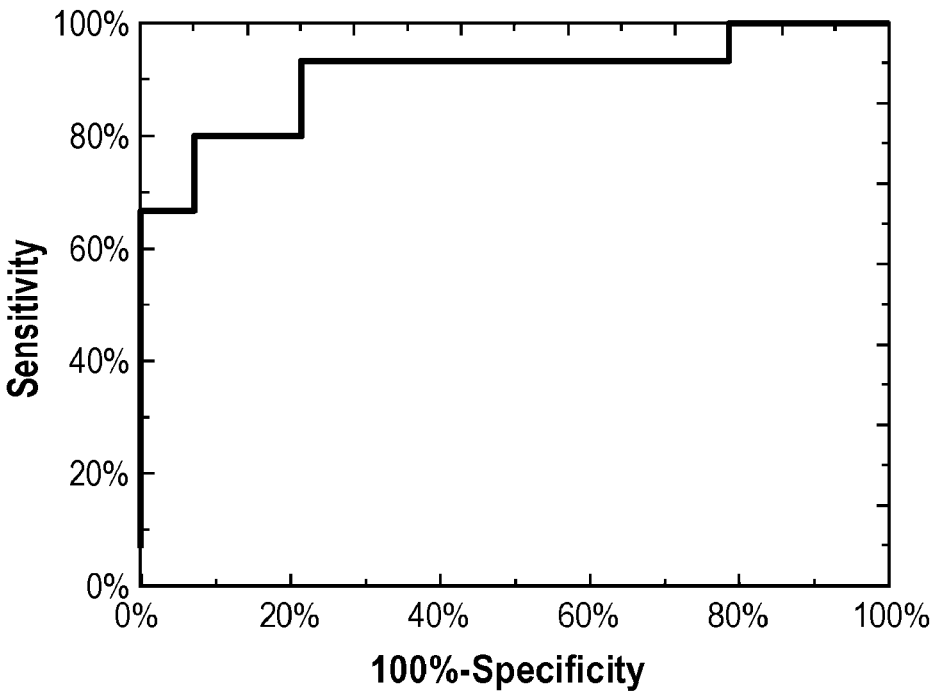
FIG. 5B is a graph of ROC curves for neural network analysis of qPCR data built on a seven miRNA signature after a global sensitivity analysis.

The number of normalizers used with these seven miRNAs was reduced to two: hsa-miR-423-3p (SEQ ID NO: 142) and hsa-miR-103a-3p (SEQ ID NO: 55), selected using the NormFinder method (see Materials and Methods below). The resulting network was composed of four neurons in the hidden layer maintained the performance of the miRNA sequence and qPCR-based networks, with an ROC AUC of 0.97; (95% CI; 0.91-1.00) on the training set, and a ROC AUC of 0.91 (95% CI; 0.85-1.00) on the testing set, while being a more robust tool with simpler input requirements. FIG. 5B is a graph of ROC curves for neural network analysis of qPCR data built on a seven miRNA signature after a global sensitivity analysis.

Example 4: External Validation of qPCR

Figure 6:
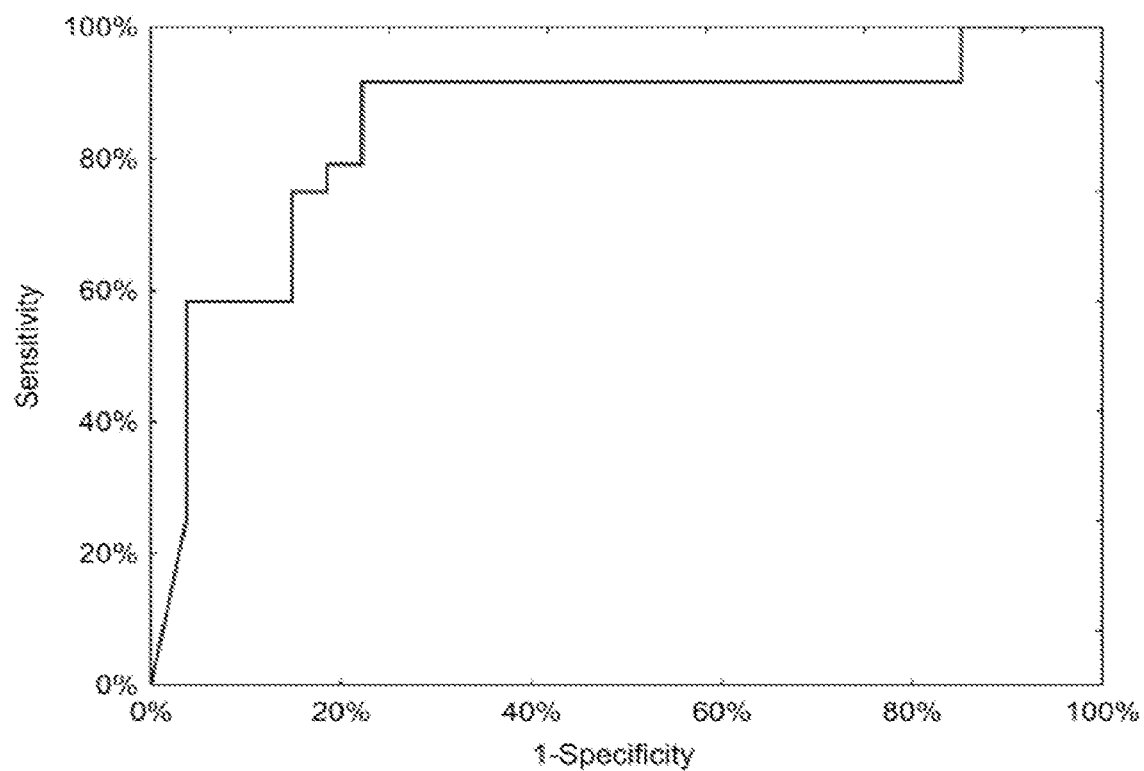
FIG. 6 is a ROC curve for neural network analysis using qPCR inputs from an different clinical test set gathered in Poland.
Figure 7A:
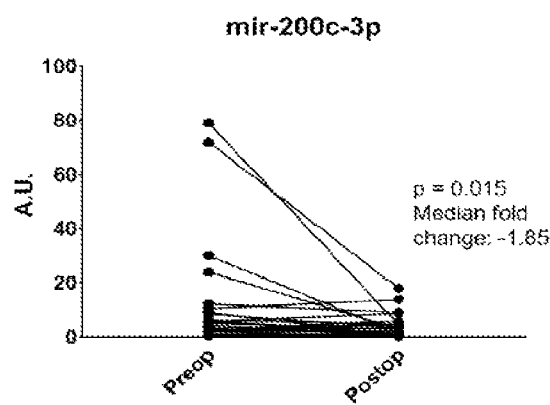
FIG. 7A is a line graph of change in mir-200c-3p expression in blood samples from patients both before and after surgical cytoreduction.
Figure 7B:
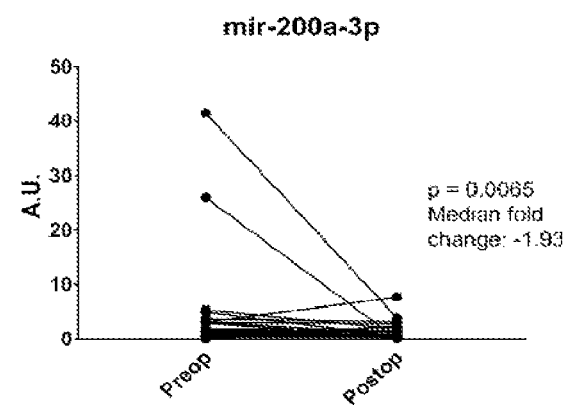
FIG. 7B is a line graph of change in mir-200a-3p expression in blood samples from patients both before and after surgical cytoreduction.
Figure 7C:
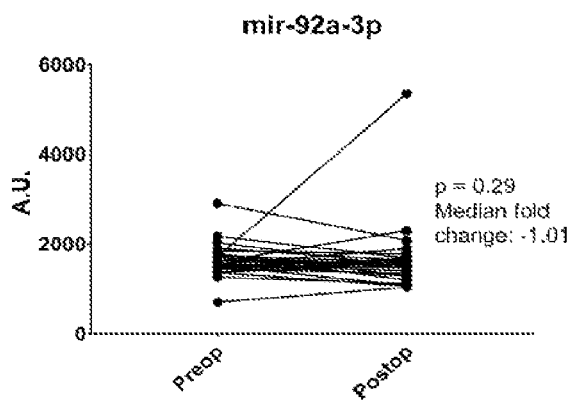
FIG. 7C is a line graph of change in mir-92a-3p expression in blood samples from patients both before and after surgical cytoreduction.
Figure 7D:
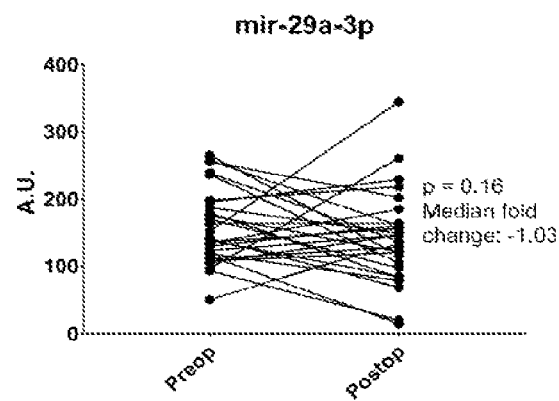
FIG. 7D is a line graph of change in mir-29a-3p expression in blood samples from patients both before and after surgical cytoreduction.

The clinical performance of the final, locked-down diagnostic test was then tested on a completely independent external sample set collected from 51 preoperative patients treated in Lodz, Poland (see Table 9 below for clinical characteristics of the external validation set). In this population, the neural network had a positive predictive value of 91.3% (95% CI:73.3-97.6%) and a negative predictive value of 78.6% (95% CI: 64.2-88.2%) with an AUC of 0.85 (see FIG. 6 for ROC AUC curve).

TABLE 9

Clinical Characteristics of the external validation set

| Characteristic | Polish external validation set (n = 51) |
|---|---|
| Age, years, median (SD) † | 55.5 (16.1) |
| Grade, n (%)‡ | |
| Borderline | 4 (7.8) |
| 1 | 2 (3.9) |
| 2 | 7 (13.7) |
| 3 | 13 (25.5) |
| Unspecified | 3 (5.9) |
| Benign | 22 (43.1) |
| FIGO Stage, n (%)‡ | |
| I | 7 (13.7) |
| II | 3 (5.9) |
| III | 18 (35.3) |
| IV | 1 (2.0) |
| Benign | 22 (43.1) |
| Histology, n (%) | |
| Serous cystadenoma/cystadenofibroma | 6 (11.8) |
| Endometrioma/endometriosis | 10 (19.6) |
| Mature teratoma | 6 (11.8) |
| Borderline serous tumor | 2 (3.9) |
| Borderline seromucinous tumor | 2 (3.9) |
| Serous adenocarcinoma | 4 (7.8) |
| Mucinous adenocarcinoma | 1 (2.0) |
| Endometrioid adenocarcinoma | 1 (2.0) |
| Clear Cell Adenocarcinoma | 9 (17.6) |
| Mixed adenocarcinoma | 3 (5.9) |
| Adenocarcinoma unspecified | 7 (13.7) |

Ideally, a serum biomarker should have biologic relevance to the clinical disease. To assess biologic relevance, the expression levels of the miRNAs from the ERASMOS patient set were examined to determine any changes in the cancer patients after surgical cytoreduction. Among the patients with ovarian cancer in the study, 27 had both preoperative and postoperative serum miRNAs profiled. These included 4/7 target miRNAs in the qPCR neural network model. Circulating levels of all three miRNAs decreased within 72 hr of tumor removal, with significant changes for miR-200a-3p and miR-200c-3p (see FIGS. 7A-7D).

Figure 8:
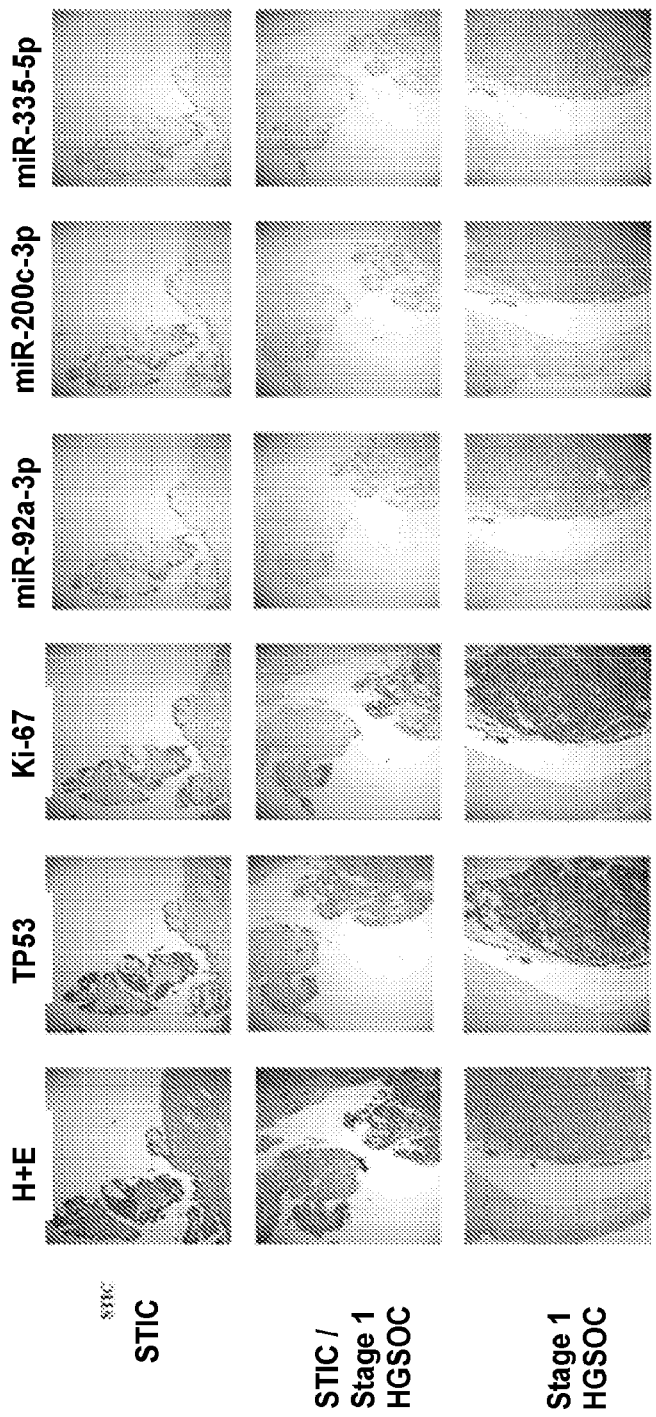
FIG. 8 is a series of photomicrographs showing in situ expression of selected miRNAs from a serum signature in sections of fallopian tubes showing serous tubal intraepithelial carcinoma (STIC) lesions and Stage I high grade serous ovarian cancer (HGSOC). Lesional cells are indicated by TP53 and Ki-67 staining.

To test if the miRNAs were in fact coming from the earliest lesions of this disease, paraffin-embedded tissue sections were assembled from independent sets of 15 cases of serous tubal intraepithelial carcinomas and 15 Stage I high grade (serous or Grade three endometrioid) epithelial ovarian cancers. Immunohistochemistry was performed on sequential sections for TP53 and Ki67 to highlight the lesions. In situ hybridization was then performed for three of the miRNAs in the neural network; mir-200c-3p, mir-335-5 p, and mir-92a-3p (see FIG. 8). FIG. 8 shows a series of photomicrographs taken at 10×, showing in situ expression of selected miRNAs from a serum signature, in sections of fallopian tubes showing serous tubal intraepithelial carcinoma (STIC) lesions and Stage I high grade serous ovarian cancer (HGSOC). Lesional cells are indicated by TP53 and Ki-67 staining. The top row of photomicrographs shows STIC lesion in continuity with normal fallopian tube at 20×. The middle row of photomicrographs shows STIC lesions in continuity with normal fallopian tube and invasive cancer with p53-null lesion at 10×. The bottom row of photomicrographs shows HGSOC intraluminal to the fallopian tube at 10×. The first column of photomicrographs (far left side) shows sections stained with hematoxylin and eosin (H+E); the second column shows staining for TP53; the third column shows staining for Ki-67. The fourth, fifth and sixth columns show in situ hybridization for three different markers (miR-92a-3p, miR-200c-3-, and miR-335-5p, respectively).

In 100% of the samples, there was complete overlap between lesional cells and the miRNAs crucial for neural network performance, indicating that the miRNAs detected in the serum are present even in early lesions in the fallopian tube epithelium, and that pre-metastatic disease can be detected.

Example 5: Neural Networks for Identifying Ovarian Cancer Patients Using miRNA Microarray Data For external validation of the fourteen miRNA signature, both the miRNA signature and the neural network algorithm were tested on an independent, publicly available dataset previously published by Keller, et al. (Keller, A. et al. (2011) Toward the blood-borne miRNome of human diseases. Nat Methods 8, 841-843). In that study, the authors collected blood samples from 454 individuals, among whom 15 had ovarian cancer and 70 were healthy controls. The data were generated using a probe-based microarray, which contained all fourteen miRNAs from the signature described above, allowing for one-to-one mapping of the fourteen microRNAs without any exclusion. Data were normalized as in the original manuscript by Keller, et al. The dataset was divided randomly into a training set and a testing set, using a 70:30 ratio. A neural network was developed using the fourteen miRNA signature to differentiate patients with cancer from controls. Using the original miRNA-sequence data set from Keller et al. (GSE31568 accession to the Gene Expression Omnibus database), 5000 networks were generated using the same protocol described herein, with the five best networks manually assessed for their complexity and performance.

The best neural network in terms of highest performance and lowest complexity had four neurons in the hidden layer. This neural network perfectly classified patients in the training set (AUC 1.00, 95% CI; 1.00-1.00) and provided good discriminatory power on the testing set (AUC 0.93, 95% CI; 0.81-1.00), with an overall sensitivity of 75% and specificity of 100%. Since the Keller dataset included a variety of other non-ovarian cancer diagnoses, the algorithm using the fourteen biomarker signature was analyzed to determine whether the algorithm was specific to ovarian cancer or would identify individuals with six other cancer types or six benign diagnoses.

Figure 9:
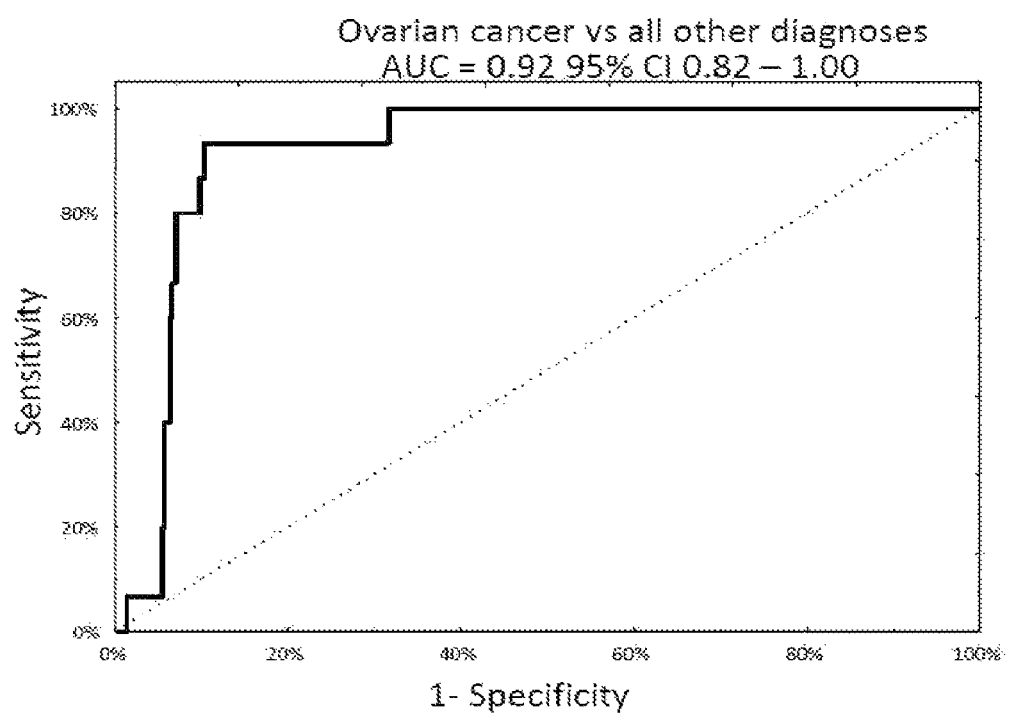
FIG. 9 is a graph of an ROC curve showing that in a cohort of 454 patient samples with a wide array of medical diagnoses, including 70 healthy controls, a fourteen miRNA signature accurately identifies ovarian cancer cases against all other diagnoses (i.e. healthy controls or other cancers). The diagonal line represents a classifier without diagnostic utility.

FIG. 9 depicts a ROC curve showing that in the Keller et al. cohort of 454 patient samples with a wide array of medical diagnoses, including 70 healthy controls, a fourteen miRNA signature accurately identifies ovarian cancer cases against all other diagnoses (i.e. healthy controls or other cancers). This dataset is deposited in the Gene Expression Omnibus database (ncbi.nlm.nih.gov/geo/) under entry number GSE31568.

Figure 10A:
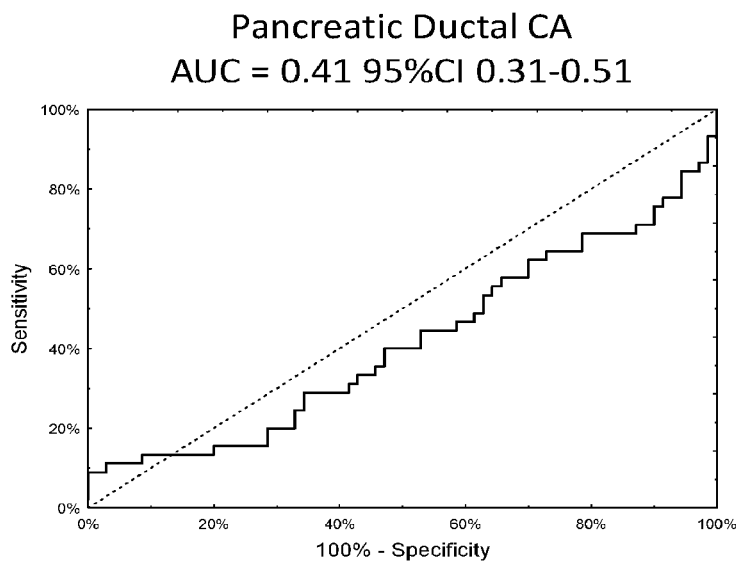
FIG. 10A is a graph of a ROC curve of a fourteen miRNA signature for ovarian cancer compared with pancreatic ductal cancer in a certain dataset. The diagonal line represents a classifier without diagnostic utility.
Figure 10B:
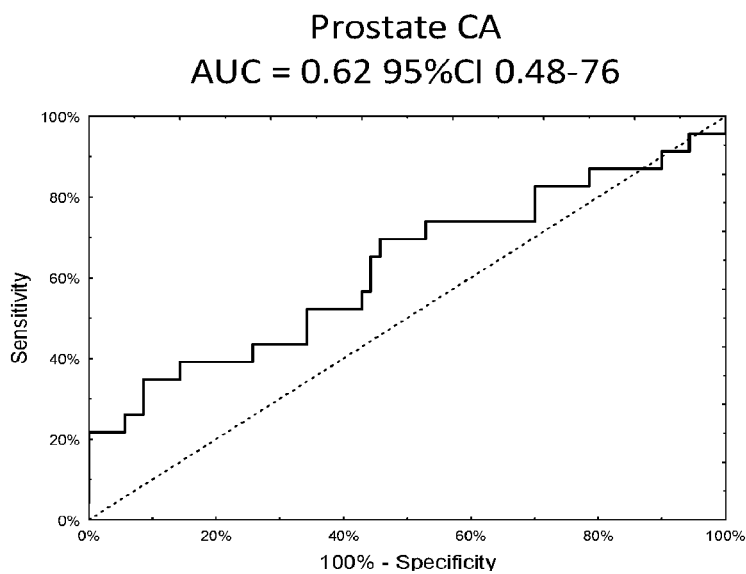
FIG. 10B is a graph of a ROC curve of a fourteen miRNA signature for ovarian cancer compared with other prostate cancer in a certain dataset. The diagonal line represents a classifier without diagnostic utility.
Figure 10C:
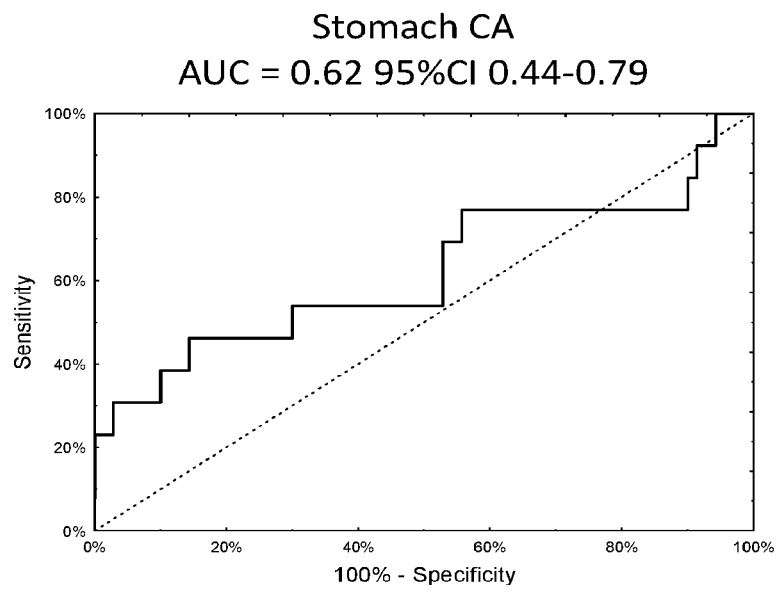
FIG. 10C is a graph of a ROC curve of a fourteen miRNA signature for ovarian cancer compared with stomach cancer in a certain dataset. The diagonal line represents a classifier without diagnostic utility.
Figure 10D:
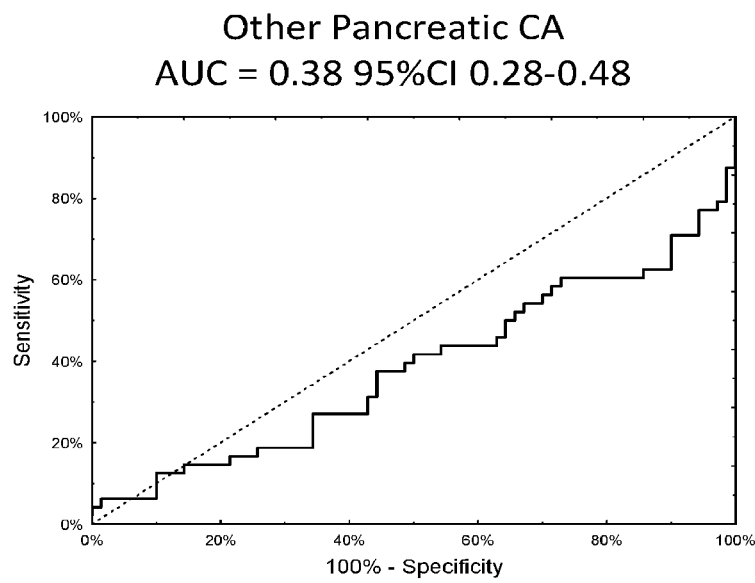
FIG. 10D is a graph of a ROC curve of a fourteen miRNA signature for ovarian cancer compared with pancreatic cancer in a certain dataset. The diagonal line represents a classifier without diagnostic utility.
Figure 10E:
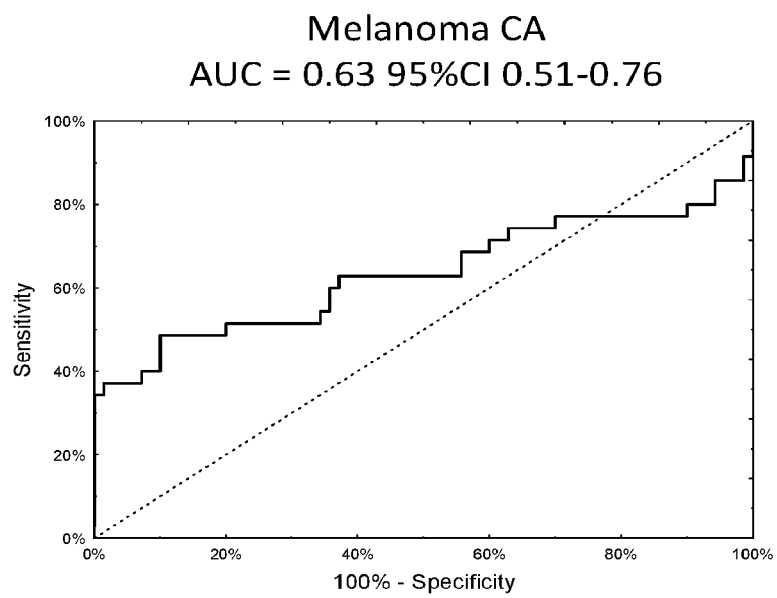
FIG. 10E is a graph of a ROC curve of a fourteen miRNA signature for ovarian cancer compared with melanoma in a certain dataset. The diagonal line represents a classifier without diagnostic utility.
Figure 10F:
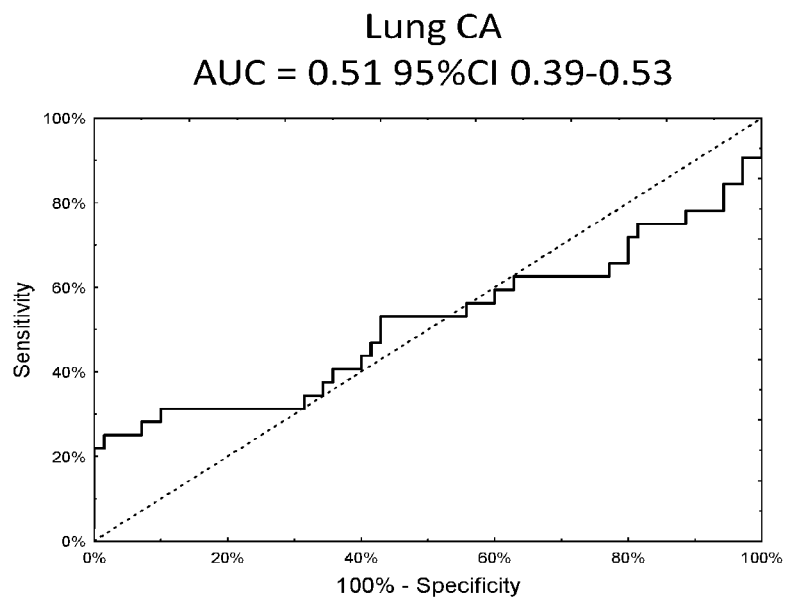
FIG. 10F is a graph of a ROC curve of a fourteen miRNA signature for ovarian cancer compared with lung cancer in a certain dataset. The diagonal line represents a classifier without diagnostic utility.
Figure 10G:
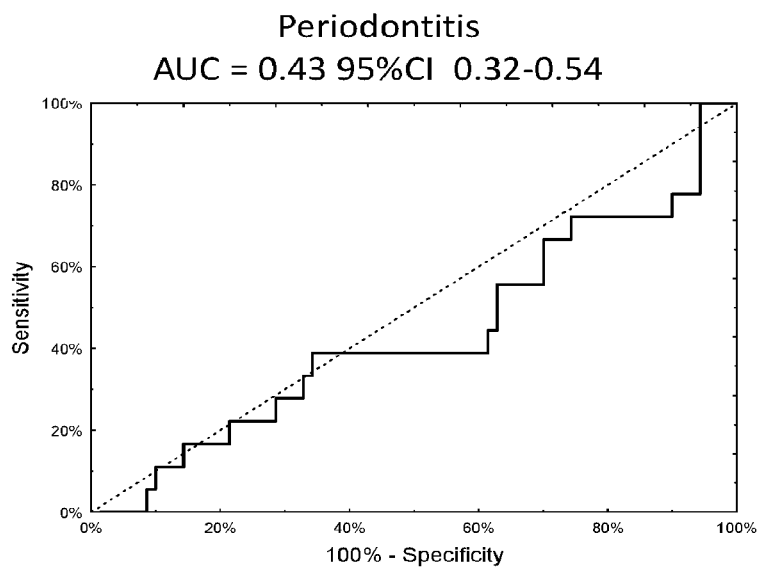
FIG. 10G is a graph of a ROC curve of a fourteen miRNA signature for ovarian cancer compared with periodontitis in a certain dataset. The diagonal line represents a classifier without diagnostic utility.
Figure 10H:
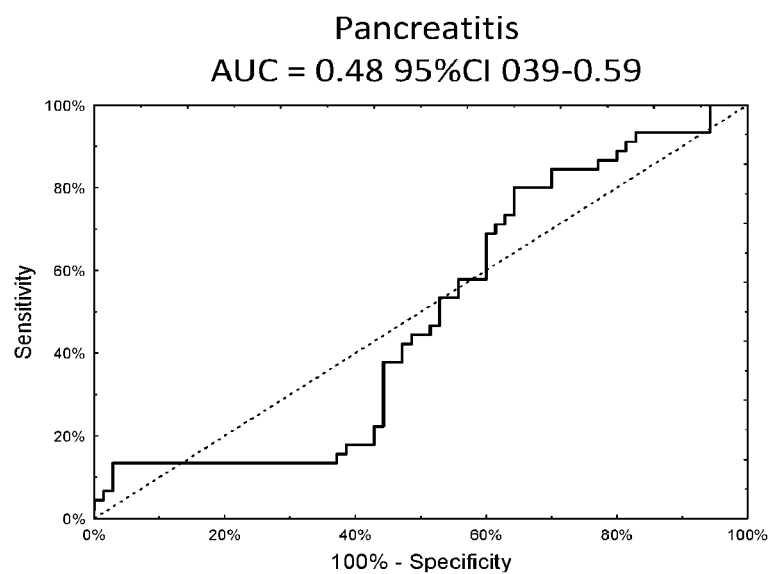
FIG. 10H is a graph of a ROC curve of a fourteen miRNA signature for ovarian cancer compared with pancreatitis in a certain dataset. The diagonal line represents a classifier without diagnostic utility.
Figure 10I:
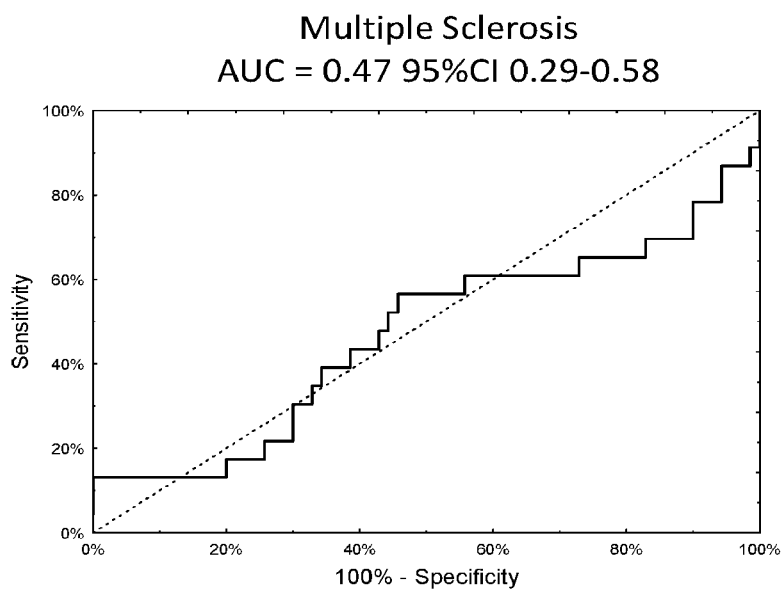
FIG. 10I is a graph of a ROC curve of a fourteen miRNA signature for ovarian cancer compared with multiple sclerosis in a certain dataset. The diagonal line represents a classifier without diagnostic utility.
Figure 10J:
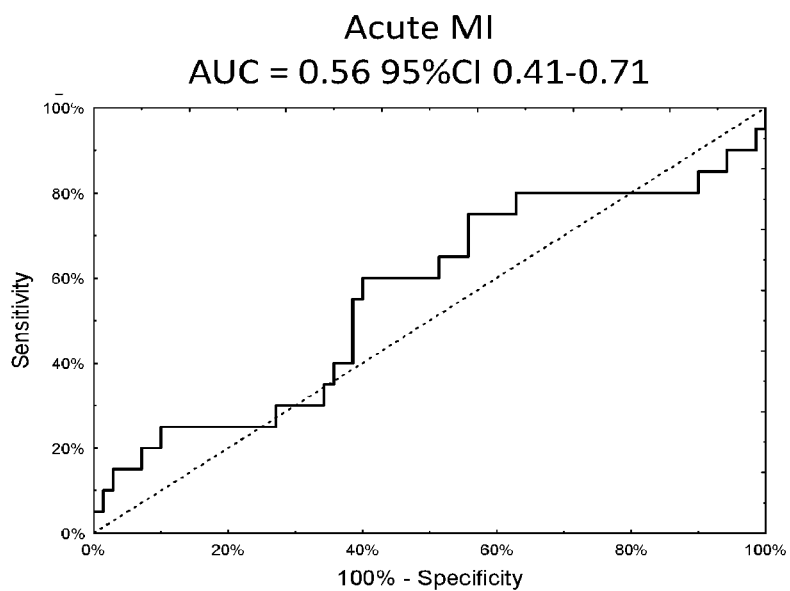
FIG. 10J is a graph of a ROC curve of a fourteen miRNA signature for ovarian cancer compared with acute myocardial infarction (MI) in a certain dataset. The diagonal line represents a classifier without diagnostic utility.
Figure 10K:
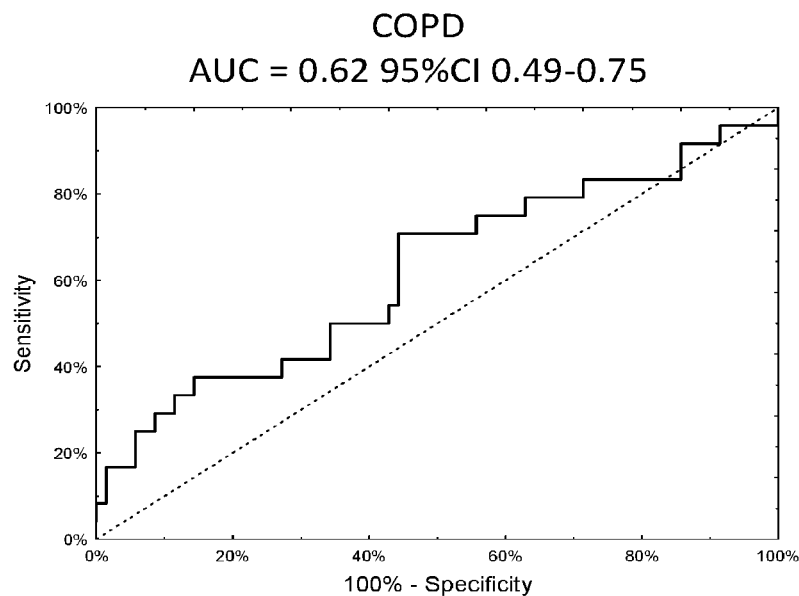
FIG. 10K is a graph of a ROC curve of a fourteen miRNA signature for ovarian cancer compared with chronic obstructive pulmonary disease (COPD) in a certain dataset. The diagonal line represents a classifier without diagnostic utility.
Figure 10L:
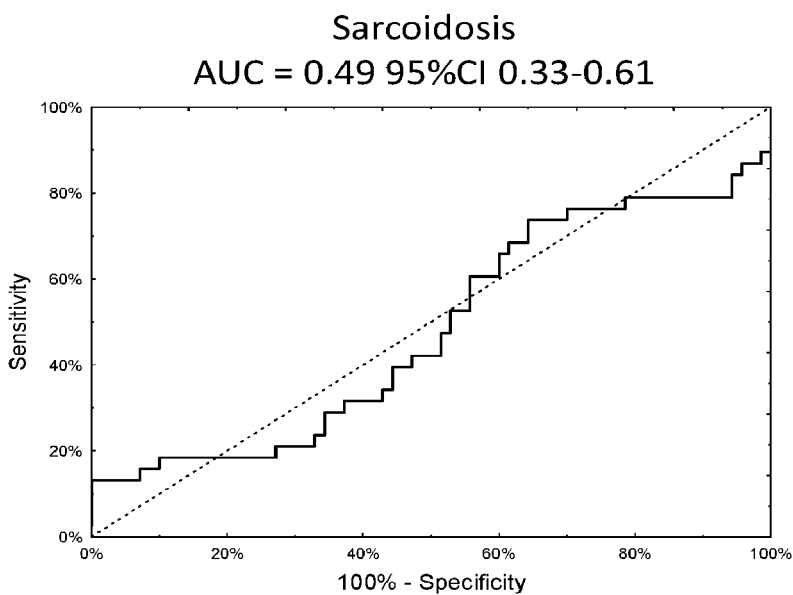
FIG. 10L is a graph of a ROC curve of a fourteen miRNA signature for ovarian cancer compared with sarcoidosis in a certain dataset. The diagonal represents a classifier without diagnostic utility.

The fourteen miRNA signature was found to be unique to ovarian cancer over a variety of conditions, including pancreatic ductal cancer, other pancreatic cancer, prostate cancer, stomach cancer, melanoma, lung cancer, periodontitis, pancreatitis, multiple sclerosis, acute myocardial infarction, chronic obstructive pulmonary disease, and sarcoidosis. The neural network 14 miRNA signature did not separate any other diagnoses from the control group in the published dataset by Keller. The number of subjects (n) denotes the number of cases of the given diagnosis in the Keller dataset as follows: pancreatic ductal cancer (n=45; FIG. 10A); prostate cancer (n=23; FIG. 10B); stomach cancer (n=13; FIG. 10C); other pancreatic cancers (n=48; FIG. 10D); melanoma (n=35; FIG. 10E); lung cancer (n=32; FIG. 10F); periodontitis (n=18; FIG. 10G); pancreatitis (n=38; FIG. 10H); multiple sclerosis (n=23; FIG. 10O; acute myocardial infarction (MI) (n=20; FIG. 10J); chronic obstructive pulmonary disease (COPD) (n=24; FIG. 10K); and sarcoidosis (n=45; FIG. 10L). FIGS. 10A-10L show ROC curves illustrating the sensitivity and specificity for the each of the diseases listed above.

Materials and Methods

Study Subjects

The model was developed from two 'phase II' specimen sets (i.e. samples collected from women prior to surgery or chemotherapy): one set was from Effects of Regional Analgesia on Serum microRNAs after Oncology Surgery (ERASMOS), and the other set from the Pelvic Mass Protocol (PMP) (Cramer et al., 2010, Correlates of the preoperative level of CA125 at presentation of ovarian cancer. Gynecologic Oncology 119:462-468; Elias et al., 2015, A prospective phase 0 study on the effects of anesthetic selection on serum miRNA profiles during primary cytoreductive surgery for suspected ovarian cancer. Gynecologic Oncology 137:1). Healthy subjects from the New England Case-Control (NECC) study were selected as controls. The NECC study was a large epidemiologic study matching cases of ovarian cancer to geographically situated controls (Rice et al., 2013, Tubal ligation, hysterectomy and epithelial ovarian cancer in the New England Case-Control Study. International Journal of Cancer 133:2415-2421). These studies were approved by the Dana-Farber Cancer Institute Institutional Review Board Protocol 05-060 (NECC study), Brigham and Women's Hospital Institutional Review Board Protocol 2000-P-001678 (Pelvic Mass Protocol), and Dana-Farber/Harvard Cancer Center Institutional Review Board Protocol 12-532 (ERASMOS). All subjects were enrolled after signing informed consent, and samples were collected fresh in 13×75 mm BD Vacutainer Plus Plastic Serum tubes (BD Life Sciences, Franklin Lakes, NJ) with spray-coated silica. Samples were allowed to clot 1 hr at room temperature before processing, then spun down by centrifugation at 1300×g×10 min, aliquoted into 1.5 ml vials and stored at −80 C. Samples from the other studies were thawed and aliquoted for the current study and then refrozen.

ERASMOS Study

The Effects of Regional Analgesia on Serum microRNAs after Oncology Surgery (ERASMOS) study was an observational Phase 0 study that enrolled 60 patients from March 2013-May 2015, conducted as a follow-up study to a prior publication associating regional analgesia exposure with improved ovarian cancer outcomes. Patients were approached consecutively for enrollment. Eligible patients were scheduled to undergo exploratory laparotomy for a pelvic mass suspicious for invasive epithelial ovarian cancer. All patients were enrolled after signing informed consent. The final patient cohort consisted of 60 patients with 3 patients excluded for inadequate sample collection. As the diagnosis for patients was not known a priori, a few cases of invasive ovarian cancer of other histologies (for example granulosa cell tumor and leiomyosarcoma) were identified but retained in the cohort analysis as classifying these as "benign" or excluding them would reduce the clinical utility of the testing strategy. The serum blood samples used in the present study were collected immediately preoperatively for each patient.

Pelvic Mass Protocol (PMP)

The Pelvic Mass Protocol (PMP) enrolled women referred to the DFCI/BWH Gynecologic Oncology service over the period 1992 to 2013 (Williams et al., 2014, Prognostic significance and predictors of the neutrophil-to-lymphocyte ratio in ovarian cancer. Gynecologic Oncology 132:542-550.). The PMP was a prospective study performed at BWH collecting serum from women scheduled to undergo surgery for a known adnexal mass. Of some 455 women with a pelvic mass enrolled, a total of 120 samples were selected from the following categories: serous cystadenoma (Samuel and Carter, 2016, The diagnostic and prognostic potential of micrornas in epithelial ovarian carcinoma. Molecular Diagnosis & Therapy 21:59-73), serous borderline tumor (Samuel and Carter, 2016, The diagnostic and prognostic potential of micrornas in epithelial ovarian carcinoma. Molecular Diagnosis & Therapy 21:59-73), Stage I/II invasive serous adenocarcinoma (Hausler et al., 2010, Whole blood-derived miRNA profiles as potential new tools for ovarian cancer screening. British Journal of Cancer 103:693-700), and Stage III/IV invasive serous adenocarcinoma (Wang et al., 2016, Diagnostic potential of tumor DNA from ovarian cyst fluid. eLife 5:e15175), endometrioma (Samuel and Carter, 2016, The diagnostic and prognostic potential of micrornas in epithelial ovarian carcinoma. Molecular Diagnosis & Therapy 21:59-73), Stage I/II invasive clear cell or endometrioid adenocarcinoma (Hausler et al., 2010, Whole blood-derived miRNA profiles as potential new tools for ovarian cancer screening. British Journal of Cancer 103:693-700), or Stage III/IV invasive clear cell or endometrioid adenocarcinoma (Wang et al., 2016, Diagnostic potential of tumor DNA from ovarian cyst fluid. eLife 5:e15175). Overall, 37% of the subjects had benign disease, 12.6% had borderline tumors, 10.1% had low grade carcinomas, and 40.4% had high grade carcinomas. One sample of serous cystadenoma was excluded as an outlier due to a recent cardiovascular event as evidenced by extreme elevation of myocardial ischemia-associated miRNAs. From the most recent phase (2004-2008) of the NECC study, fifteen age and race matched healthy controls were selected; the controls were matched to the demographics of the EOC cases and benign disease controls from the PMP study. There was no overlap of subjects between the two studies. The samples sizes were based on a plan for a 2:1 ratio of early stage (Stage I/II) cancer cases to advanced stage (Stage III/IV) cases, a 1:1 ratio of invasive cancer cases: benign/borderline/control subjects, and for balanced numbers of healthy control: benign serous: benign endometrioid: borderline serous subjects. Borderline endometrioid or clear cell tumors were exceedingly rare and thus not included. For the qPCR model, 113 epithelial ovarian cancer cases and 113 healthy controls were added, matched for age and collection year. Twenty samples failed quality control, leaving 206 additional samples to add to the 119 samples originally profiled from PMP and creating a 325 sample set for qPCR-based model building and cut-off calibration.

Study Subjects for External Validation

Serum samples were collected from consecutive women undergoing surgical evaluation at the Medical University of Lodz, Poland, for a pelvic mass in association with an IRB-approved tumor collection protocol. All subjects were enrolled after signing informed consent, and samples were collected fresh in 13×75 mm BD Vacutainer Plus Plastic Serum tubes (BD Life Sciences, Franklin Lakes, NJ) with spray-coated silica. Samples were allowed to clot 1 hr at room temperature before processing, then spun down by centrifugation at 1300×g for 10 min, aliquoted into 1.5 ml vials and stored at −80° C. Samples were thawed only for the present study.

Outcome

Samples were classified as either invasive cancer or benign/borderline/controls. Although borderline tumors are not strictly benign, they are clinically indolent and seldom fatal; thus borderline samples were grouped with benign lesions, as the goal was to diagnose the tumors most contributing to mortality. For each patient, an estimated probability of >0.5 was classified as predicting invasive ovarian cancer.

Next Generation Sequencing (NGS)

Sample preparation, library construction, and miRNA sequencing were performed by Exiqon, Inc. (Vedbæk, Denmark). 500 µl of human serum from each sample were analyzed in duplicate. RNA from each sample was isolated using the miRCURY RNA isolation kit (Exiqon, Vedbæk, Denmark) according to the manufacturer's protocol optimized for serum. The quality of the isolated RNA was checked using qPCR. Total RNA was converted into microRNA NGS libraries using the NEBNEXT library generation kit (New England Biolabs Inc., Ipswich, MA) according to the manufacturer's instructions. Each individual RNA sample had adaptors ligated to its 3' and 5' ends and converted into cDNA. Then the cDNA was pre-amplified with specific primers containing sample specific indices. After 18 cycles of pre-PCR the libraries were purified on QiaQuick columns and the insert efficiency evaluated by a Bioanalyzer 2100 instrument on a high sensitivity DNA chip (Agilent Inc., Lexington, MA). The microRNA cDNA libraries were size-fractionated on a LabChip XT (PerkinElmer, Waltham, MA) and a band representing adaptors and 15-40 bp insert excised using the manufacturer's instructions. Samples were then quantified using qPCR and concentration standards.

Based on quality of the inserts and the concentration measurements, the libraries were pooled in equimolar concentrations (all concentrations of libraries to be pooled were of the same concentration). The library pools were finally quantified again with qPCR and the optimal concentration of the library pool used to generate the clusters on the surface of a flowcell before sequencing using v3 sequencing methodology according to the manufacturer instructions (Illumina Inc., Dedham, MA). Samples were sequenced on the Illumina NextSeq 500 system (Illumina Inc., Dedham, MA) using a single-end read length of 50 nucleotides at an average of 10 million reads per sample. Sequence tags were mapped to miRbase 20 (mirbase.org/). After sequencing adapters were trimmed off as part of the base calling, trimming of adapters from the dataset revealed distinct peaks representing microRNA (~18-22 nt).

Novel microRNAs not in standard miRBase or Rfam classification were identified based on the prediction algorithm miRPara. Expression levels were quantified in tags per million (TPM). TPM is a unit used to measure expression in NGS experiments. The number of reads for a particular microRNA is divided by the total number of mapped reads and multiplied by 1 million. Primary sequencing data have been deposited in the Gene Expression Omnibus (GEO) database (ncbi.nlm.nih.gov/geo) in Accession No. GSE94533. The most stable miRNAs from the sequencing data were selected as normalizers using the NormFinder algorithm (Andersen et al., 2004).

qPCR Validation

Nine potential reference miRNAs were selected from the miRNA sequencing data using the NormFinder algorithm. Both the fourteen miRNAs from the diagnostic set and 9 potential reference miRNAs were quantified by qPCR using Exiqon (Vedbæk, Denmark) LNA-containing miRNA-specific probes. Briefly, miRNAs were polyadenylated and reverse transcribed into cDNA in a single reaction step, then transferred to pre-loaded plates of primers using a pipetting robot. cDNA and ExiLENT SYBR Green master mix were transferred to qPCR panels pre-loaded with primers using a pipetting robot. Amplification was performed on a Roche Lightcycler 480 (Roche, Basel, Switzerland). Amplification quality was determined by generating melting curves; reactions with low efficiency or multiple peaks on the melting curve were discarded. Raw Cq values and melting points, detected by the Lightcycler software, were exported. Assays with several melting points or with melting points deviating from assay specifications were flagged and removed from the dataset. Reactions with amplification efficiency below 1.6 were also removed. Assays giving Cq values within 5 Cq values of the negative control sample were also removed from the dataset. Spike-in positive controls and no template negative controls were included. Minimum detection values for qPCR were established at 42 cycles; miRNAs with no amplification before that number of qPCR cycles were assumed to have their expression undetectable, and a quantification cycle (Cq) value of 42 was imputed as a substitute value. Data were normalized to the average of the assays detected in all samples (n=120 samples). The nine selected reference miRNAs were re-evaluated after profiling for their stability across the arrays and the average of the four most stable probes (hsa-miR-423-3p, SEQ ID NO: 142; hsa-miR-191-5p, SEQ ID NO: 196; hsa-miR-221-3p, SEQ ID NO: 108; and hsa-miR-103a-3p, SEQ ID NO: 55) was used as the reference for the change in Cq (dCq) calculations.

Comparison of Preoperative and Postoperative Samples

Individual miRNAs measurements from preoperative and postoperative serum samples from the ERASMOS study had been measured previously using multiplexed miRNA hydrogel probes (Fire-Plex, Abcam, Cambridge, MA) on a flow cytometer. Samples were profiled in duplicate, then replicates were merged. Fluorescence intensity values across all samples were normalized with Firefly Analysis Workbench (Abcam, Cambridge, MA) using the geNorm algorithm to identify appropriate normalizers (Vandesompele et al., 2002).

Pathology Samples

Paraffin blocks were selected from the surgical pathology files of the Brigham and Women's Hospital per BWH IRB Protocol #2016P002742. Hematoxylin and eosin sections of the cases were reviewed by a gynecologic pathologist (CC). The tissues had been routinely fixed in 10% neutral formalin and embedded in paraffin. Immunohistochemistry for TP53 and Ki-67 were performed using commercially available antibodies as previously described (Perets et al., 2013). Appropriate positive and negative (without primary antibodies) controls were used simultaneously for each antibody. In situ hybridization was performed using commercially available RNA probes from Exiqon (Vedbæk, Denmark) according to the manufacturer's instructions. All probe concentrations were 1 nM. A probe for the small nuclear RNA U6 served as a positive control while a non-targeting scramble RNA probe served as negative control.

Sample Size Estimation

A testing set was sought showing a superiority of 0.1 in the area under the receiver operating characteristic curve (AUC) against a value of 0.75 (assumed as a null hypothesis for a clinically useful biomarker) with a statistical power of 80% and a type 1 error probability <0.05 (Hanley and McNeil, 1982). For statistical power estimation purposes, it was assumed that the model predictions would be moderately correlated with CA-125 levels (r >0.3). The calculation yielded a required testing set of 44 patients (22 with invasive cancer and 22 without invasive cancer). To train the classifiers, it was assumed that the training set would require 3-fold more patients (N=132) bringing the total number of required patient samples to 176 samples. The sample size was increase to 180 to account for potential clinical or technical outliers.

Statistical Analysis

Basic Statistics

Differences in the distribution of histopathologic diagnoses, grade, and stage between the cohorts and datasets were calculated using chi-square tests. Differences in false-positive and false-negative assignment were compared using Fisher's exact test. Differences in age and CA-125 levels between the cohorts and datasets were calculated using a Mann-Whitney U test. For all tests, a two-tailed p-value <0.05 was considered significant. For the ROC curves, cut-off values for prediction with the best diagnostic performance were established using the Youden index {sensitivity$_c$+specificity$_c$−1}. Tests were performed in R.

Variable Selection Methods

For significance-based criterion, a student's t test was used, assuming miRNAs with p<0.05 and false discovery rate <0.05 for cancer versus benign/borderline/controls as significant.

For the fold change filter, miRNAs were selected that showed fold changes <0.8 or >1.2 for cancer versus benign/borderline/control comparisons in both the NECC and ERASMOS cohorts.

Correlation-based Feature Subset Selection (CFS) is a wrapper feature selection method that evaluates the worth of a subset of attributes by considering the individual predictive ability of each feature along with the degree of redundancy between them. Subsets of features that were highly correlated with the class while having low intercorrelation were preferred in the process. Search of the space of attribute subsets was performed by greedy hillclimbing augmented with a backtracking facility. This method of searching, called "Best First", started with the empty set of attributes and searched the set forward.

All three sets of variables were analyzed using 11 different models. Six models (linear discriminant analysis, logistic regression, multivariate adaptive regression splines, naive Bayes, neural network, and support vector machine) were developed using STATISTICA Data Miner 12.5 (StatSoft, Tulsa, OK, USA). The remaining five models (functional tree, LAD tree, Bayesian network, elastic net regression, and random forest) were created using Weka 3.9.0 (University of Waikato, New Zealand). Descriptions of the classification models are presented below.

Linear Discriminant Analysis (LDA)

The linear discriminant analysis method creates a new set of spatial coordinates that allow for linear separation of the groups. The most discriminative features were extracted on the basis of their correlations and the model used a backward stepwise variable selection algorithm only retaining in the model variables that showed final F values >5. This two-step filtering (variable selection after one of the three initial variable filtering algorithms) of the variables used in sample classification was aimed at the reduction of the number of miRNAs required for the model to work.

Depending on the number of variables selected by the filters, the discriminatory function of the LDA was based on a reduced set of miRNAs that passed the F value threshold and were retained in the model. For the subset of miRNAs filtered by statistical significance, the model used three miRNAs: hsa-miR-30d-5p (SEQ ID NO: 43), hsa-miR-200c-3p (SEQ ID NO: 105) and hsa-miR-320d (SEQ ID NO: 116).

For CFS variable selection the model used three miRNAs: hsa-miR-320d (SEQ ID NO: 116), hsa-miR-200a-3p (SEQ ID NO: 104), and hsa-miR-16-2-3p (SEQ ID NO: 18). The variable selection method based on stratified fold change used a yet another different set of miRNAs: hsa-miR-200c-3p (SEQ ID NO: 105), hsa-miR-320d (SEQ ID NO: 116), and hsa-miR-150-5p (SEQ ID NO: 83).

Logistic Regression

As above, the logistic regression model was built using a backward stepwise variable selection procedure, with variables showing p<0.15 being retained in the final model. The procedure allowed for second order interactions between the variables to detect potential subgroup-specific effects. A standard quasi-Newton estimation procedure was performed in model development.

After exclusion of variables with p values >0.15 in the multivariate model, the miRNAs remaining in the classifier were hsa-miR-30d-5p (SEQ ID NO: 43), hsa-miR-320d (SEQ ID NO: 116), hsa-miR-200c-3p (SEQ ID NO: 105), hsa-miR-1246 (SEQ ID NO: 178), and an interaction of hsa-miR-200c-30p* hsa-miR-1246 (SEQ ID NO: 178). A logistic regression model based on miRNAs selected by the CFS variable algorithm required only two miRNAs to work: hsa-miR-200c-3p (SEQ ID NO: 105) and hsa-miR-320d (SEQ ID NO: 116). A logistic regression classifier built on the fold change filter-selected miRNAs used three miRNAs: hsa-miR-150-5p (SEQ ID NO: 83), hsa-miR-320d (SEQ ID NO: 116), hsa-miR-1246 (SEQ ID NO: 178), and an interaction between hsa-miR-200c-3p (SEQ ID NO: 105)* hsa-miR-1246 (SEQ ID NO: 178). Results of all three models were convergent and the crucial role of hsa-miR-200c-3p (SEQ ID NO: 105)/hsa-miR-320d (SEQ ID NO: 116) was confirmed by all models. The logistic regression model achieved a similar performance to that of the neural net in the CFS-selected variable subset. This was a logical consequence of a strong variable filtering leaving too few input variables for the network to identify subtle patterns.

Multivariate Adaptive Regression Splines (MARS)

An alternative approach to modeling of the classification function was the MARS model—a modification of a multivariate joint-point regression which estimates a number of basal functions most appropriate for data from specific fragments of the multidimensional dataset. The method is used in complex function modeling of non-monotonous or non-linear associations. Within our analysis we used a MARS model that allowed for up to third degree interactions between the variables, allowing for up to 1.5*(n variables) basal function in each model and penalizing the introduction of additional basal functions by a factor of 2. Interactions between variables were tested for improvement of model performance up to the degree of three. During the model building procedure we iteratively removed variables absent in any of the basal functions until only miRNAs used in at least one basal function remained in the MARS model.

Using 11 miRNAs filtered on the basis of significance, a MARS model was created, which included 14 basal functions. All functions were transformation of five, single miRNAs: hsa-miR-30d-5p (SEQ ID NO: 43), hsa-miR-200c-3p (SEQ ID NO: 105), hsa-miR-450b-5p (SEQ ID NO: 149), hsa-miR-200a-3p (SEQ ID NO: 104), and hsa-miR-1307-3p (SEQ ID NO: 181). The MARS model built on CFS-filtered variables consisted of seven basal functions based on four miRNAs: hsa-miR-200c-3p (SEQ ID NO: 105), hsa-miR-320d (SEQ ID NO: 116), hsa-miR-16-2-3p (SEQ ID NO: 18), and hsa-miR-320b (SEQ ID NO: 114). The final MARS model built on 14 miRNAs filtered by the stratified fold change threshold was optimized at 10 basal functions based on five miRNAs: hsa-miR-200c-3p (SEQ ID NO: 105), hsa-miR 5p (SEQ ID NO: 83), hsa-miR-200a-3p (SEQ ID NO: 104), hsa-miR-92-3p (SEQ ID NO: 47), hsa-miR-203a (SEQ ID NO: 106), and hsa-miR-320c (SEQ ID NO: 115). All MARS models showed relatively poor performance hinting at issues with model overfitting and low specificity (for example, the ROC AUC for the significance-based and CFS variable selection inputs did not meet statistical significance).

Elastic Net Regression

An elastic-net regularized generalized linear model is a linear regression using coordinate descent. In order to train this model we have used Java implementation of a component of the R package 'glmnet' in Weka software. As a regression method for classification was desired, class was binarized and one regression model was built for each class value (i.e. meta-scheme classification via regression). The alpha elastic-net mixing parameter was chosen to be 0.001 while the epsilon value for generating the lambda sequence was set to $10^{-4}$. Additionally, a covariance update method was used. This resulted in the following formula: weka.classifiers.meta.ClassificationViaRegression-W weka.classifiers.functions.ElasticNet---m2 y-alpha 0.001-lambda seq-thr 1.0E-7-mxit 10000000-numModels 100-in-folds 10-eps 1.0E-4-sparse n-stderr_rule n-addStats n. Reproduction of model induction may require installing additional packages from WEKA package manager.

Neural Network

Five thousand (5000) neural networks were built for each variable selection method (15,000 networks in total), and the best neural network (in terms of performance in properly assigning classes to the test set) was retained. The networks were built in a semi-automated way. Their structure was of a multilayer perceptron with a number of neurons in the hidden layer iteratively optimized from (n variables)/3 to (n variables)*1.5 to avoid overfitting. Admissible linking functions between the layers were linear, logistic, hyperbolic tangential, and exponential. Neuron weights were calculated using the BFGS (Broyden-Fletcher-Goldfarb-Shanno) algorithm and the network was trained in each epoch using an error back-propagation algorithm to optimize weights in each pass.

Support Vector Machine (SVM)

This classifier was built with a set of different entry parameters: kernel function types, function parameters, and hinge loss function. Admissible kernel functions were linear, polynomial ($2^{nd}$ and $3^{rd}$ order) and radial basis function (gamma from 0.1 to 1 tested in 0.1 increments). The models performed worse than simpler classification tools (logistic regression/linear discriminant analysis), possibly due to a small number of cases available for testing.

Naïve Bayes Classifier

A priori class probabilities were estimated empirically on the basis of class frequencies in the dataset, normal distribution was assumed for all log-10 transformed miRNA expression values quantified as transcripts per million. The exact probability estimator of the naïve Bayes classifier showed similar performance on all three variable subsets, achieving accuracy comparable to that of the SVM model LAD Tree LADTree is completely deterministic tree that allows decision making by counting respective probabilities on the pathway though the tree. Multi-class alternating decision tree using the LogitBoost strategy (LAD Tree; ECML '02 Proceedings of the 13th European Conference on Machine Learning, pp. 161-172, Aug. 19-23, 2002). The number of boosting iterations to use, which determined the size of the trees, was set to be 10.

Formula: weka.classifiers.trees.LADTree-B 10. Reproduction of model induction may require installing additional packages from WEKA package manager.

Functional Tree

Functional trees are logistic classification decision trees that have logistic regression functions at the inner nodes or leaves. Training of models was performed by WEKA software. As in default settings, minimum number of instances at which a node is considered for splitting was 15, number of iterations for LogitBoost was also 15 and no weight trimming was applied.

Formula: weka.classifiers.trees.FT-I 15-F 0-M 15-W 0.0. Please note that reproduction of model induction may require installing additional packages from WEKA package manager.

All functional trees were models with one node. In order to infer how this model works, evaluation of values for linear combination function at each node for every class has to be done. For example, for cancer in the CFS-processed dataset the formula is:

$$F1=-1.75+[hsa\text{-}miR\text{-}16\text{-}2\text{-}3p]*-0.29+[hsa\text{-}miR\text{-}200a\text{-}3p]*0.08\ \text{I}hsa\text{-}miR\text{-}200c\text{-}30*1.07+[hsa\text{-}miR\text{-}320b]*-0.21+[hsa\text{-}miR\text{-}320d]*1.29$$

As the classifiers are binary, the result for the second class (F2) should be an opposite number (F1=−F2). In the next step the value of the following formula should be calculated and compared to threshold of the node:

$$\frac{e^{F1}}{e^{F1}+e^{F2}}$$

Bayesian Network

A Bayes Network was trained using a K2 search algorithm, which is a hill climbing algorithm restricted by an order on the variables. The initial network used for structure learning was a Naive Bayes Network and there could be only one parent a node. Conditional probability tables of a Bayes network were driven directly from data once the structure has been learned (with alpha value equal to 0.5). Formula: weka.classifiers.bayes.BayesNet-D-Q weka.classifiers.bayes.net search.local.K2-P 1-S BAYES-E weka.classifiers.bayes.net.estimate.SimpleEstimator---A 0.5. Reproduction of model induction may require installing additional packages from WEKA package manager.

Random Forest

Random forest is a technique of random decision forests that considers K randomly chosen attributes at each node. K was calculated as integer of 1 plus binary logarithm of number of predictors. Minimum proportion of the variance needed at a node in order for splitting to be performed was set to 0.001. No backfitting was performed.

Formula: weka.classifiers.trees.RandomForest-P 100-I 100-num-slots 1-K 0-M 1.0-V 0.001-S 1. Reproduction of model induction may require installing additional packages from WEKA package manager.

What is claimed is:

1. A method of treating ovarian cancer in a selected subject, the method comprising administering to the selected subject one or more treatments for ovarian cancer, wherein the subject is selected by
   (a) detecting in a biological sample obtained from the subject one or more microRNA (miRNA) biomarkers selected from the group consisting of hsa-miR-23b-3p (SEQ ID NO: 29), hsa-miR-29a-3p (SEQ ID NO: 39), hsa-miR-32a-5p (SEQ ID NO: 46), hsa-miR-92a-3p (SEQ ID NO: 47), hsa-miR-150-5p (SEQ ID NO: 83), hsa-miR-200a-3p (SEQ ID NO: 104), hsa-miR-200c-3p (SEQ ID NO: 105), hsa-miR-203a-5p (SEQ ID NO: 106), hsa-miR-320c (SEQ ID NO: 115), hsa-miR-320d (SEQ ID NO: 116), hsa-miR-335-5p (SEQ ID NO: 122), hsa-miR-450b-5p (SEQ ID NO: 149), hsa-miR-1246 (SEQ ID NO: 178), hsa-miR-1307-5p (SEQ ID NO: 182);
   (b) determining that the one or more miRNA biomarkers in the sample exhibits fold-change expression relative to a control; and
   (c) selecting the subject for the one or more ovarian cancer treatments.

2. The method of claim 1, wherein the one or more miRNAs is selected from the group consisting of hsa-miR-92a-3p (SEQ ID NO: 47), hsa-miR-450b-5p (SEQ ID NO: 149), hsa-miR-335-5p (SEQ ID NO: 122), hsa-miR-29a-3p (SEQ ID NO: 39), hsa-miR-1307-5p (SEQ ID NO: 182), hsa-miR-320c (SEQ ID NO: 115), and hsa-miR-200c-3p (SEQ ID NO: 105).

3. The method of claim 1, wherein the biological sample is selected from blood, plasma, serum, lymph node tissue, draining lymph node tissue for an ovary, ovarian tissue, ovarian tissue comprising a tumor or mass, or pelvic tissue.

4. The method of claim 1, wherein the control is a preoperative or postoperative sample, a sample obtained from a healthy subject; a sample obtained from a subject with benign disease; a sample obtained from a subject having a cancer other than ovarian cancer, or a combination thereof.

5. The method of claim 1, wherein the subject is a human patient.

6. The method of claim 1, wherein the subject has, is at risk of developing, or is suspected of having ovarian cancer or metastatic ovarian disease.

7. The method of claim 1, wherein detecting the one or more biomarkers comprises nucleic acid probe detection, optical detection, fluorophore detection, luminescent detection, chemiluminescent detection, flow cytometry detection, enzyme linked immunosorbent assay (ELISA) detection, radiographic detection, microarray detection, polymerase chain reaction (PCR) detection, next-generation sequencing detection, mass spectrometry detection, or a combination thereof.

8. The method of claim 1, wherein two or more, three or more, four or more, five or more, six or more, or seven or more of the miRNA biomarkers are detected in the biological sample.

* * * * *